(12) United States Patent
Lin et al.

(10) Patent No.: US 9,453,038 B2
(45) Date of Patent: Sep. 27, 2016

(54) GLUCOKINASE ACTIVATOR COMPOUNDS, COMPOSITIONS CONTAINING SUCH COMPOUNDS, AND METHODS OF TREATMENT

(71) Applicant: Merck Sharp & Dohme Corp., Rahway, NJ (US)

(72) Inventors: Songnian Lin, Holmdel, NJ (US); Rui Zhang, Plainsboro, NJ (US); Brian Campbell, Bensalem, PA (US); Sunita V. Dewnani, Secaucus, NJ (US); Jiayi Xu, Marlboro, NJ (US); Libo Xu, Bridgewater, NJ (US); Emma R. Parmee, Doylestown, PA (US); Roman Kats-Kagan, New Haven, CT (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/652,883

(22) PCT Filed: Dec. 12, 2013

(86) PCT No.: PCT/US2013/074574
§ 371 (c)(1),
(2) Date: Jun. 17, 2015

(87) PCT Pub. No.: WO2014/099578
PCT Pub. Date: Jun. 26, 2014

(65) Prior Publication Data
US 2015/0336991 A1 Nov. 26, 2015

Related U.S. Application Data

(60) Provisional application No. 61/738,126, filed on Dec. 17, 2012.

(51) Int. Cl.
| | | |
|---|---|---|
| *C07F 9/6539* | (2006.01) | |
| *A61K 31/4439* | (2006.01) | |
| *C07D 401/04* | (2006.01) | |
| *A61K 31/444* | (2006.01) | |
| *C07D 471/04* | (2006.01) | |
| *A61K 31/437* | (2006.01) | |
| *C07F 9/58* | (2006.01) | |
| *A61K 31/675* | (2006.01) | |
| *A61K 31/497* | (2006.01) | |
| *A61K 31/427* | (2006.01) | |
| *C07F 9/6558* | (2006.01) | |
| *C07F 7/08* | (2006.01) | |
| *C07D 401/14* | (2006.01) | |
| *C07D 403/04* | (2006.01) | |
| *C07D 403/14* | (2006.01) | |
| *C07D 417/14* | (2006.01) | |

(52) U.S. Cl.
CPC ............ *C07F 9/6539* (2013.01); *A61K 31/427* (2013.01); *A61K 31/437* (2013.01); *A61K 31/444* (2013.01); *A61K 31/4439* (2013.01); *A61K 31/497* (2013.01); *A61K 31/675* (2013.01); *C07D 401/04* (2013.01); *C07D 401/14* (2013.01); *C07D 403/04* (2013.01); *C07D 403/14* (2013.01); *C07D 417/14* (2013.01); *C07D 471/04* (2013.01); *C07F 7/0812* (2013.01); *C07F 9/587* (2013.01); *C07F 9/65583* (2013.01)

(58) Field of Classification Search
None
See application file for complete search history.

(56) References Cited

U.S. PATENT DOCUMENTS

| | | | |
|---|---|---|---|
| 2009/0118304 A1* | 5/2009 | Takahashi | ............ C07D 401/04 514/255.05 |
| 2010/0267708 A1 | 10/2010 | Kim et al. | |
| 2011/0098297 A1 | 4/2011 | Yasuma et al. | |

FOREIGN PATENT DOCUMENTS

| | | |
|---|---|---|
| WO | 2007/037534 A1 | 4/2007 |
| WO | 2010/018800  * | 2/2010 |
| WO | 2014/099584 A1 | 6/2014 |

OTHER PUBLICATIONS

International Search Report of PCT/US2013/074574 completed Mar. 14, 2014.
Written Opinion of PCT/US2013/074574 completed Mar. 14, 2014.

* cited by examiner

*Primary Examiner* — Karl J Puttlitz
(74) *Attorney, Agent, or Firm* — Anna L. Cocuzzo; Catherine D. Fitch

(57) ABSTRACT

Novel pyridine-2-carboxamide derivatives of formula I: and pharmaceutically acceptable salts thereof are disclosed as useful for treating or preventing type 2 diabetes and similar conditions. The compounds are effective as glucokinase activating agents. Pharmaceutical compositions and methods of treatment are also included.

16 Claims, No Drawings

GLUCOKINASE ACTIVATOR COMPOUNDS, COMPOSITIONS CONTAINING SUCH COMPOUNDS, AND METHODS OF TREATMENT

CROSS-REFERENCE TO RELATED APPLICATIONS

This application is a U.S. National Phase application under 35 U.S.C. § 371 of PCT/US2013/074574, filed Dec. 13, 2013, which published as WO 2014/099578 on Jun. 26, 2014, which claims priority from U.S. provisional application 61/738,126 filed Dec. 17, 2012.

FIELD OF THE INVENTION

The present invention relates to novel glucokinase activator compounds and salts thereof. The present invention further relates to compositions containing such compounds, and methods of use thereof.

BACKGROUND OF THE INVENTION

The present invention relates to glucokinase activators. In particular, the present invention is directed to compounds useful for the treatment of diabetes, especially type 2 diabetes, as well as related diseases and conditions such as obesity and metabolic syndrome.

Glucokinase (GK)(ATP: D-hexose 6-phosphotransferase, EC 2.7.1.1) is one of 4 types of hexokinase (hexokinase IV) in mammals. Hexokinase is an enzyme that acts in the first stage of the glycolytic pathway catalyzing the reaction from glucose to glucose 6-phosphate. Glucokinase is localized mainly in the liver and the beta cells of the pancreas where it controls the rate-determining step of glucose metabolism. Notably, in 3 types of hexokinase (I, II, and III) other than glucokinase, the enzyme activities are saturated at a 1 mM or lower concentration of glucose, whereas the Km of glucokinase for glucose is 8 mM, which value is proximate to the physiological blood sugar level. Therefore, the intracellular glucose metabolism is accelerated through glucokinase in response to the change of blood sugar level from normal (5 mM) to postprandial elevation (10-15 mM).

Results in recombinant mice expressing glucokinase have demonstrated that in fact glucokinase plays an important role in the generalized homeostasis of glucose. Though mice in which the glucokinase gene has been destroyed result in death shortly after birth (Grupe A, et al., "Transgenic knock-outs reveal a critical requirement for pancreatic beta cell glucokinase in maintaining glucose homeostasis", Cell, 83, 1995, P. 69-78.), the blood sugar level is decreased in normal and diabetic mice where glucokinase is generated in excess (Ferre T, et al., "Correction of diabetic alterations by glucokinase", Proceedings of the National Academy of Sciences of the U.S.A., 93, 1996, P. 7225-7230). With increase of the glucose concentration, the reactions of the pancreatic beta cells and hepatocytes move toward decreasing the blood sugar level.

This means that glucokinase works as a glucose sensor in humans and plays an important role in glucose homeostasis. As such, it is believed that for a large number of type II diabetic patients, it may be possible to regulate blood sugar level utilizing a glucokinase sensor system.

The disclosed glucokinase-activating substances are expectected to accelerate insulin secretion in the pancreatic beta cells, and accelerate sugar uptake and inhibit sugar release in liver. Thus, they are considered useful as therapeutic agents in the treatment of type II diabetes.

It has furthermore been elucidated that the occurrence of glucokinase of the pancreatic beta cell type is localized in the brain of rats, particularly in the feeding center (ventromedial hypothalamus; VMH). About 20% of the neurocytes in VMH, called the glucose responsive neuron, are believed to play an important role in control of body weight. Feeding of rats is decreased when glucose is administered into the brain, while inhibition of the glucose metabolism by intracerebral administration of a glucose analog, glucosamine, causes hyperphagia. From electrophysiological experiments, it has been recognized that the glucose responsive neuron is activated in response to the physiological change of glucose concentration (5-20 mM), but its activity is inhibited by inhibiting the glucose metabolism with glucosamine The same mechanism through glucokinase has been assumed in the sensor system for the glucose concentration in VHM as in the insulin secretion in the pancreatic beta cells. Therefore, in addition to the action in the liver and pancreatic beta cells, a glucokinase-activating substance in VMH is expected to improve not only the blood sugar lever but also obesity which is a problem in a large number of type II diabetic patients.

SUMMARY OF THE INVENTION

The present invention addresses compounds represented by the formula:

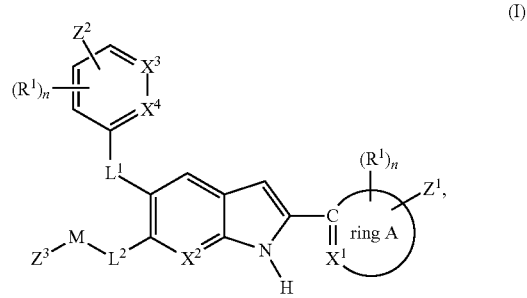

(I)

and pharmaceutically acceptable salts thereof. The present invention further relates to methods of treating diabetes and related diseases and conditions.

DETAILED DESCRIPTION OF THE INVENTION

The present invention addresses the following compounds, compounds of (1)-(39):

(1) A compound of the formula (I):

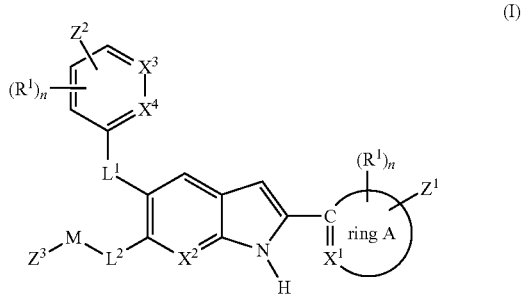

(I)

or a pharmaceutically acceptable salt thereof, wherein:
$X^1$, $X^2$, $X^3$ and $X^4$ individually represent CH or N wherein $X^3$ and $X^4$ can not both be N;

M represents a 6- to 10-membered aryl group, a 5- to 7-membered heteroaryl group, a 5- to 7-membered cycloalkyl group, or a 5- to 7-membered aliphatic heterocyclic group, optionally substituted with 1-4 substituents independently selected from: halogen, hydroxy, oxo, $C_{1-6}$alkyl, $C_{1-6}$alkylO$C_{1-6}$alkyl, $C_{1-6}$alkoxy, CN, NR$^2$R$^4$, $C_{1-6}$alkylNR$^2$R$^4$, $C(O)_{1-2}C_{1-6}$alkyl, $C_{1-6}$alkylC(O)$_{1-2}$$C_{1-6}$alkyl, C(O)OH, $C_{1-6}$alkylCOOH, $S(O)_{0-2}C_{1-6}$alkyl, $S(O)_{0-2}$ or aryl$C_{1-6}$alkyl, wherein the alkyl and alkoxy substituents are further optionally substituted by 1-4 substituents independently selected from: halogen or $C_{1-6}$alkyl where said $C_{1-6}$alkyl is optionally substituted by 1-6 halogens;

L$^1$ represents O or $S(O)_{0-2}$;

L$^2$ represents a single bond, O, $S(O)_{0-2}$, or CR$^2$R$^4$;

L$^3$ represents $C_{1-6}$alkyl, O$C_{1-6}$alkyl, $S(O)_{0-2}C_{1-6}$alkyl, $C_{1-6}$alkylO$C_{1-6}$alkyl, $C_{1-6}$alkylS(O)$_{0-2}C_{1-6}$alkyl, or CONH$C_{1-6}$alkyl;

Z$^1$, Z$^2$ and Z$^3$ individually represent -L$^3$-COOR, —P(O)R$^3$OR, -L$^3$-P(O)R$^3$OR or null; provided that Z$^1$, Z$^2$ and Z$^3$ can not all three be null together;

R individually represents H, $C_{1-6}$alkyl or $C_{1-6}$cycloalkyl, optionally substituted with 1-4 substituents independently selected from: halogen or hydroxy;

R$^2$ and R$^4$ individually represent H or $C_{1-6}$alkyl, where the $C_{1-6}$alkyl is optionally substituted with 1-4 substituents independently selected from: halogen or hydroxy;

R$^1$ represents H, halogen, $C_{1-6}$alkyl, $C_{1-6}$cycloalkyl, O$C_{1-6}$alkyl, $S(O)_{0-2}C_{1-6}$alkyl, $C_{1-6}$alkylO$C_{1-6}$alkyl, $C_{1-6}$alkylS(O)$_{0-2}C_{1-6}$alkyl, NR$^2$R$^4$, $C_{1-6}$alkylNR$^2$R$^4$ or C(O)NR$^2$R$^4$, wherein the alkyl substituents are optionally substituted with 1-4 substituents independently selected from: halogen or hydroxy; and further wherein the R$^2$ and R$^4$ on the C(O)NR$^2$R$^4$ can together form a 4- to 6-membered saturated heterocyclic ring having 1 nitrogen atom which 4- to 6-membered ring may be optionally substituted with 1-3 substituents independently selected from halogen, hydroxyl, oxo, $C_{1-6}$alkyl, $C_{1-6}$alkoxy or CO$_2C_{1-6}$alkyl where the alkyl or alkoxy substituents are optionally substituted by 1-6 halogens;

R$^3$ represents $C_{1-6}$alkyl or O$C_{1-6}$alkyl, n represents 1-4, and ring A represents a 5- to 7-membered monocyclic or 9- to 10-membered bicyclic heteroaryl group in which the carbon atom attached to the amide nitrogen atom contained in formula (I) forms C=N together with the nitrogen atom in the ring.

(2) A compound of (1), wherein M represents a 5- to -6-membered aryl or heteroaryl group, or a 5- to 6-membered aliphatic heterocyclic group, optionally substituted with 1-4 substituents independently selected from: halogen, hydroxy, oxo, $C_{1-6}$alkyl, $C_{1-6}$alkylO$C_{1-6}$alkyl, $C_{1-6}$alkoxy, CN, NR$^2$R$^4$, $C_{1-6}$alkylNR$^2$R$^4$, $C(O)_{1-2}C_{1-6}$alkyl, $C_{1-6}$alkylC(O)$_{1-2}C_{1-6}$alkyl, C(O)OH, $C_{1-6}$alkylCOOH, $S(O)_{0-2}C_{1-6}$alkyl, $S(O)_{0-2}$ or aryl$C_{1-6}$alkyl, wherein the alkyl and alkoxy substituents are further optionally substituted by 1-4 substituents independently selected from: halogen or $C_{1-6}$alkyl where said $C_{1-6}$alkyl is optionally substituted by 1-6 halogens; or a pharmaceutically acceptable salt thereof.

(3) A compound of (1) or (2), wherein M represents a 5- to 6-membered aryl or heteroaryl group, or a 5- to 6-membered aliphatic heterocyclic group, optionally substituted with 1-4 substituents independently selected from: halogen, oxo, $C_{1-6}$alkyl, $C_{1-6}$alkylO$C_{1-6}$alkyl, $C_{1-6}$alkoxy, $C(O)_{1-2}$$C_{1-6}$alkyl, $C_{1-6}$alkylC(O)$_{1-2}C_{1-6}$alkyl, C(O)OH, or $C_{1-6}$alkylCOOH, wherein the alkyl is further optionally substituted by 1-6 halogen substituents; or a pharmaceutically acceptable salt thereof.

(4) A compound of any of (1)-(3), wherein M is a phenyl group, isothiazolyl group, imidazolyl group, oxazolyl group, thiadiazolyl group, thienyl group, triazolyl group, tetrazolyl group, pyridyl group, pyrimidinyl group, furyl group, thiazolyl group, isoxazolyl group or pyrazolyl group, optionally substituted with halogen, hydroxy, oxo, $C_{1-6}$alkyl, $C_{1-6}$alkylO$C_{1-6}$alkyl, $C_{1-6}$alkoxy, CN, NR$^2$R$^4$, $C_{1-6}$alkylNR$^2$R$^4$, $C(O)_{1-2}C_{1-6}$alkyl, $C_{1-6}$alkylC(O)$_{1-2}C_{1-6}$alkyl, C(O)OH, $C_{1-6}$alkylCOOH, $S(O)_{0-2}C_{1-6}$alkyl, $S(O)_{0-2}$ or aryl$C_{1-6}$alkyl, wherein the alkyl and alkoxy substituents are further optionally substituted by 1-4 substituents independently selected from: halogen or $C_{1-6}$alkyl where said $C_{1-6}$alkyl is optionally substituted by 1-6 halogens; or a pharmaceutically acceptable salt thereof.

(5) A compound of any of (1)-(4) wherein M is phenyl, pyrrolidine or pyridyl, optionally substituted with 1-4 substituents independently selected from: halogen, oxo, $C_{1-6}$alkyl, $C_{1-6}$alkylO$C_{1-6}$alkyl, $C_{1-6}$alkoxy, $C(O)_{1-2}$$C_{1-6}$alkyl, $C_{1-6}$alkylC(O)$_{1-2}C_{1-6}$alkyl, C(O)OH or $C_{1-6}$alkylCOOH, wherein the alkyl is further optionally substituted by 1-6 halogen substituents; or a pharmaceutically acceptable salt thereof.

(6) A compound of any of (1)-(5) wherein M is phenyl or pyrrolidine, optionally substituted with 1-4 substituents independently selected from: halogen, oxo, $C_{1-6}$alkyl, $C_{1-6}$alkylO$C_{1-6}$alkyl, $C_{1-6}$alkoxy, $C(O)_{1-2}C_{1-6}$alkyl, $C_{1-6}$alkylC(O)$_{1-2}C_{1-6}$alkyl, C(O)OH or $C_{1-6}$alkylCOOH, wherein the alkyl is further optionally substituted by 1-6 halogen substituents; or a pharmaceutically acceptable salt thereof.

(7) A compound of any of (1)-(6) wherein M is pyrrolidine, optionally substituted with 1-4 substituents independently selected from: oxo, $C_{1-6}$alkyl, $C_{1-6}$alkylCOOH or $C(O)C_{1-6}$alkyl, wherein the alkyl is further optionally substituted by 1-6 halogen substituents; or a pharmaceutically acceptable salt thereof.

(8) A compound of any of (1)-(5) wherein M is pyrrolidine, optionally substituted with 1-4 substituents independently selected from: oxo, $C_{1-6}$alkyl, $C_{1-6}$alkylO$C_{1-6}$alkyl, $C_{1-6}$alkoxy, $C(O)_{1-2}C_{1-6}$alkyl, $C_{1-6}$alkylC(O)$_{1-2}C_{1-6}$alkyl, C(O)OH or $C_{1-6}$alkylCOOH, wherein the alkyl is further optionally substituted by 1-6 halogen substituents, and further wherein one substituent is oxo; or a pharmaceutically acceptable salt thereof.

(9) A compound of any of (1)-(5) wherein M is phenyl, optionally substituted with 1-4 halogen substituents; or a pharmaceutically acceptable salt thereof.

(10) A compound of any of (1)-(5) wherein M is pyridyl, optionally substituted with 1-4 substituents independently selected from: halogen, oxo, $C_{1-6}$alkyl, $C_{1-6}$alkylO$C_{1-6}$alkyl, $C_{1-6}$alkoxy, $C(O)_{1-2}C_{1-6}$alkyl, $C_{1-6}$alkylC(O)$_{1-2}C_{1-6}$alkyl, C(O)OH or $C_{1-6}$alkylCOOH, wherein the alkyl is further optionally substituted by 1-6 halogen substituents; or a pharmaceutically acceptable salt thereof.

(11) A compound of any of (1)-(10) wherein L$^1$ is O; or a pharmaceutically acceptable salt thereof.

(12) A compound of any of (1)-(11) wherein L$^2$ is a single bond or CR$^2$R$^4$; or a pharmaceutically acceptable salt thereof.

(13) A compound of any of (1)-(12) wherein L$^2$ is a single bond or CH$_2$; or a pharmaceutically acceptable salt thereof.

(14) A compound of any of (1)-(13) wherein L$^3$ is $C_{1-6}$alkyl, O$C_{1-6}$alkyl or CONH$C_{1-6}$alkyl; or a pharmaceutically acceptable salt thereof.

(15) A compound of any of (1)-(14) wherein one of $Z^1$, $Z^2$ and $Z^3$ is -$L^3$-COOR, —P(O)$R^3$OR or -$L^3$-P(O)$R^3$OR, and the other two are null; or a pharmaceutically acceptable salt thereof.

(16) A compound of any of (1)-(15) wherein one of $Z^1$, $Z^2$ and $Z^3$ is -$L^3$-COOR or —P(O)$R^3$OR, and the other two are null; or a pharmaceutically acceptable salt thereof.

(17) A compound of any of (1)-(15) wherein $Z^1$ is -$L^3$-COOR and $Z^2$ and $Z^3$ are null; or a pharmaceutically acceptable salt thereof.

(18) A compound of any of (1)-(15) wherein $Z^1$ is —P(O)$R^3$OR and $Z^2$ and $Z^3$ are null; or a pharmaceutically acceptable salt thereof.

(19) A compound of any of (1)-(15) wherein $Z^1$ is -$L^3$-P(O)$R^3$OR and $Z^2$ and $Z^3$ are null; or a pharmaceutically acceptable salt thereof.

(20) A compound of any of (1)-(15) wherein $Z^2$ is -$L^3$-COOR and $Z^1$ and $Z^3$ are null; or a pharmaceutically acceptable salt thereof.

(21) A compound of any of (1)-(15) wherein $Z^2$ is —P(O)$R^3$OR and $Z^1$ and $Z^3$ are null; or a pharmaceutically acceptable salt thereof.

(22) A compound of any of (1)-(15) wherein $Z^2$ is -$L^3$-P(O)$R^3$OR and $Z^1$ and $Z^3$ are null; or a pharmaceutically acceptable salt thereof.

(23) A compound of any of (1)-(15) wherein $Z^3$ is -$L^3$-COOR and $Z^1$ and $Z^2$ are null; or a pharmaceutically acceptable salt thereof.

(24) A compound of any of (1)-(15) wherein $Z^3$ is —P(O)$R^3$OR and $Z^1$ and $Z^2$ are null; or a pharmaceutically acceptable salt thereof.

(25) A compound of any of (1)-(15) wherein $Z^3$ is -$L^3$-P(O)$R^3$OR and $Z^1$ and $Z^2$ are null; or a pharmaceutically acceptable salt thereof.

(26) A compound of any of (1)-(14) wherein $Z^1$, $Z^2$ and $Z^3$ individually represent -$L^3$-COOR, —P(O)$R^3$OR or null; provided that $Z^1$, $Z^2$ and $Z^3$ can not all three be null together; or a pharmaceutically acceptable salt thereof.

(27) A compound of any of (1)-(26) wherein R individually represents H or $C_{1-6}$alkyl, wherein the $C_{1-6}$alkyl is optionally substituted with 1-6 halogen substituents; or a pharmaceutically acceptable salt thereof.

(28) A compound of any of (1)-(27) wherein R individually represents H or $C_{1-2}$alkyl, wherein the $C_{1-2}$alkyl is optionally substituted with 1-6 halogen substituents; or a pharmaceutically acceptable salt thereof.

(29) A compound of any of (1)-(28) wherein $R^1$ is individually selected from hydrogen, halogen, $C_{1-6}$alkyl, $C_{1-6}$alkylO$C_{1-6}$alkyl, S(O)$_{0-2}C_{1-6}$alkyl, or C(O)NR$^2$R$^4$, wherein the alkyl substituents are optionally substituted with 1-4 substituents independently selected from: halogen or hydroxy; and further wherein the $R^2$ and $R^4$ on the C(O)NR$^2$R$^4$ together form a 4-membered saturated heterocyclic ring having 1 nitrogen atom which 4-membered ring may be optionally substituted with 1-3 substituents independently selected from halogen, hydroxyl, oxo, $C_{1-6}$alkyl, $C_{1-6}$alkoxy, or CO$_2$C$_{1-6}$alkyl where the alkyl or alkoxy substituents are optionally substituted by 1-6 halogens; or a pharmaceutically acceptable salt thereof.

(30) A compound of any of (1)-(29) wherein $R^1$ is individually selected from H or $C_{1-6}$alkyl, wherein the $C_{1-6}$alkyl is optionally substituted with 1-6 halogen substituents; or a pharmaceutically acceptable salt thereof.

(31) A compound of any of (1)-(29) wherein $R^1$ is individually selected from H or S(O)$_{0-2}C_{1-6}$alkyl, wherein the S(O)$_{0-2}C_{1-6}$alkyl is optionally substituted with 1-6 halogen substituents; or a pharmaceutically acceptable salt thereof.

(32) A compound of any of (1)-(29) wherein $R^1$ is individually selected from H or C(O)azetidine; or a pharmaceutically acceptable salt thereof.

(33) A compound of any of (1)-(32) wherein ring A is a 5- to 7-membered monocyclic or a 9- to 10-membered bicyclic aryl or heteroaryl group substituted with —($R^1$)$_m$, and —$Z^1$ as illustrated in formula I; or a pharmaceutically acceptable salt thereof.

(34) A compound of any of (1)-(33) wherein ring A is a substituted phenyl, isothiazolyl group, imidazolyl group, oxazolyl group, thiadiazolyl group, thienyl group, triazolyl group, tetrazolyl group, pyridyl group, pyrimidinyl group, furyl group, thiazolyl group, isoxazolyl group or pyrazolyl group; or a pharmaceutically acceptable salt thereof.

(35) A compound of any of (1)-(34) wherein ring A is a substituted pyridyl, pyrazinyl or phenyl group; or a pharmaceutically acceptable salt thereof.

(36) A compound of formula (II):

(II)

or a pharmaceutically acceptable salt thereof, wherein:

$X^1$, $X^3$, $X^4$ and $X^5$ individually represent CH or N wherein $X^3$ and $X^4$ can not both be N;

$L^1$ represents O or S;

one of $Y^1$ and $Y^2$ is -$L^3$-COOR, —P(O)$R^3$OR or -$L^3$-P(O)$R^3$OR; and the other is H, halogen, $C_{1-6}$alkyl, $C_{1-6}$cycloalkyl, OC$_{1-6}$alkyl, S(O)$_{0-2}C_{1-6}$alkyl, $C_{1-6}$alkylOC$_{1-6}$alkyl, $C_{1-6}$alkylS(O)$_{0-2}C_{1-6}$alkyl, NR$^2$R$^4$, $C_{1-6}$alkylNR$^2$R$^4$ or C(O)NR$^2$R$^4$, wherein the alkyl substituents are optionally substituted with 1-4 substituents independently selected from: halogen or hydroxy, and further wherein the $R^2$ and $R^4$ on the C(O)NR$^2$R$^4$ can together form a 4- to 6-membered saturated heterocyclic ring having 1 nitrogen atom which 4- to 6-membered ring may be optionally substituted with 1-3 substituents independently selected from halogen, hydroxyl, oxo, $C_{1-6}$alkyl, $C_{1-6}$alkoxy or CO$_2$C$_{1-6}$alkyl where the alkyl or alkoxy substituents are optionally substituted by 1-6 halogens;

$L^3$ represents $C_{1-6}$alkyl, OC$_{1-6}$alkyl, S(O)$_{0-2}C_{1-6}$alkyl, $C_{1-6}$alkylOC$_{1-6}$alkyl, $C_{1-6}$alkylS(O)$_{0-2}C_{1-6}$alkyl or CONHC$_{1-6}$alkyl;

R individually represents H, $C_{1-6}$alkyl or $C_{1-6}$cycloalkyl, optionally substituted with 1-4 substituents independently selected from: halogen or hydroxy;

$R^2$ and $R^4$ individually represent H or $C_{1-6}$alkyl, where the $C_{1-6}$alkyl is optionally substituted with 1-4 substituents independently selected from: halogen or hydroxy; and $R^3$ represents $C_{1-6}$alkyl or OC$_{1-6}$alkyl.

(37) A compound of formula (III):

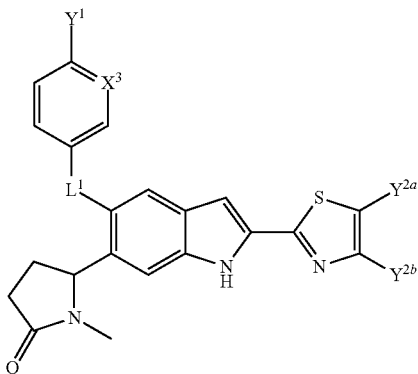

(III)

or a pharmaceutically acceptable salt thereof, wherein:
$X^3$ is CH or N;
$L^1$ represents O or S;
$Y^1$ is H, halogen, $C_{1-6}$alkyl, $C_{1-6}$cycloalkyl, $OC_{1-6}$alkyl, $S(O)_{0-2}C_{1-6}$alkyl, $C_{1-6}$alkylOC$_{1-6}$alkyl, $C_{1-6}$alkylS(O)$_{0-2}$C$_{1-6}$alkyl, $NR^2R^4$, $C_{1-6}$alkylNR$^2$R$^4$ or $C(O)NR^2R^4$, wherein the alkyl substituents are optionally substituted with 1-4 substituents independently selected from: halogen or hydroxy; and further wherein the $R^2$ and $R^4$ on the $C(O)NR^2R^4$ can together form a 4- to 6-membered saturated heterocyclic ring having 1 nitrogen atom which 4- to 6-membered ring may be optionally substituted with 1-3 substituents independently selected from halogen, hydroxyl, oxo, $C_{1-6}$alkyl, $C_{1-6}$alkoxy or $CO_2C_{1-6}$alkyl where the alkyl or alkoxy substituents are optionally substituted by 1-6 halogens;
one of $Y^{2a}$ and $Y^{2b}$ is -$L^3$-COOR, —P(O)R$^3$OR or -$L^3$-P(O)R$^3$OR; and the other is H, halogen, $C_{1-6}$alkyl, $C_{1-6}$cycloalkyl, $OC_{1-6}$alkyl, $S(O)_{0-2}C_{1-6}$alkyl, $C_{1-6}$alkylOC$_{1-6}$alkyl, $C_{1-6}$alkylS(O)$_{0-2}$C$_{1-6}$alkyl, $NR^2R^4$, $C_{1-6}$alkylNR$^2$R$^4$ or $C(O)NR^2R^4$, wherein the alkyl substituents are optionally substituted with 1-4 substituents independently selected from: halogen or hydroxy, and further wherein the $R^2$ and $R^4$ on the $C(O)NR^2R^4$ can together form a 4- to 6-membered saturated heterocyclic ring having 1 nitrogen atom which 4- to 6-membered ring may be optionally substituted with 1-3 substituents independently selected from halogen, hydroxyl, oxo, $C_{1-6}$alkyl, $C_{1-6}$alkoxy or $CO_2C_{1-6}$alkyl where the alkyl or alkoxy substituents are optionally substituted by 1-6 halogens;
$L^3$ represents $C_{1-6}$alkyl, $OC_{1-6}$alkyl, $S(O)_{0-2}C_{1-6}$alkyl, $C_{1-6}$alkylOC$_{1-6}$alkyl, $C_{1-6}$alkylS(O)$_{0-2}$C$_{1-6}$alkyl or $CONHC_{1-6}$alkyl;
R individually represents H, $C_{1-6}$alkyl or $C_{1-6}$cycloalkyl, optionally substituted with 1-4 substituents independently selected from: halogen or hydroxy;
$R^2$ and $R^4$ individually represent H or $C_{1-6}$alkyl, where the $C_{1-6}$alkyl is optionally substituted with 1-4 substituents independently selected from: halogen or hydroxy; and
$R^3$ represents $C_{1-6}$alkyl or $OC_{1-6}$alkyl
(38) A compound of (37) wherein $Y^1$ is $S(O)_{0-2}C_{1-6}$alkyl.
(39) A compound of (I) which is elsewhere disclosed herein or is:
methyl 3-(6-{5-[4-(ethylsulfonyl)phenoxy]-6-(1-methyl-5-oxopyrrolidin-2-yl)-1H-indol-2-yl}pyridin-3-yl)propanoate;
3-(6-{5-[4-(ethylsulfonyl)phenoxy]-6-(1-methyl-5-oxopyrrolidin-2-yl}-1H-indol-2-yl}pyridin-3-yl)propanoic acid;
(2-{5-[4-(ethylsulfonyl)phenoxy]-2-[5-(trifluoromethyl)pyridin-2-yl]-1H-indol-6-yl}-5-oxopyrrolidin-1-yl)acetic acid;
methyl 3-[4-({6-(1-methyl-5-oxopyrrolidin-2-yl)-2-[5-(trifluoro-methyl)pyridin-2-yl]-1H-indol-5-yl}oxy)phenyl]propionate;
3-[4-({6-(1-methyl-5-oxopyrrolidin-2-yl)-2-[5-(trifluoromethyl)pyridin-2-yl]-1H-indol-5-yl}oxy)phenyl]propanoic acid;
methyl 3-(6-{6-(2-fluorophenoxy)-5-[4-(methylsulfonyl)phenoxy]-1H-indol-2-yl}pyridin-3-yl)propanoate;
3-(6-{6-(2-fluorophenoxy)-5-[4-(methylsulfonyl)phenoxy]-1H-indol-2-yl}pyridin-3-yl)propanoic acid;
n-({6-[6-(1-methyl-5-oxopyrrolidin-2-yl)-5-{[6-(methylsulfonyl)pyridin-3-yl]oxy}-1H-indol-2-yl]pyridin-3-yl}-carbonyl)-β-alanine;
3-[6-(5-{[6-(methylsulfonyl)pyridin-3-yl]oxy}-6-[(2-oxopyrrolidin-1-yl)methyl]-1H-pyrrolo[2,3-b]pyridin-2-yl)pyridin-3-yl]propanoic acid;
methyl 3-{6-[6-(1-acetylpyrrolidin-2-yl)-5-{[6-(azetidin-1-ylcarbonyl)pyridin-3-yl]oxy}-1H-indol-2-yl]pyridin-3-yl}propanoate;
3-{6-[6-(1-acetylpyrrolidin-2-yl)-5-{[6-(azetidin-1-ylcarbonyl)pyridin-3-yl]oxy}-1H-indol-2-yl]pyridin-3-yl}propanoic acid;
(6-(5-(4-(ethylsulfonyl)phenoxy)-6-(1-methyl-5-oxopyrrolidin-2-yl)-1H-indol-2-yl)pyridin-3-yl)(methyl)phosphinic acid;
methyl 3-(6-(6-(1-methyl-5-oxopyrrolidin-2-yl)-5-((6-(methylsulfonyl)pyridin-3-yl)oxy)-1H-indol-2-yl)pyridin-3-yl)propanoate;
3-(6-(6-(1-methyl-5-oxopyrrolidin-2-yl)-5-((6-(methylsulfonyl)pyridin-3-yl)oxy)-1H-indol-2-yl)pyridin-3-yl)propanoic acid;
methyl 3-(6-(6-(1-methyl-5-oxopyrrolidin-2-yl)-5-(4-(methylsulfonyl)phenoxy)-1H-indol-2-yl)pyridin-3-yl)propanoate;
3-(6-(6-(1-methyl-5-oxopyrrolidin-2-yl)-5-(4-(methylsulfonyl)phenoxy)-1H-indol-2-yl)pyridin-3-yl)propanoic acid;
2,2-dimethyl-3-(6-(6-(1-methyl-5-oxopyrrolidin-2-yl)-5-((6-(methylsulfonyl)pyridin-3-yl)oxy)-1H-indol-2-yl)pyridin-3-yl)propanoic acid;
2-((6-(6-(1-methyl-5-oxopyrrolidin-2-yl)-5-((6-(methylsulfonyl)pyridin-3-yl)oxy)-1H-indol-2-yl)pyridin-3-yl)oxy)acetic acid;
3-(6-(5-((6-(methoxymethyl)pyridin-3-yl)oxy)-6-(1-methyl-5-oxopyrrolidin-2-yl)-1H-indol-2-yl)pyridin-3-yl)propanoic acid;
2-(4-((6-(1-methyl-5-oxopyrrolidin-2-yl)-2-(5-(trifluoromethyl)pyridin-2-yl)-1H-indol-5-yl)oxy)phenyl)acetic acid;
3-(4-((6-(1-methyl-5-oxopyrrolidin-2-yl)-2-(pyrazin-2-yl)-1H-indol-5-yl)oxy)phenyl)propanoic acid;
3-(4-((6-(1-methyl-5-oxopyrrolidin-2-yl)-2-phenyl-1H-indol-5-yl)oxy)phenyl)propanoic acid;
methyl 3-(4-((6-(1-methyl-5-oxopyrrolidin-2-yl)-2-(pyrazin-2-yl)-1H-indol-5-yl)oxy)phenyl)propanoate;
3-(4-((6-(1-methyl-5-oxopyrrolidin-2-yl)-2-(pyridin-2-yl)-1H-indol-5-yl)oxy)phenyl)propanoic acid;
methyl 2-(4-((6-(1-methyl-5-oxopyrrolidin-2-yl)-2-(pyridin-2-yl)-1H-indol-5-yl)oxy)phenyl)acetate;
methyl 3-(4-((6-(1-methyl-5-oxopyrrolidin-2-yl)-2-(pyridin-2-yl)-1H-indol-5-yl)oxy)phenyl)propanoate;
2-(4-((6-(1-methyl-5-oxopyrrolidin-2-yl)-2-(pyridin-2-yl)-1H-indol-5-yl)oxy)phenyl)acetic acid;
methyl 3-(6-(6-(1-methyl-5-oxopyrrolidin-2-yl)-5-(pyridin-2-ylthio)-1H-indol-2-yl)pyridin-3-yl)propanoate;

3-(6-(6-(1-methyl-5-oxopyrrolidin-2-yl)-5-(pyridin-2-yl-thio)-1H-indol-2-yl)pyridin-3-yl)propanoic acid;
2-(5-chloro-2-(6-(1-methyl-5-oxopyrrolidin-2-yl)-5-((6-(methylsulfonyl)pyridin-3-yl)oxy)-1H-indol-2-yl)thiazol-4-yl)acetic acid;
3-(2-(6-(1-methyl-5-oxopyrrolidin-2-yl)-5-((6-(methylsulfonyl)pyridin-3-yl)oxy)-1H-indol-2-yl)thiazol-5-yl)propanoic acid;
methyl 2-(2-(6-(1-methyl-5-oxopyrrolidin-2-yl)-5-(4-(methylsulfonyl)phenoxy)-1H-indol-2-yl)thiazol-4-yl)acetate;
2-(5-chloro-2-(6-(1-methyl-5-oxopyrrolidin-2-yl)-5-(4-(methylsulfonyl)phenoxy)-1H-indol-2-yl)thiazol-4-yl)acetic acid;
2-(2-(6-(1-methyl-5-oxopyrrolidin-2-yl)-5-(4-(methylsulfonyl)phenoxy)-1H-indol-2-yl)thiazol-4-yl)acetic acid;
methyl 3-(2-(6-(1-methyl-5-oxopyrrolidin-2-yl)-5-(4-(methylsulfonyl)phenoxy)-1H-indol-2-yl)thiazol-5-yl)propanoate;
3-(2-(6-(1-methyl-5-oxopyrrolidin-2-yl)-5-(4-(methylsulfonyl)phenoxy)-1H-indol-2-yl)thiazol-5-yl)propanoic acid;
diethyl((2-(6-(1-methyl-5-oxopyrrolidin-2-yl)-5-((6-(methylsulfonyl)pyridin-3-yl)oxy)-1H-indol-2-yl)thiazol-5-yl)methyl)phosphonate;
or a pharmaceutically acceptable salt thereof.

The present invention also relates to pharmaceutical compositions comprising compounds of any of (1)-(39) and a pharmaceutically acceptable carrier.

Additionally, the present invention relates to use of a compound of any of (1)-(39) in the manufacture of a medicament for use in treating obesity or diabetes.

The present invention relates to the use of a compound of any of (1)-(39) in therapy, for example, in the treatment of diabetes.

The present invention further relates to a method for the treatment of a obesity or diabetes comprising administering to an individual a pharmaceutical composition comprising a compound of any of (1)-(39).

Another embodiment of the present invention includes a method of treating a condition selected from: (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension or other conditions and disorders where insulin resistance is a component, in a mammalian patient in need of such treatment, comprising administering to the patient a compound of any of (1)-(39) in an amount that is effective to treat said condition.

Yet another embodiment of the present invention include a method of treating a condition selected from: (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension or other conditions and disorders where insulin resistance is a component, in a mammalian patient in need of such treatment, comprising administering to the patient a compound of any of (1)-(39), and a compound from one of the following classes of compounds:

(1) dipeptidyl peptidase-IV (DPP-4) inhibitors (e.g., sitagliptin, alogliptin, linagliptin, vildagliptin, saxagliptin, teneligliptin, MK-3102);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BIM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) other glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, CNX011, CNX 01162, CNX 01167, JTT 851, SAR1, MR 1704, TUG 770, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, ertugliflozin, remogloflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof;

(37) GPR 120 agonists (such as KDT501), said compounds being administered to the patient in an amount that is effective to treat said condition.

The invention is further described herein using the terms defined below unless otherwise specified.

"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

"Alkoxy" refers to an alkyl group linked to oxygen.

"Aryl", alone or in combination, relates to a phenyl, naphthyl or indanyl group. In specific embodiments, the "aryl" is phenyl. The abbreviation "Ph" represents phenyl.

"Cycloalkyl" means a saturated cyclic hydrocarbon radical having the number of carbon atoms designated. If no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Heteroaryl" (HAR) unless otherwise specified, means an aromatic or partially aromatic heterocycle that contains at least one ring heteroatom selected from oxygen ("O"), sulfur ("S") and nitrogen ("N"). Heteroaryls thus includes heteroaryls fused to other kinds of rings, such as aryls, cycloalkyls and heterocycles that are not aromatic. Examples of heteroaryl groups include: pyrrolyl or pyrrole, isoxazolyl or isoxazole, isothiazolyl or isothiazole, pyrazolyl or pyrazole, pyridyl, oxazolyl or oxazole, oxadiazolyl or oxadiazole, thiadiazolyl or thiadiazole, thiazolyl or thiazole, imidazolyl or imidazole, triazolyl or triazole, tetrazolyl or tetrazole, furyl, triazinyl, thienyl, pyrimidyl, benzisoxazolyl or benzisoxazole, benzoxazolyl or benzoazole, benzothiazolyl or benzothiazole, benzothiadiazolyl or benzothiadiazole, dihydrobenzofuranyl or dihydrobenzofurane, indolinyl or indoline, pyridazinyl or pyridazine, indazolyl or indazole, isoindolyl or isoindole, dihydrobenzothienyl, indolizinyl or indolizine, cinnolinyl or cinnoline, phthalazinyl or phthalazine, quinazolinyl or quinazoline, naphthyridinyl or naphthyridine, carbazolyl or carbazole, benzodioxolyl or benzodioxole, quinoxalinyl or quinoxaline, purinyl or purine, furazanyl or furazane, isobenzylfuranyl or isobenzylfurane, benzimidazolyl or benzimidazole, benzofuranyl or benzofurane, benzothienyl or benzothiene, quinolyl or quinoline, oxo-dihydroqunoline, indolyl or indole, oxindole, isoquinolyl or isoquinoline, dibenzofuranyl or dibenzofurane, and the like. For heterocyclic and heteroaryl groups, rings and ring systems containing from 5-15 atoms are included, forming 1-3 rings.

"Heterocycle" or "heterocyclic" refers to nonaromatic cyclic ring structures in which one or more atoms in the ring, the heteroatom(s), is an element other than carbon. Heteroatoms are typically O, S or N atoms.

"Halogen" (Halo) includes fluorine, chlorine, bromine and iodine.

Unless expressly depicted or described otherwise, variables depicted in a structural formula with a "floating" bond, such as substituent -L-T, are permitted on any available carbon atom in the ring to which each is attached.

Substitution, where applicable, may be on any available carbon atom that results in a stable structure. Furthermore, where language indicates that certain groups or substituents are further optionally substituted, that language includes all groups or substituents having that feature. For example, use of the language "wherein the alkyl and alkoxy substituents are further optionally substituted" indicates that any substituents possessing an alkyl and alkoxy component can be substituted within that component.

Also, number ranges where provided (e.g., 1-4, 0-3, etc.) expressly include each and every number in that range as a discrete embodiment.

Atoms of the compounds described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of any of (1)-(39). For example, different isotopic forms of hydrogen (H) include protium (1H) and deuterium (2H). Protium is the predominant hydrogen isotope found in nature. Enriching for deuterium may yield certain therapeutic advantages, such as increasing in vivo half-life or reducing dosage requirements, or may provide a compound useful as a standard for characterization of biological samples. Isotopically-enriched compounds of any of (1)-(39) described herein can be prepared without undue experimentation by conventional techniques well known to those skilled in the art or by processes analogous to those described in the Schemes and Examples herein using appropriate isotopically-enriched reagents and/or intermediates.

Individual tautomers of the compounds of any of (1)-(39), as well as mixtures thereof, are encompassed herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the compounds of (1)-(39). The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of any of (1)-(39) and pharmaceutically acceptable salts thereof.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of any of (1)-(39) may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of any of (1)-(39) are also included in the present invention.

Of import, the disclosed compounds have glucokinase activation activity, and therefore they are useful as therapeutic agents and/or preventive agents for diabetes mellitus as well as for diabetic complication.

Diabetic complication means diseases caused by development of diabetes mellitus and includes, for example, diabetic nephropathy, diabetic retinopathy, diabetic neurosis, diabetic arteriosclerosis, and so on.

The compounds of the present invention are considered of potential utility in the treatment of both insulin dependent diabetes mellitus (IDDM) and non-insulin dependent diabetes mellitus (NIDDM).

Insulin dependent diabetes mellitus (IDDM) is a "multifactorial autoimmune disease for which susceptibility is determined by environmental and genetic factors"; see Tisch, R. and McDevitt, H. (1996) Cell 85. 291-297. Insulin dependent diabetes mellitus is classified as type I and type II depending on the predisposition.

In type II diabetes mellitus, the blood sugar after meals is markedly maintained at a high level for a long period of time in comparison with that of healthy persons.

Compounds disclosed herein may be used in the manufacture of medicaments for treating one or more of the following diseases or conditions, including, without limitation:

(1) noninsulin dependent diabetes mellitus (type 2 diabetes);
(2) hyperglycemia;
(3) metabolic syndrome/syndrome X;
(4) obesity;
(5) ischemia and myocardial infarction;
(6) neurological disorders such as Alzheimer's disease, schizophrenia, and impaired cognition;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) hyperapobetalipoproteinemia; and
(11) atherosclerosis.

The present invention also relates to a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of any of (1)-(39) or a pharmaceutically acceptable salt thereof. The compound may be used alone or advantageously may be administered with a cholesterol biosynthesis inhibitor, particularly an HMG-CoA reductase inhibitor (e.g., simvastatin, atorvastatin, and the like). The compound may also be used advantageously in combination with other lipid lowering drugs such as cholesterol absorption inhibitors (e.g., stanol esters, sterol glycosides or azetidinones such as ezetimibe), ACAT inhibitors (e.g., avasimibe), CETP inhibitors (e.g. anacetrapib), niacin, bile acid sequestrants, microsomal triglyceride transport inhibitors, and bile acid reuptake inhibitors. Such combination treatments are useful for the treatment or control of conditions such as hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound of (1)-(39). The compound may be used alone or advantageously may be administered with an anti-obesity agent, such as a lipase inhibitor (e.g., orlistat,) or a monoamine neurotransmitter uptake inhibitor (e.g., sibutramine or phentermine) The compound may also be used advantageously in combination with CB-1 inverse agonists or antagonists (e.g., rimonabant or taranabant).

The present invention further relates to a method of treating hyperglycemia, diabetes or insulin resistance in a mammalian patient in need of such treatment which comprises administering to said patient a compound of any of (1)-(39) in an amount that is effective to treat hyperglycemia, diabetes or insulin resistance.

Yet another aspect of the invention that is of interest relates to a method of treating atherosclerosis in a mammalian patient in need of such treatment, comprising administering to said patient a compound of any of (1)-(39) in an amount that is effective to treat atherosclerosis.

Yet another aspect of the invention that is of interest relates to a method of delaying the onset of one of the aforementioned conditions and disorders where insulin resistance is a component in a mammalian patient in need thereof, comprising administering to the patient a compound of any of (1)-(39) in an amount that is effective to delay the onset of said condition.

Yet another aspect of the invention that is of interest relates to a method of reducing the risk of developing one of the aforementioned conditions and disorders where insulin resistance is a component in a mammalian patient in need thereof, comprising administering to the patient a compound of any of (1)-(39) in an amount that is effective to reduce the risk of developing said condition.

Yet another aspect of the invention that is of interest relates to a method of treating a condition or reducing the risk of developing a condition or delaying the onset of a condition selected from the group consisting of (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound of any of (1)-(39) in an amount that is effective to treat said condition, and a compound selected from the group consisting of:

(1) dipeptidyl peptidase-IV (DPP-4) inhibitors (e.g., sitagliptin, alogliptin, linagliptin, vildagliptin, saxagliptin, teneligliptin, MK-3102);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BIM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g.,lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) other glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, CNX011, CNX 01162, CNX 01167, JTT 851, SARI, MR 1704, TUG 770, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, ertugliflozin, remogliflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof;

(37) GPR 120 agonists (such as KDT501); said compounds being administered to the patient in an amount that is effective to treat said condition.

For dosing purposes, any suitable route of administration may be employed for providing a mammal, especially a human, with an effective amount of a compound of the present invention. Dosage forms may include tablets, troches, dispersions, suspensions, solutions, capsules, creams, ointments, aerosols, and the like. Most preferably, compounds of any of (1)-(39) are administered orally. The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus or other diseases for which compounds of any of (1)-(39) are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response. Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

Another aspect of the invention that is of interest is a pharmaceutical composition comprised of a compound of any of (1)-(39) in combination with a pharmaceutically acceptable carrier. The pharmaceutical compositions of the present invention comprise a compound of any of (1)-(39) as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art.

In practical use, compounds of any of (1)-(39) can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compounds of any of (1)-(39) may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

As discussed supra, compounds of the present invention may be used in combination with other drugs that may also be useful in the treatment or amelioration of the individual diseases and conditions described herein. Such other drugs may be administered by a route and in an amount commonly used therefore, contemporaneously or sequentially with a compound of any of (1)-(39). In the treatment of patients who have type 2 diabetes, insulin resistance, obesity, metabolic syndrome, neurological disorders, and co-morbidities that accompany these diseases, more than one drug is commonly administered. The compounds of this invention may generally be administered to a patient who is already taking one or more other drugs for these conditions.

When a compound of any of (1)-(39) is used contemporaneously with one or more other drugs, a pharmaceutical composition in unit dosage form containing such other drugs and the compound of any of (1)-(39) is preferred. However, the combination therapy also includes therapies in which a compound of any of (1)-(39) and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of any of (1)-(39).

Examples of other active ingredients that may be administered separately or in the same pharmaceutical composition in combination with a compound of any of (1)-(39) include, but are not limited to:

(1) dipeptidyl peptidase-IV (DPP-4) inhibitors (e.g., sitagliptin, alogliptin, linagliptin, vildagliptin, saxagliptin, teneligliptin, MK-3102);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) dual agonists (e.g., ZYH2, ZYH1, GFT505, chiglitazar, muraglitazar, PPARα/γ aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO partial 2004/020409, WO 2004/020408, and WO 2004/066963); and (4) PPARγ agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BIM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g.,lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) other glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, CNX011, CNX 01162, CNX 01167, JTT 851, SARI, MR 1704, TUG 770, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, ertugliflozin, remogliflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof; or

(37) GPR 120 agonists (such as KDT501).

Another aspect of the invention that is of interest relates to the use of a compound of any of (1)-(39) in the manufacture of a medicament for use in treating a disease or condition described herein.

The glucokinase-activating capability of the compounds (I) may be determined according to methods previously described (e.g., Diabetes, 45, 1671-1677, 1996).

The glucokinase activity can, for instance, be determined without directly measuring glucose-6-phosphate by measuring the amount of Thio-NADH generated during the production of phosphogluconolactone from glucose-6-phosphate by a reporter enzyme glucose-6-phosphate dehydrogenase.

To test the exemplified compounds, the following assay was employed. Recombinant human liver glucokinase was expressed as a FLAG fusion protein in *E. coli*, and purified on ANTIFLAG M2 AFFINITY GEL (Sigma). The assay was carried out at 30° C. in a 96-well plate. In the plate was distributed 69 µl each of assay buffer (25 mM Hepes Buffer: pH=7.2, 2 mM $MgCl_2$, 1 mM ATP, 0.5 mM TNAD, 1 mM dithiothreitol), to which was added 1 µl of a DMSO solution of the compound or DMSO as control. Then, 20 µl of pre-ice-cooled enzyme mixture (FLAG-GK, 20 U/ml G6PDH) was distributed thereto, to which was added 10 µl of 25 mM glucose as substrate to initiate the reaction (final glucose concentration=2.5 mM). After starting the reaction, the absorbance at 405 nm was measured every 30 seconds for 10 minutes to evaluate the compound based on the initial increase for 5 minutes. FLAG-GK was added so that the increase of absorbance after 5 minutes fell between 0.05 to 0.1 in the presence of 1% DMSO.

The OD values of the respective compounds were measured in the respective concentrations, wherein the OD value of DMSO as control is regarded as 100%. From the OD values at the respective concentrations, Emax (%, 2.5 mM Glu) and EC50 (nM, 2.5 mM Glu) were calculated and used as indicators of the GK activation capability of the compounds. According to the above assay, the GK activation capability of the exemplified compounds of the present invention was determined. The following table shows the results. Where different enantiomers of the same compound were tested, two numbers are provided. Where 3 numbers are provided, for example, Ex. #30, data for the racemic form is also shown.

TABLE

| Ex. # | EC50 | Emax |
|---|---|---|
| 1 | 1.9 | 624.3 |
| 2 | 53.4 | 652.1 |
| 3 | 797.2 | 627.5 |
| 4 | 21.8 | 454.9 |
| 4 | 11.4 | 453.8 |
| 5 | 36.4 | 437.4 |
| 5 | 48.0 | 487.9 |
| 7 | 774.4 | 15.7 |
| 8 | 116.2 | 500.9 |
| 9 | 533.1 | 16280 |
| 10 | 13.9 | 418.8 |
| 11 | 187.3 | 410.4 |
| 12 | 53.6 | 614.4 |
| 15 | 3.8 | 664.5 |
| 15 | 24.6 | 559.4 |
| 16 | 51.5 | 667.6 |
| 16 | 111.3 | 558.7 |
| 17 | 108.1 | 642.8 |
| 18 | 81.0 | 612.4 |
| 19 | 71.8 | 430.6 |
| 20 | 63.9 | 521.2 |
| 21 | 39.1 | 628.5 |
| 22 | 455.9 | 410.3 |
| 23 | 2.1 | 573.5 |
| 24 | 17.1 | 604.1 |
| 24 | 15.1 | 653.2 |
| 25 | 21.0 | 649 |
| 26 | 4.3 | 545.2 |
| 27 | 23.8 | 630.3 |
| 28 | 281.1 | 665.9 |
| 28 | 157.3 | 698.2 |
| 28 | 709.6 | 317.1 |
| 29 | 1967 | 331.1 |
| 29 | 234.1 | 703.2 |
| 30 | 49.1 | 506.5 |
| 31 | 68.8 | 599.4 |
| 32 | 65.1 | 565.6 |
| 33 | 47.4 | 586.5 |
| 34 | 118.2 | 606.5 |
| 35 | 8.9 | 656 |
| 36 | 66.7 | 618.6 |
| 37 | 23.5 | 696.2 |

As shown in the table, the compounds of the present invention have sufficient GK activation capability when Emax and EC50 are employed as indicators. Furthermore, the disclosed and exemplified compounds have the potential to be more liver-preferring over the pancreas, enabling the disclosed and exemplified compounds to potentially reduce the risk of hypoglycemia in individuals being treated.

The compounds of the invention can be prepared using the synthetic schemes described herein as well as any of several alternate methods which will be apparent to a chemist skilled in the art. The following abbreviations may be used in the synthetic schemes or Examples: AcCl is acetyl chloride; DBU is 1,8-Diazabicycloundec-7-ene; DCM is dichloromethane; DIEA is N,N-Diisopropylethylamine; DMA is dimethylacetamide; DMAP is dimethylaminopyridine; DMF is N,N-dimethylformamide; DMI is 1.3-dimethyl-2-Imidazolidinone; DMSO is dimethyl sulfoxide; DTT is dithiothreitol; EDC or EDCI is 1-ethyl-3-[3-(dimethylamino)propyl]-carbodiimide HCl; EtOAc is ethyl acetate; EtOH is ethanol; h is hours; HATU is o-(7-Azabenzotriazol-1-yl)-N,N,N',N'-tetramethyluronium hexafluorophosphate; HCl is hydrochloric acid; HOBt is 1-hydroxybenzotriazole; HPLC is high performance liquid chromatography; IPA is isopropanol; LAH is lithium aluminum hydride; m is multiplet; M is molar; min is minutes; mmol is millimole; NCS is N-chlorosuccinimide; rt or RT is room temperature; SM is starting material; TBAF is tetra-n-butylammonium fluoride; TEA is triethylamine; TFA is trifluoroacetic acid; TFAA is trifluoroacetic anhydride; THF is tetrahydrofuran; TLC is thin layer chromatography; and TNAD is thionicotinarnide-adenine dinucleotide.

General Schemes

Compounds of the present invention may be prepared using conventional techniques or according to the methodology outlined in the following general synthetic schemes.

Multiple embodiments of the present invention are summarized in Scheme 1 which depicts the preparation of compounds Ia and Ib from intermediate 1, synthesized according to procedures in EP1935890, or described below. Intermediate 1 is subjected to Sonogashira coupling reactions with alkyne 2 using a preformed palladium catalyst such as bis(triphenylphosphine) palladium (II) dichloride, in the presence of copper (I) iodide and a base such as triethylamine in a solvent such as tetrahydrofuran. Indole ester Ia is formed by cyclization of intermediate 3 using a base such as tetrabutylammonium fluoride in a solvent such as tetrahydrofuran. Saponification of ester Ia to give compound Ib is achieved with a base such as aqueous lithium hydroxide (LiOH) or aqueous sodium hydroxide in a polar solvent such as tetrahydrofuran, methanol, ethanol or a mixture of similar solvents.

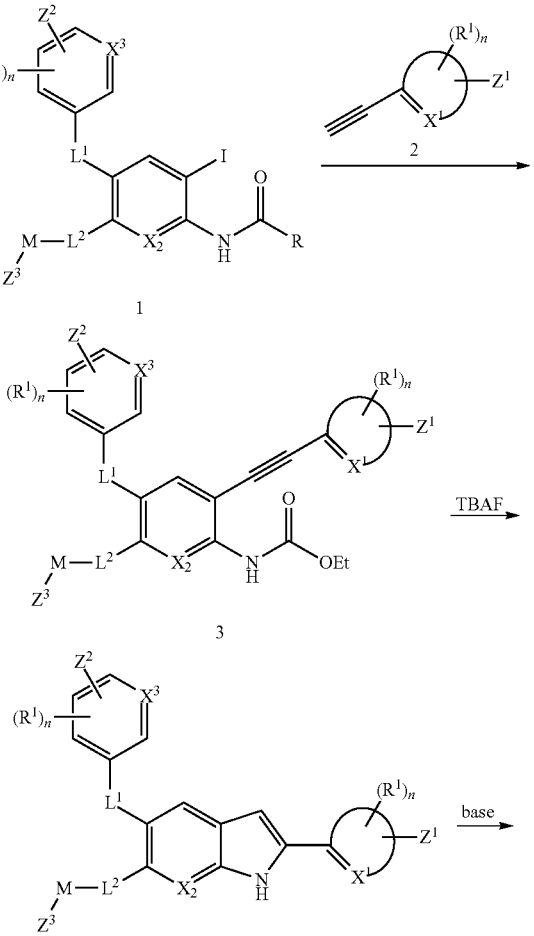

Scheme 1

-continued

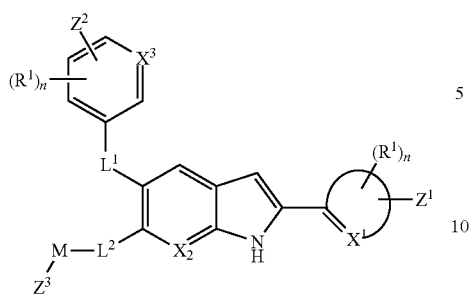

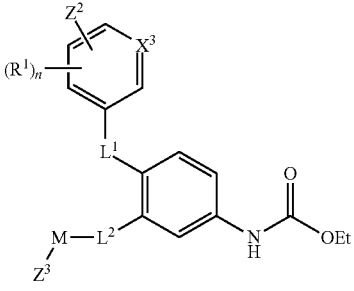

Intermediate 1 can be prepared from nitro intermediate 4, as shown in Scheme 2. The leaving group in 4 is displaced with a nucleophile such as substituted phenol, hydroxypyridine, thiophenol or pyridine thiophenol under standard conditions such as potassium carbonate in a polar solvent such as dimethylformamide. Intermediate 5 is transformed into 6 with a reducing system such as iron and aqueous ammonium chloride. Protecting the amino group with a suitable protecting group such as ethyl carbamate to intermediate 7, followed by iodination with a mixture of potassium iodide and potassium periodate in aqueous methanol and dioxane leads to intermediate 1.

Scheme 2

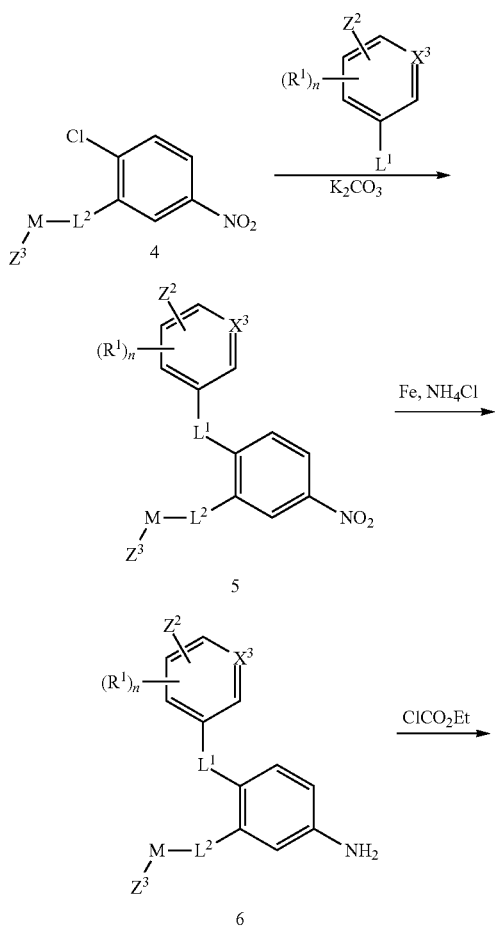

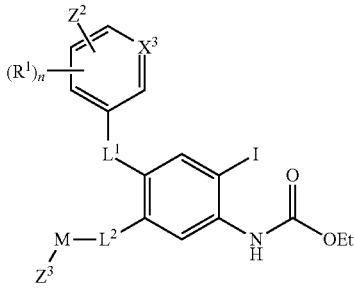

Alkyne 2 can be prepared from the corresponding aminoheterocycle 8, as shown in Scheme 3. Starting material 8 can be converted to bromide 9 by diazotization and substitution with tert-butyl nitrite and copper bromide in one pot. Sonogashira cross coupling of bromide 9 and silylacetylene followed by desilylation gives alkyne 2.

Scheme 3

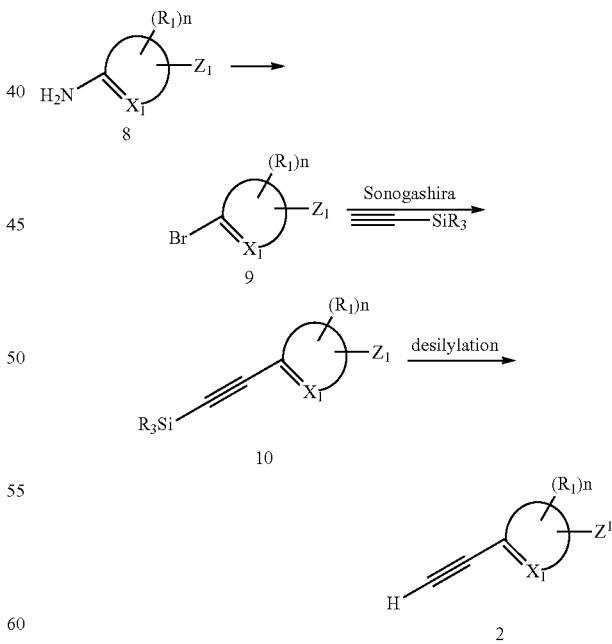

With certain compounds, intermediate 1 can be prepared from the fluoroaniline intermediate 11, as shown in Scheme 4. Nitration of intermediate 11 can be achieved by known methods such as potassium nitrate in trifluoroacetic anhydride. Treatment with a base such as aqueous potassium carbonate frees the amino group to intermediate 12, which upon Sandmeyer transformation yields iodide 13. Displacement of fluoride with a nucleophile such as substituted phenol, hydroxypyridine, thiophenol or pyridine thiophenol under the standard conditions such as potassium carbonate in dimethylformamide leads to intermediate 14. The nitro group in 14 can be reduced with known methods such as iron and aqueous ammonium chloride to intermediate 15, which is protected with a suitable protecting group such as ethyl carbamate to intermediate 1.

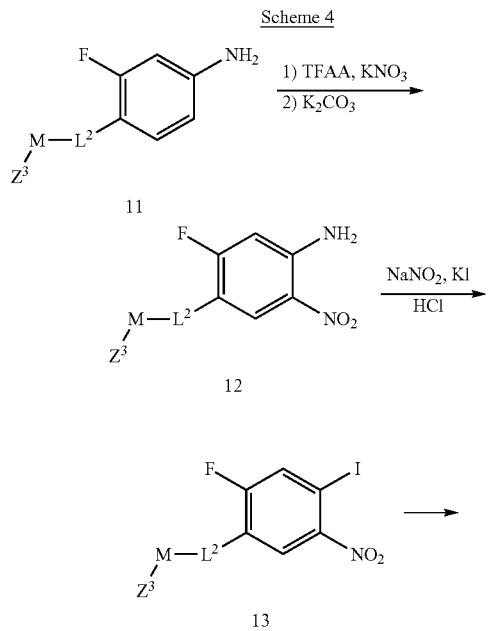

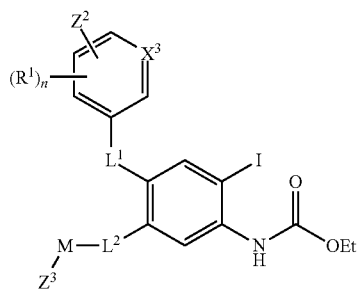

In another embodiment of the invention, intermediate 1a can be prepared from methyl 6-chloro-3-fluoropyridine-2-carboxylate as shown in Scheme 5. Displacement of fluoride with a nucleophile such as substituted phenol, hydroxypyridine, thiophenol or pyridine thiophenol in the presence of a suitable base such as potassium carbonate in a polar solvent such as dimethylformamide gave intermediate 16. Reduction of the ester group with sodium borohydride gave the alcohol intermediate 17, which is transformed to chloride 18 upon treatment with thionyl chloride. Displacement of the alkyl chloride with pyrrolidin-2-one in the presence of a base such as sodium hydride gave intermediate 18. Conversion of the remaining chloride in 19 to amino group in 20 is achieved by coupling to 4-methoxybenzylamine with the aid of a palladium catalyst such as $Pd_2(dba)_3$ and a suitable ligand, followed by acid cleavage of the 4-methoxybenzyl group. Iodination of 20 with iodine and silver sulfate converts it to intermediate 1a.

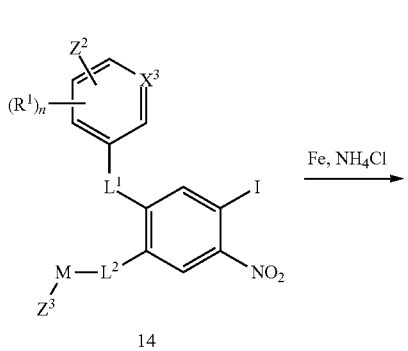

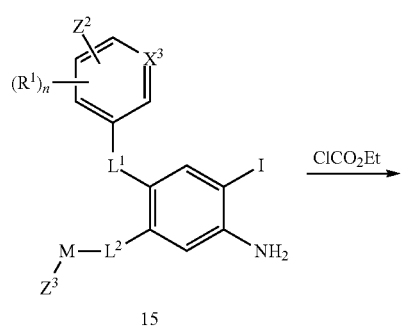

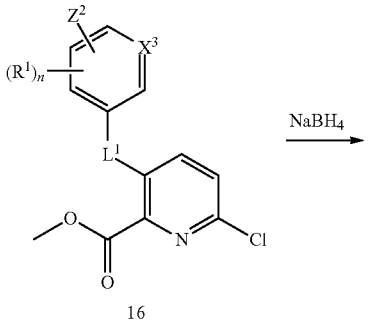

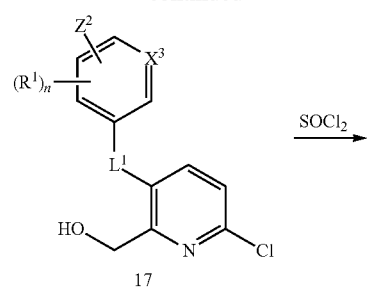

17

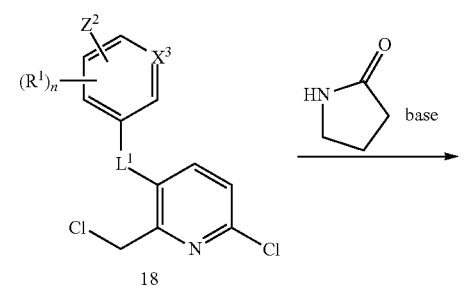

18

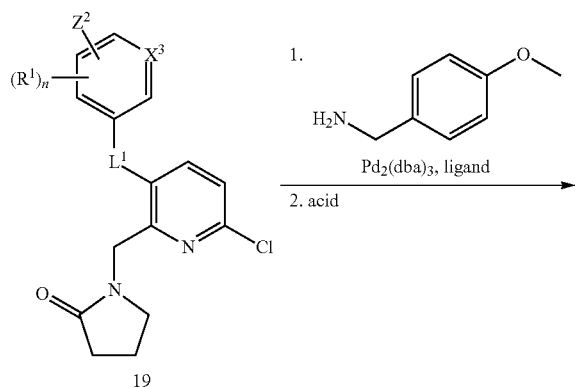

19

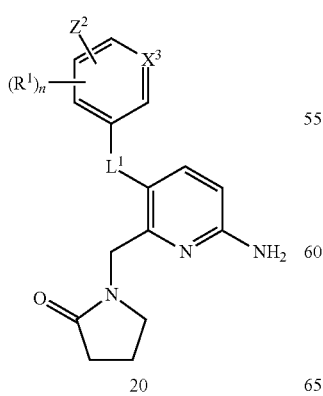

20

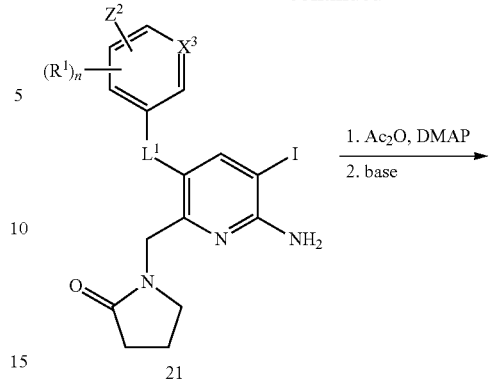

21

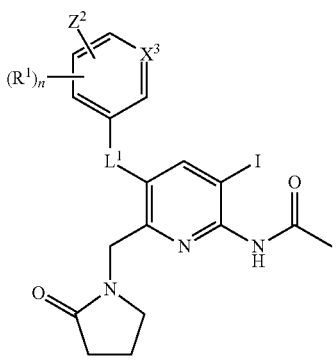

1a

Separation of diastereomers can be carried out at various stages in the preparation of the desired final compounds; however, it is typically carried out on intermediate 4 using supercritical fluid chromatography. Separation of enantiomeric pairs at the ester stage (1a) is achieved by supercritical fluid chromatography using various chiral columns. The absolute configuration is not determined Analytical HPLC Mass Spectrometry Conditions:

LC1: Column: Waters Xterra™ (Waters Technologies Corporation, Wilmington, Del.)
MS C-18, 3.5 μm, 3.0×50 mm
Temperature: 50° C.
Eluent: 10:90 to 98:2 v/v acetonitrile/water+0.05% TFA over 3.75 min.
Flow Rate: 1 0 mL/min, Injection 10 μL
Detection: PDA, 200-600 nm
MS: mass range 150-750 amu; positive ion electrospray ionization LC2: Column: Waters Xterra™ (Waters Technologies Corporation, Wilmington, Del.)
IS C-18, 3.5 μm, 2.1×20 mm
Temperature: 50° C.
Eluent: 5:95 to 95:5 v/v acetonitrile/water+0.05% TFA over 1.75 min.
Flow Rate: 1 5 mL/min, Injection 5 μL
Detection: PDA, 200-600 nm
MS: mass range 150-750 amu; positive ion electrospray ionization LC3: Column: Waters Xterra™ (Waters Technologies Corporation, Wilmington, Del.)
IS C-18, 3.5 μm, 2.1×20 mm
Temperature: 50° C.
Eluent: 5:95 to 95:5 v/v acetonitrile/water+0.05% TFA over 3.00 min.
Flow Rate: 1 5 mL/min, Injection 5 μL Detection: PDA, 200-600 nm
MS: mass range 150-750 amu; positive ion electrospray ionization
LC4: Column: Waters Xterra™ (Waters Technologies Corporation, Wilmington, Del.)
IS C-18, 3.5 µm, 3.0×50 mm
Temperature: 50° C.
Eluent: 10:90 to 98:2 v/v acetonitrile/water+0.05% TFA over 1.25 min.
Flow Rate: 1 5 mL/min, Injection 5 µL
Detection: PDA, 200-600 nm
MS: mass range 150-750 amu; positive ion electrospray ionization
LC5: Column: Sunfire™ (Waters Technologies Corporation, Wilmington, Del.) C-18, 5 µm, 4.6×100 mm
Temperature: 50° C.
Eluent: 10:90 to 98:2 v/v acetonitrile/water+0.1% formic acid over 1.25 min.
Flow Rate: 1 5 mL/min, Injection 5 µL
Detection: PDA, 200-600 nm
MS: mass range 150-750 amu; positive and negative ion electrospray ionization
LC6: Column: Agilent ZORBAX™ (E.I. Du Pont de Nemours and Company, Wilmington, Del.) SB-C18, 3.5 µm, 2.1×50 mm
Temperature: 50° C.
Eluent: 10:90 to 100:0 v/v acetonitrile/water+0.05% TFA over 4.00 min.
Flow Rate: 0 8 mL/min, Injection 1 µL
Detection: PDA, 200-400 nm
MS: mass range 100-1000 amu; positive ion electrospray ionization Preparative Reverse Phase HPLC (RP-HPLC) Conditions:
Column: Xterra™ (Waters Technologies Corporation, Wilmington, Del.) MS, 5 µM, 30×100 mm
Flow Rate: 40 0 mL/min
Eluent: acetonitrile/water+0.1% TFA
Gradient: 10 to 100 v/v acetonitrile/water+0.1% TFA over 20.0 min.
Temperature: ambient
Detection: PDA, 254 nm Preparative thin layer chromatography (PTLC) was performed on 20×20 cm plates (500 µm-1500 µm thick silica gel) using hexanes/ethyl acetate as eluent. Silica gel chromatography was conducted on a Biotage Horizon flash chromatography system using a hexanes/ethyl acetate or DCM/hexanes gradient.

INTERMEDIATES

Intermediate 1

5-(2-CHLORO-5-NITROPHENYL)PYRROLIDIN-2-ONE

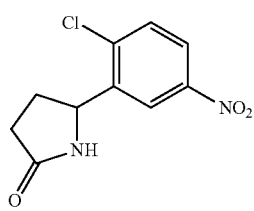 [SMILES: O=C1CCC(c2cc([N+](=O)[O-])ccc2Cl)N1]

Step A: Ethyl 4-(2-chloro-5-nitrophenyl)-4-[(trimethylsilyl)oxy]butanoate

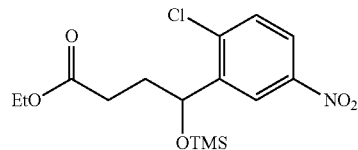

To 2-chloro-5-nitrobenzaldehyde (27.18 g, 146 mmol) in DCM (600 ml) was added 1-ethoxy-1-[(trimethylsilyl)oxy]cyclopropane (54.6 ml, 273 mmol) followed by zinc iodide (7.93 g, 24.84 mmol), and the reaction was stirred at RT until complete by TLC. After 16 hours, the reaction mixture was filtered through Celite™ diatomaceous earth, washed with brine, dried over MgSO4, filtered, and concentrated in vacuo to give ethyl 4-(2-chloro-5-nitrophenyl)-4-[(trimethylsilyl)oxy]butanoate as a crude yellow oil, which was used without further purification.

Step B: 5-(2-chloro-5-nitrophenyl)dihydrofuran-2(3H)-one

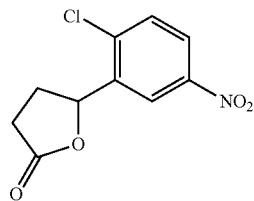 [SMILES: O=C1CCC(c2cc([N+](=O)[O-])ccc2Cl)O1]

The crude oil from Step A was dissolved in DCM (600 ml), to this was added water (8.6 ml, 477 mmol) followed by trifluoroacetic acid (19 ml, 247 mmol). The reaction mixture was stirred at RT. After 16 hours, the reaction mixture was concentrated in vacuo and purified by silica gel chromatography (0-50% EtOAc/hexanes). The resulting orange solid was triturated with ether (150 mL) and dried in vacuo to give product as a yellow solid (35 g, 147 mmol, 100% yield). $^1$H NMR (CDCl3): δ 8.36 (d, J=2.8 Hz, 1 H), 8.16 (dd, J=2.8, 8.8 Hz, 1 H), 7.59 (d, J=8.8 Hz, 1 H), 5.81 (t, J=7.6 Hz, 1 H), 2.97-2.90 (m, 1 H), 2.73-2.68 (m, 2 H), 2.13-2.07 (m, 1 H).

Step C: Methyl 4-azido-4-(2-chloro-5-nitrophenyl)butanoate

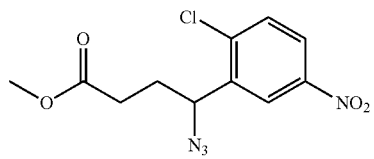 [SMILES: COC(=O)CCC(N=[N+]=[N-])c1cc([N+](=O)[O-])ccc1Cl]

To the product of Step B (35 g, 147 mmol) in MeOH (500 ml) was added DBU (4.47 ml, 29.6 mmol) and the reaction was stirred at RT. After 16 hours, the reaction was quenched with 1N HCl (100 mL) and concentrated in vacuo. The residue was diluted with EtOAc, washed with water and brine, dried over MgSO4, filtered, concentrated in vacuo, and purified by silica gel chromatography (0-40% EtOAc-hexanes) to give methyl 4-(2-chloro-5-nitrophenyl)-4-hydroxybutanoate (35.76 g, 131 mmol, 88% yield) as a light yellow solid.

The alcohol product was dissolved in THF (400 ml), triphenylphosphine (44.3 g, 169 mmol) was added, and the mixture was cooled to 0° C. Diphenyl phosphorylazide (31.3 ml, 145 mmol) was then added followed by dropwise addition of diethyl azodicarboxylate (22.91 ml, 145 mmol). The reaction was then allowed to warm to RT slowly and stirred overnight. The mixture was concentrated in vacuo and purified by silica gel chromatography (12% EtOAc/hexanes) to give methyl 4-azido-4-(2-chloro-5-nitrophenyl)butanoate as a yellow oil (26.06 g, 87 mmol, 72.4% yield). $^1$H NMR (CDCl3): δ 8.35 (d, J=2.8 Hz, 1 H), 8.14 (dd, J=2.8, 8.8 Hz, 1 H), 7.59 (d, J=8.8 Hz, 1 H), 5.81 (dd, J=4.8, 8.8 Hz, 1 H), 3.69 (s, 3 H), 2.54-2.46 (m, 2 H), 2.18-2.04 (m, 2 H).

Step D: 5-(2-Chloro-5-nitrophenyl)pyrrolidin-2-one

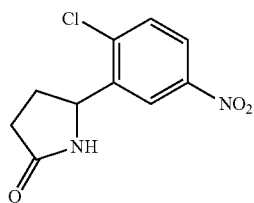 [SMILES: O=C1CCC(c2cc([N+](=O)[O-])ccc2Cl)N1]

To the product of Step C (24 g, 80 mmol) in DMF (402 ml) was added triphenylphosphine (25.3 g, 96 mmol) and the reaction was heated at 90° C. for 2 hours. After gas evolution ceased, the reaction was quenched with 200 mL of water and the mixture was heated at 90° C. for an additional 16 hours. After cooling to RT, the reaction was diluted with water, and extracted with EtOAc. The combined organic phase was concentrated in vacuo, and the resulting solid was triturated with 200 mL of hot EtOAc. The solid was collected by filtration, washed with EtOAc, and dried in vacuo to give Intermediate 1 as a tan solid (9.36 g, 38.9 mmol, 48.4% yield). $^1$H NMR (DMSO-d6): δ 8.25 (d, J=2.8 Hz, 1 H), 8.15 (dd, J=2.8, 8.4 Hz, 1 H), 7.79 (d, J=8.4 Hz, 1 H), 5.81 (dd, J=5.6, 8.4 Hz, 1 H), 2.67-2.58 (m, 1 H), 2.25 (t, J=8.4 Hz, 2 H), 1.78-1.69 (m, 1 H).

Intermediate 2

5-(2-CHLORO-5-NITROPHENYL)-1-METHYL-PYRROLIDIN-2-ONE

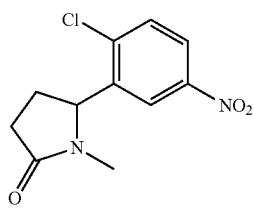 [SMILES: CN1C(=O)CCC1c1cc([N+](=O)[O-])ccc1Cl]

To sodium hydride (0.73 g, 18.3 mmol) in DMF (50 ml) at 0° C. was added Intermediate 1 (3.66 g, 15.2 mmol) in THF (50 ml). After 10 minutes, iodomethane (1.14 ml, 18.3 mmol) was added and the mixture allowed warming to RT. After one hour, the reaction mixture was diluted with water, and extracted with EtOAc. The organic phase was washed with water and brine, dried over MgSO$_4$, filtered and concentrated in vacuo. Purification by silica gel chromatography (5-75% EtOAc-hexanes) yielded Intermediate 2 as a tan solid (3.2 g, 12.57 mmol, 83% yield). $^1$H NMR (CDCl$_3$): δ 8.14 (dd, J=2.8, 8.8 Hz, 1 H), 7.96 (d, J=2.8 Hz, 1 H), 7.61 (d, J=8.8 Hz, 1 H), 5.04 (dd, J=4.6, 8.6 Hz, 1 H), 2.79 (s, 3 H), 2.70-2.43 (m, 3 H), 1.88-1.80 (m, 1 H). MS (ES$^+$) m/z: 255 (M+H).

Intermediate 3

METHYL 3-(6-ETHYNYLPYRIDIN-3-YL)PROPANOATE

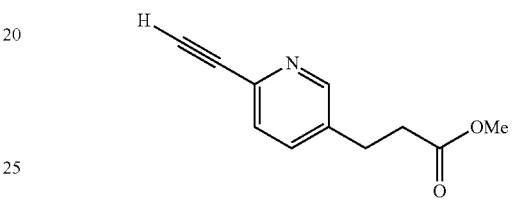

Step A: Methyl(2E)-3-(6-bromopyridin-3-yl)prop-2-enoate

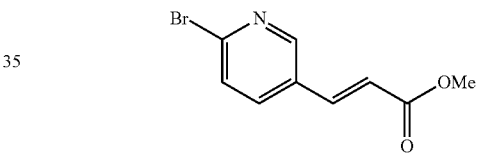

To a suspension of sodium hydride (4.69 g, 108 mmol) in diethyl ether (100 ml) at 0° C. was added a solution of methyl diethylphosphonoacetate (22.60 g, 108 mmol) in diethyl ether (50 ml). The cooling bath was removed, and after 10 min a solution of 6-bromopyridine-3-carbaldehyde (10 g, 53.8 mmol) in THF/diethyl ether (200 ml) was added over 20 min, and the mixture was allowed to stir at room temperature for 1 hour. Product precipitated out from the reaction mixture with the addition of ether. The solid was collected by filtration, and the process was repeated three times to give methyl(2E)-3-(6-bromopyridin-3-yl)prop-2-enoate as a white solid (8.5 g, 35.1 mmol, 65.3% yield). $^1$H NMR (500 MHz, CDCl$_3$): δ 8.48 (d, J=2.4 Hz, 1 H); 7.69 (dd, J=8.3, 2.5 Hz, 1 H); 7.62 (d, J=16.1 Hz, 1 H); 7.52 (d, J=8.3 Hz, 1 H); 6.50 (d, J=16.1 Hz, 1 H); 3.82 (s, 3 H). MS (ES$^+$) m/z: 244 (M+H). 1.22 min on LC1.

Step B: Methyl 3-(6-bromopyridin-3-yl)propanoate

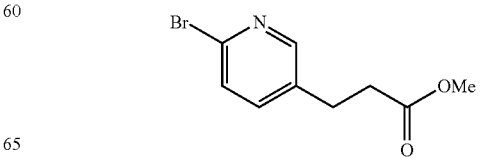

To a slurry of methyl(2E)-3-(6-bromopyridin-3-yl)prop-2-enoate (8.1 g, 33.5 mmol) and nickel (II) chloride (3.25 g, 25.10 mmol) in methanol (160 mL) at 0° C. was added sodium borohydride (3.80 g, 100 mmol) portionwise. The reaction mixture turned black, and starting material was fully consumed 20 minutes after the final nickel chloride addition. The reaction mixture was diluted with ethyl acetate, washed with aqueous sodium bicarbonate and brine. The organic layers were dried over sodium sulfate, filtered, and concentrated to a yellow oil. Purification via silica gel column chromatography (20% EtOAc/hexanes) gave methyl 3-(6-bromopyridin-3-yl)propanoate (2.1 g, 8.60 mmol, 25.7% yield). $^1$H NMR (500 MHz, CDCl$_3$): δ 8.23 (s, 1 H); 7.40 (s, 2 H); 3.66 (s, 3 H); 2.92 (t, J=7.5 Hz, 2 H); 2.62 (t, J=7.5 Hz, 2 H). MS (ES$^+$) m/z: 246 (M+H).

Step C: Methyl 3-{6-1[(trimethylsilyl)ethynyl]pyridin-3-yl}propanoate

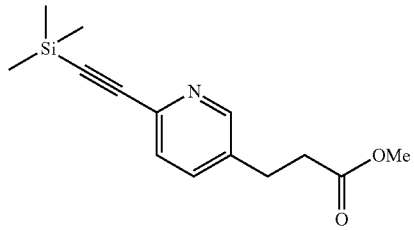 [SMILES: COC(=O)CCc1ccc(C#C[Si](C)(C)C)nc1]

To a degassed mixture of bis(triphenylphosphine)palladium(II) chloride (0.575 g, 0.819 mmol), copper iodide (0.312 g, 1.639 mmol), triethylamine (7 ml, 50.2 mmol), and methyl 3-(6-bromopyridin-3-yl)propanoate (2.0 g, 8.19 mmol) in THF (20 mL) was added trimethylsilyl acetylene (0.966 g, 9.83 mmol) in THF (5 mL). After addition, the reaction was allowed to stir at 50° C. overnight. The reaction mixture was concentrated in vacuo and loaded directly onto a silica gel column, eluting with 20% EtOAc/hexanes to give methyl 3-{6-[(trimethylsilyl)ethynyl]pyridin-3-yl}propanoate (2.1 g, 8.03 mmol, 98% yield). $^1$H NMR (500 MHz, CD3 OD): δ 8.36 (s, 1 H); 7.70 (dd, J=8.1, 2.2 Hz, 1 H); 7.50 (d, J=8.0 Hz, 1 H); 3.63 (s, 3 H); 2.97-2.94 (m, 2 H); 2.69-2.66 (m, 2 H); 0.25 (s, 9 H). MS (ES$^+$) m/z: 262 (M+H)$^+$.

Step D: Methyl 3-(6-ethynylpyridin-3-yl)propanoate

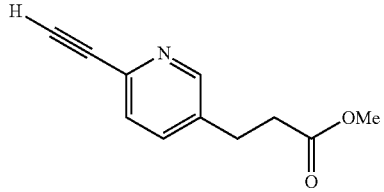 [SMILES: C#Cc1ccc(CCC(=O)OC)cn1]

To a solution of methyl 3-{6-[(trimethylsilyl)ethynyl]pyridin-3-yl}-propanoate in THF/MeOH (1:1, 4 mL) at room temperature was added potassium carbonate (190 mg, 1.38 mmol). The reaction mixture was stirred for 1 hour at room temperature, and then quenched with 5% citric acid. The mixture was extracted with EtOAc, and the organic layer was washed with brine, dried over Na$_2$SO$_4$, filtered, and concentrated in vacuo. Purification by preparative TLC using 20% EtOAc/hexanes gave methyl 3-(6-ethynylpyridin-3-yl)propanoate (55 mg, 0.291 mmol, 84% yield). $^1$H NMR (500 MHz, CD3 OD): δ 8.38 (d, J=2.1 Hz, 1 H); 7.71 (dd, J=8.1, 2.2 Hz, 1 H); 7.49 (d, J=8.0 Hz, 1 H); 3.74 (s, 1 H); 3.67 (s, 3 H); 3.03-2.96 (m, 2 H); 2.74-2.67 (m, 2 H). MS (ES$^+$) m/z: 190 (M+H)$^+$.

Intermediate 4

METHYL 3-(6-ETHYNYLPYRIDIN-3-YL)-2,2-DIMETHYLPROPANOATE

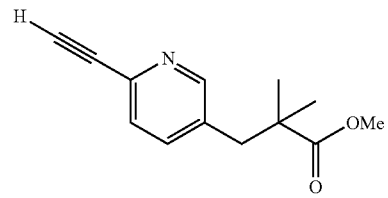 [SMILES: C#Cc1ccc(CC(C)(C)C(=O)OC)cn1]

Step A: Methyl 2,2-dimethyl-3-{6-[(trimethylsilyl)ethynyl]pyridin-3-yl}propanoate

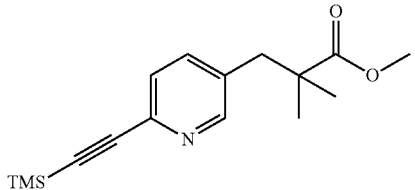 [SMILES: COC(=O)C(C)(C)Cc1ccc(C#C[Si](C)(C)C)nc1]

To a solution of methyl 3-{6-[(trimethylsilyl)ethynyl]pyridin-3-yl}-propanoate (product of Step C in the procedure of intermediate 3, 240 mg, 0.87 mmol) in THF (4 mL) at −78° C. was added LiHMDS (1 M, 1.92 mL, 1.92 mmol) in THF. After stirring for 1 hour, (0.16 mL, 2.6 mmol) was added and the reaction was allowed to warm to room temperature slowly. The reaction was quenched with aqueous ammonium chloride and extracted with ethyl acetate. The organic layer was washed with water and brine, dried over Na$_2$SO$_4$ and concentrated. Purification by silica gel chromatography (20% EtOAc/hexanes) gave methyl 2,2-dimethyl-3-{6-[(trimethylsilyl)ethynyl]pyridin-3-yl}-propanoate as a gray solid (50 mg, 0.16 mmol, 19% yield). $^1$H NMR (500 MHz, CDCl$_3$): δ 8.34 (s, 1 H); 7.41-7.35 (m, 2 H); 3.65 (s, 3 H); 2.84 (s, 2 H); 1.18 (s, 6 H); 0.26 (s, 9 H). MS (ES$^+$) m/z: 304 (M+H)$^+$.

Step B: Methyl 3-(6-ethynylpyridin-3-yl)-2,2-dimethylpropanoate

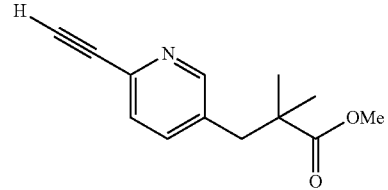 [SMILES: C#Cc1ccc(CC(C)(C)C(=O)OC)cn1]

Prepared from the product of Step A using the same method as described in Step D of Intermediated 3. MS (ES⁻) m/z: 233.17 (M+H).

Intermediate 5

METHYL[(6-ETHYNYLPYRIDIN-3-YL)OXY]ACETATE

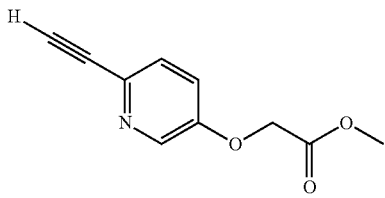

Step A: Methyl[(6-bromopyridin-3-yl)oxy]acetate

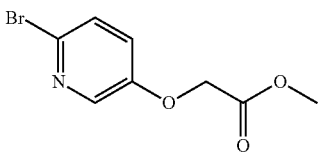

To a mixture of 6-bromopyridin-3-ol (500 mg, 2.87 mmol) and potassium carbonate (1.19 g, 8.62 mmol) in THF (12 ml) at room temperature was slowly added methyl chloroacetate (624 mg, 5.75 mmol). The resulting reaction mixture was heated to 60° C. overnight. The reaction mixture was cooled to room temperature, quenched with sodium bicarbonate and extracted with EtOAc. The organic layer was washed with water and brine, dried over Na₂SO₄, filtered, and concentrated in vacuo to give methyl[(6-bromopyridin-3-yl)oxy]acetate (550 mg, 2.24 mmol, 78% yield). ¹H NMR (500 MHz, CDCl₃): δ 8.07 (d, J=3.1 Hz, 1 H); 7.39 (d, J=8.7 Hz, 1 H); 7.14-7.08 (m, 1 H); 4.66 (s, 3 H); 3.83 (s, 2 H). MS (ES⁻) m/z: 247 (M+H)⁺.

Step B: Methyl({6-[(tripropan-2-ylsilyl)ethynyl]pyridin-3-yl}oxy)acetate

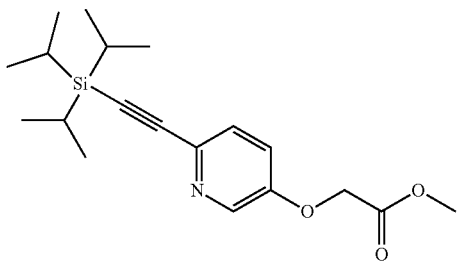 [SMILES: COC(=O)COc1ccc(C#C[Si](C(C)C)(C(C)C)C(C)C)nc1]

To a degassed mixture of the product of Step A (500 mg, 2.07 mmol), bis(triphenylphosphine)palladium(II) chloride (145 mg, 0.21 mmol), copper iodide (79 mg, 0.41 mmol) and triethylamine (2.0 ml, 14.51 mmol) in THF (8 mL) at room temperature was added (triisopropylsilyl)acetylene (454 mg, 2.49 mmol) dropwise, and the resulting reaction mixture was stirred at 50° C. overnight. The reaction mixture was concentrated in vacuo, and purified by silica gel chromatography (20% EtOAc/hexanes) to give the desired product as a dark solid (715 mg, 2.06 mmol, 99% yield). MS (ES⁺) m/z: 348 (M+H).

Step C: Methyl[(6-ethynylpyridin-3-yl)oxy]acetate

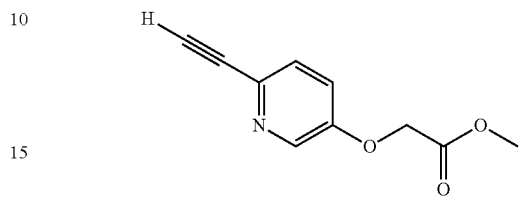

To a solution of the product of Step B (715 mg, 2.06 mmol) in acetonitrile (8 ml) was added acetic acid (0.12 ml, 2.06 mmol). The reaction mixture was cooled to −10° C. and TBAF (1M, 2.2 ml, 2.2 mmol) was added. The reaction mixture was allowed to warm to room temperature and stirred for an additional 1 hour. It was then concentrated and purified by silica gel chromatography (40% EtOAc/hexanes) to give methyl[(6-ethynylpyridin-3-yl)oxy]acetate as a white solid (340 mg, 1.78 mmol, 86% yield). MS (ES⁺) m/z: 192 (M+H).

Intermediate 6

ETHYL(5-CHLORO-2-ETHYNYL-1,3-THIAZOL-4-YL)ACETATE

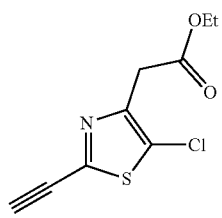

Step A.
Ethyl(2-amino-5-chloro-1,3-thiazol-4-yl)acetate

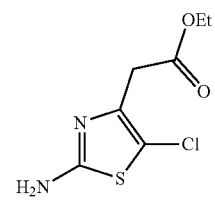

To ethyl 2-aminothiazole-4-acetate (5.48 g, 29.4 mmol) in acetic acid (300 ml) was added NCS (4.32 g, 32.4 mmol) at room temperature. The reaction mixture was stirred for 2 h and it was concentrated to a red residue. Solids were formed and the mixture was suspended in acetone/diethyl ether (1:1, 20 mL) and stirred overnight. The solids were collected by filtration and washed with acetone/diethyl ether (1:1, 50 mL) to give ethyl 2-amino-5-chlorothiazole-4-acetate (3.24 g, 14.68 mmol, 49.9% yield) as a brick-red solid.

Step B.
Ethyl(2-bromo-5-chloro-1,3-thiazol-4-yl)acetate

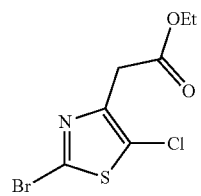 [SMILES: CCOC(=O)Cc1nc(Br)sc1Cl]

To a solution of ethyl(2-amino-5-chloro-1,3-thiazol-4-yl)acetate (2 g, 9.06 mmol) and copper(I) bromide (1.3 g, 9.06 mmol) in acetonitrile (20 ml) under nitrogen was added tert-butyl nitrite (1.4 ml, 11.78 mmol), and the mixture was stirred at 60° C. for 2 h. It was cooled to room temperature and concentrated in vacuo. The residue was partitioned between ethyl acetate and aqueous 1 N HCl solution. The organic phase was washed with brine, dried over sodium sulfate and concentrated. The crude residue was purified by silica gel chromatography (0-20% EtOAc/hexanes) to give ethyl 2-bromo-5-chlorothiazole-4-acetate (908 mg, 3.19 mmol, 35% yield). MS (ES+) m/z: 283 (M+H)+, 285 (M+H+2)+, 287 (M+H+4)+.

Step C. Ethyl{5-chloro-2-[(tripropan-2-ylsilyl)ethynyl]-1,3-thiazol-4-yl}acetate

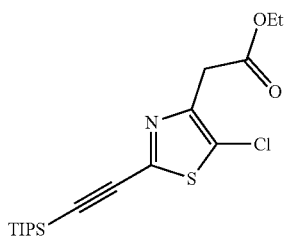

To a mixture of ethyl(2-bromo-5-chloro-1,3-thiazol-4-yl)acetate (470 mg, 1.65 mmol), CuI (31.5 mg, 0.16 mmol), and PdCl$_2$(PPh$_3$)$_2$ (58 mg, 0.08 mmol) were added anhydrous THF (10 mL) and TEA (3 mL). The reaction mixture was degassed by bubbling nitrogen for 15 min and heated to 55° C. A THF (5 mL) solution of (triisopropylsilyl)acetylene (361 mg, 1.982 mmol) was added in over 10 min. After 1 h, the reaction mixture was partitioned between EtOAc and brine. The organic layer was dried over sodium sulfate, filtrated and concentrated. The crude residue was purified by silica gel chromatography (0-20% EtOAc/hexanes) to give ethyl{5-chloro-2-[(tripropan-2-ylsilyl)ethynyl]-1,3-thiazol-4-yl}acetate (476 mg, 1.23 mmol, 75% yield) as a clear oil.

Step D.
Ethyl(5-chloro-2-ethynyl-1,3-thiazol-4-yl)acetate

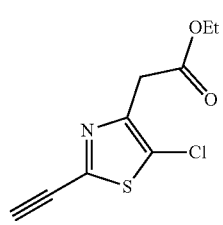

The title compound was prepared from the product of Step C using the method described for step C of intermediate 5. MS (ES+) m/z: 230 (M+H)+, 232 (M+H+2)+.

Intermediate 7

METHYL 3-(2-ETHYNYL-1,3-THIAZOL-5-YL)PROPANOATE

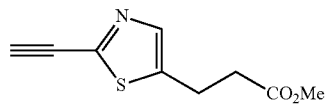

Step A. Methyl 3-(2-amino-1,3-thiazol-5-yl)propanoate

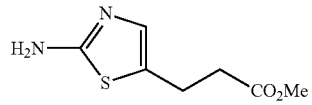

Methyl 5-bromo-4-oxopentanoate (*Synthesis* 2007, 23, 3731-3735) (3.64 g, 17.41 mmol) and thiourea (1.33 g, 17.41 mmol) in ethanol were heated to reflux overnight. The reaction mixture was cooled to room temperature, and the white crystals were collected by filtration. The solid was washed with cold ethanol (5 mL×2), ethyl acetate (10 mL) and diethyl ether (20 mL) in the order given, then dried in vacuo to give methyl 3-(2-amino-1,3-thiazol-5-yl)propanoate as the HBr salt (4.2 g, 90%). MS (ES+) m/z: 187 (M+H)+.

Step B. Methyl 3-(2-bromo-1,3-thiazol-5-yl)propanoate

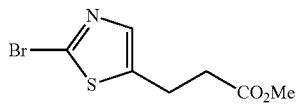

To a mixture of methyl 3-(2-amino-1,3-thiazol-5-yl)propanoate (2.6 g, 9.25 mmol) and CuBr (1.33 g, 9.25 mmol) in acetonitrile (40 ml) at 50° C. was added tert-butyl nitrite (1.43 ml, 12.02 mmol) slowly. After 1 h, the reaction mixture was cooled to room temperature and partitioned between EtOAc and saturated aqueous NH$_4$Cl. The organic layer was washed with brine, dried over sodium sulfate, filtered and concentrated. The crude residue was purified by silica gel chromatography (0-50% EtOAc/hexanes) to give methyl 3-(2-bromo-1,3-thiazol-5-yl)propanoate (850 mg, 36%). MS (ES+) m/z: 249.87 (M+H)−, 251.85 (M+H+2)+.

Step C. Methyl 3-(2-ethynyl-1,3-thiazol-5-yl)propanoate

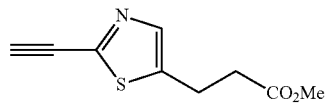

The title compound was prepared from the product of Step B using the methods described for step C and D of intermediate 5. MS (ES+) m/z: 196.07 (M+H)+.

Intermediate 8

DIETHYL[(2-ETHYNYL-1,3-THIAZOL-5-YL)METHYL]PHOSPHONATE

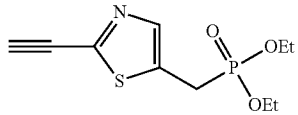 [SMILES: C#Cc1ncc(CP(=O)(OCC)OCC)s1]

Step A. Ethyl 2-[(tert-butoxycarbonyl)amino]-1,3-thiazole-5-carboxylate

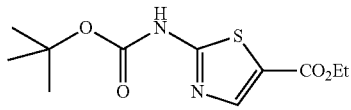 [SMILES: CCOC(=O)c1cnc(NC(=O)OC(C)(C)C)s1]

A mixture of ethyl 2-amino-1,3-thiazole-5-carboxylate (4.33 g, 25 1 mmol), (Boc)₂O (6.13 ml, 26.4 mmol) and DMAP (0.061 g, 0.50 mmol) in THF (50 ml) was stirred for 16 h. White solid resulted, and it was collected by filtration and washed with ethyl acetate to give ethyl 2-[(tert-butoxycarbonyl)amino]-1,3-thiazole-5-carboxylate (5.46 g, 20.12 mmol, 80% yield) as a pale white solid. MS (ES⁻) m/z: 271.10 [M−1]⁻.

Step B. Tert-butyl[5-(hydroxymethyl)-1,3-thiazol-2-yl]carbamate

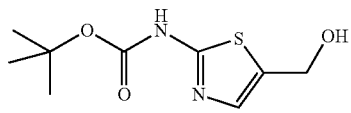

To a 500 mL flask was charged with a magnetic stirring bar, ethyl 2-[(tert-butoxycarbonyl)amino]-1,3-thiazole-5-carboxylate (5.46 g, 20.12 mmol) and anhydrous THF (100 ml). The solution was cooled to 0° C. and LiAlH₄ in diethyl ether (1M, 24.2 ml, 24.2 mmol) was added in slowly. The mixture was stirred for 20 min before it was allowed to warm to room temperature. After 2 h, it was cooled to 0° C. and quenched carefully with water (1 mL), and 15% aqueous NaOH (3 mL). The mixture was stirred vigorously for 2 h, and the white precipitates were removed by filtration through Celite™ diatomaceous earth. To the filtrate was added about 15 g of silica gel and the mixture was concentrated in vacuo. The silica gel was dried and loaded onto a pre-packed cartridge, and eluted with 0-100% EtOAc/hexanes to give tert-butyl[5-(hydroxymethyl)-1,3-thiazol-2-yl]carbamate (2.9 g, 12.59 mmol, 63% yield) as a white solid. ¹H NMR (500 MHz, DMSO-d₆): δ 11.28 (s, 1H), 7.18 (s, 1H), 5.32 (t, J=6 Hz, 1H), 4.55 (d, J=6 Hz, 2H), 1.49 (s, 9H). MS (ES+) m/z: 230.9 (M+H)+.

Step C. Tert-butyl[5-(chloromethyl)-1,3-thiazol-2-yl]carbamate

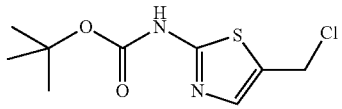

Thionyl chloride (3.68 ml, 50.4 mmol) was added to the suspension of tert-butyl[5-(hydroxymethyl)-1,3-thiazol-2-yl]carbamate (2.9 g, 12.59 mmol) in DCM (10 ml) at 0° C. The reaction mixture was stirred for 1 h before it was concentrated in vacuo. The residue was used in the next step without further purification. ¹H NMR (500 MHz, DMSO-d₆): δ 7.41 (s, 1H), 5.01 (s, 2H), 1.50 (s, 9H).

Step D. Diethyl({2-[(tert-butoxycarbonyl)amino]-1,3-thiazol-5-yl}methyl)phosphonate

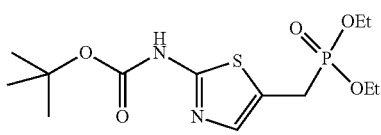 [SMILES: CCOP(=O)(Cc1cnc(NC(=O)OC(C)(C)C)s1)OCC]

To a 250 mL flask was charged a magnetic stirring bar, tert-butyl[5-(chloromethyl)-1,3-thiazol-2-yl]carbamate (3.13 g, 12.58 mmol), anhydrous THF (60 ml) and triethyl phosphite (17.52 ml, 101 mmol). The reaction mixture was refluxed for 16 h. It was concentrated after cooling to room temperature, and the crude residue was purified by silica gel chromatography (0-100% EtOAc/hexanes) to give diethyl ({2-[(tert-butoxycarbonyl)amino]-1,3-thiazol-5-yl}methyl)phosphonate (4.28 g, 12.22 mmol, 97% yield) as a colorless oil. MS (ES+) m/z: 350.18 (M+H)+.

Step E. Diethyl[(2-amino-1,3-thiazol-5-yl)methyl]phosphonate

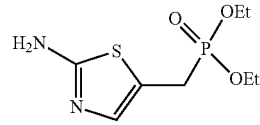

To a solution of diethyl({2-[(tert-butoxycarbonyl)amino]-1,3-thiazol-5-yl}methyl)phosphonate (4.23 g, 12.07 mmol) in DCM (45 ml) was added TFA (25 ml, 324 mmol) and the mixture was stirred for 2 h at rt. It was concentrated and partitioned between DCM and aqueous sodium bicarbonate. The organic layer was washed with brine, dried over sodium sulfate and concentrated. The crude residue was purified by silica gel chromatography (0-8% MeOH/DCM) to give diethyl[(2-amino-1,3-thiazol-5-yl)methyl]phosphonate (1.35 g, 5.39 mmol, 44.7% yield) as white crystals. MS (ES+) m/z: 250.96 (M+H)+.

Step F. Diethyl[(2-bromo-1,3-thiazol-5-yl)methyl]phosphonate

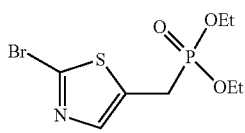

To a solution of diethyl[(2-amino-1,3-thiazol-5-yl)methyl]phosphonate (910 mg, 3.64 mmol) and CuBr$_2$ (812 mg, 3.64 mmol) in acetonitrile (20 ml) at room temperature was added tert-Butyl nitrite (0.65 ml, 5.45 mmol). After 1.5 h, it was diluted with ethyl acetate and washed with brine three times. The organic layer was dried over sodium sulfate and concentrated. The crude residue was purified by silica gel chromatography (0-100% EtOAc/hexanes) to give diethyl[(2-bromo-1,3-thiazol-5-yl)methyl]phosphonate (906 mg, 2.88 mmol, 79% yield) as a colorless oil. $^1$H NMR (500 MHz, CDCl$_3$): δ 7.40 (s, 1H), 4.10 (m, 4H), 3.18 (d, J=20 Hz, 2H), 1.30 (t, J=7.0 Hz, 6H). MS (ES$^+$) m/z: 313.76 (M+H)$^+$, 315.73 (M+H+2)$^+$.

Step G. Diethyl[(2-ethynyl-1,3-thiazol-5-yl)methyl]phosphonate

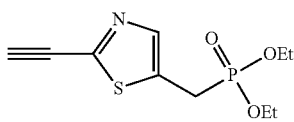

The title compound was prepared from the product of Step F using the methods described for Step C and D of intermediate 5. MS (ES$^+$) m/z: 259.97 (M+H)$^+$.

EXAMPLES

Example 1

METHYL 3-(6-{5-[4-(ETHYLSULFONYL)PHENOXY]-6-(1-METHYL-5-OXOPYRROLIDIN-2-YL)-1H-INDOL-2-YL}PYRIDIN-3-YL)PROPANOATE

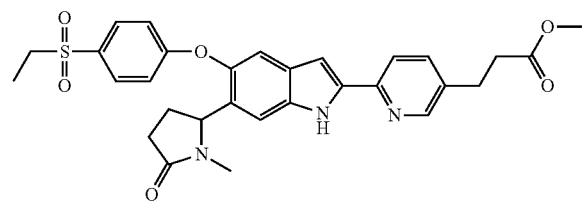 [SMILES: CCS(=O)(=O)c1ccc(Oc2cc3cc(-c4ccc(CCC(=O)OC)cn4)[nH]c3cc2C2CCC(=O)N2C)cc1]

Step A: 4-(ethylsulfonyl)phenol

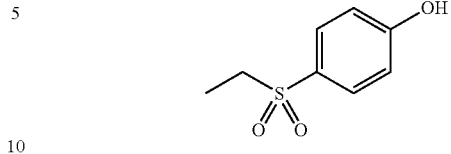

To a slurry of sodium hydride (1.255 g, 31.4 mmol) in THF (50 mL) at 0° C. was added dropwise a solution of pOMe-thiophenol (3.51 ml, 28.5 mmol) in THF (50 mL). The solution was allowed to warm to RT and EtBr (4.26 ml, 57.1 mmol) was added. Stirred at RT overnight. The reaction mixture was concentrated in vacuo and purified by column chromatography (0-15% EtOAc/hexanes, RediSep-40 gram) to give ethyl(4-methoxyphenyl)sulfane (4.8 g, 28.5 mmol, 100% yield).

To give ethyl(4-methoxyphenyl)sulfane (4.24 g, 25.2 mmol) in DCM (120 ml) at 0° C. was added mCPBA (12.42 g, 55.4 mmol) in portions and the reaction stirred 0° C. to RT until complete. Diluted reaction with 50% sat NaHCO3. Extracted aqueous with DCM, washed combined orgs with 50% sat NaHCO3 and brine, dried over Mg504, filtered, and concentrated in vacuo to give 1-(ethylsulfonyl)-4-methoxybenzene (5 g, 24.97 mmol, 99% yield) as a clear oil.

To 1-(ethylsulfonyl)-4-methoxybenzene (1 g, 4.99 mmol) in DCM (30 ml) at 0° C. was added boron tribromide (1.0 M in DCM, 10 ml, 10 mmol) dropwise in DCM (10 ml) and the reaction stirred 0° C. to RT. Heated to reflux for 1 h. Another 5 ml of BBr3 solution was added and the mixture was heated to reflux overnight. It was cooled to rt and quenched with 50% sat NaHCO3, extracted with DCM, washed combined organic layers with brine, dried, filtered, concentrated, and purified by column chromatography (5-50% EtOAc/hexanes, RediSep-24 gram) to give the titled compound (600 mg, 3.22 mmol, 64.5% yield) as a colorless oil. $^1$H NMR (CDCl$_3$): δ 7.74 (dd, J=2.0, 6.8 Hz, 2 H), 6.98 (dd, J=2.0, 6.8 Hz, 2 H), 3.12 (q, J=7.6 Hz, 2 H), 1.26 (t, J=7.6 Hz, 3 H).

Step B: 5-{2-[4-(ethylsulfonyl)phenoxy]-5-nitrophenyl}-1-methylpyrrolidin-2-one

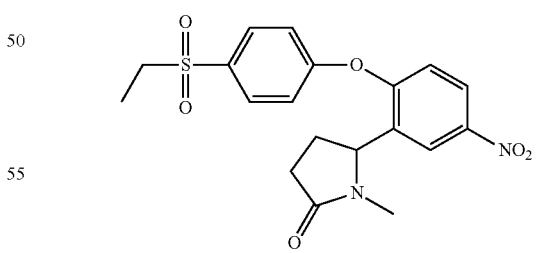

To Intermediate 2 (1.21 g, 6.48 mmol) in DMF (25 ml) was added K$_2$CO$_3$ (1.38 g, 9.97 mmol) followed by 4-(ethylsulfonyl)phenol (1.27 g, 4.99 mmol) and the mixture was heated at 120° C. for 6 h. It was cooled to RT, and partitioned between water and EtOAc. The organic phase was washed with brine, dried over MgSO$_4$, filtered, and concentrated in vacuo. The crude residue was purified by silica gel chromatography (25-100% EtOAc/hexanes) to give 5-{2-[4-(ethylsulfonyl)phenoxy]-5-nitrophenyl}-1-methylpyrrolidin-2-one (1.75 g, 4.33 mmol, 87% yield) as a light yellow solid. ¹H NMR (CDCl₃): δ 8.19 (dd, J=2.8, 8.8 Hz, 1 H), 8.12 (d, J=2.8 Hz, 1 H), 7.98 (dd, J=2.0, 6.8 Hz, 2 H), 7.20 (dd, J=2.0, 6.8 Hz, 2 H), 7.02 (d, J=8.8 Hz, 1 H), 4.98 (dd, J=4.8, 8.4 Hz, 1 H), 3.15 (q, J=7.6 Hz, 2 H), 2.79 (s, 3 H), 2.62-2.42 (m, 3H), 1.95-1.90 (m, 1 H), 1.34 (t, J=7.6 Hz, 3 H). MS (ES⁺) m/z: 405 (M+H).

Step C. 5-{5-amino-2-[4-(ethylsulfonyl)phenoxy]-4-iodophenyl}-1-methylpyrrolidin-2-one

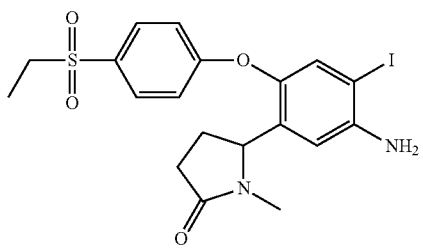 [SMILES: CCS(=O)(=O)c1ccc(Oc2cc(I)c(N)cc2C2CCC(=O)N2C)cc1]

To the product from Step A (1.75 g, 4.33 mmol) in THF (12 ml), MeOH (6.00 ml), saturated NH₄Cl solution (3 ml), and water (3 ml) was added iron (1 g, 17.91 mmol) in portions and the reaction heated at 100° C. for 1 hour. The reaction was cooled to RT, diluted with MeOH, and filtered through Celite™ diatomaceous earth. The filter cake was washed with MeOH, and the combined filtrate was concentrated in vacuo to give 5-{5-amino-2-[4-(ethylsulfonyl)-phenoxy]phenyl}-1-methylpyrrolidin-2-one (1.62 g, 4.33 mmol, 100% yield) as a brown solid. MS (ES⁺) m/z: 375 (M+H).

To a solution of the aniline product in MeOH (15 ml), dioxane (12 ml) and water (12 ml), were added potassium iodide (0.72 g, 4.33 mmol) and potassium iodate (0.46 g, 2.16 mmol). The reaction was purged with nitrogen, and concentrated HCl (1.586 ml, 9.52 mmol) was added. The resulting mixture was heated at 50° C. for 90 minutes. The reaction was then cooled down, and partitioned between DCM and saturated sodium bicarbonate solution. The organic phase was washed with brine, dried over MgSO₄, and concentrated in vacuo to give 5-{5-amino-2-[4-(ethyl-sulfonyl)-phenoxy]-4-iodophenyl}-1-methylpyrrolidin-2-one (2 g, 4 0 mmol, 92% yield) as a black oil. MS (ES⁺) m/z: 501 (M+H).

Step D. Ethyl{4-[4-(ethylsulfonyl)phenoxy]-2-iodo-5-(1-methyl-5-oxopyrrolidin-2-yl)phenyl}carbamate

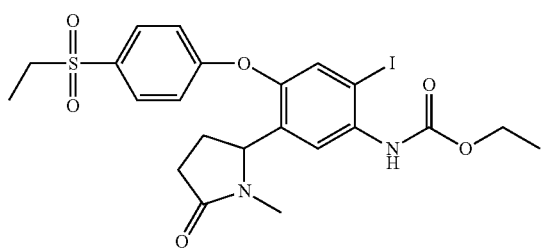 [SMILES: CCOC(=O)Nc1cc(C2CCC(=O)N2C)c(Oc2ccc(S(=O)(=O)CC)cc2)cc1I]

To a solution of the product of Step B in pyridine (20 ml) at 0° C., was added dropwise ethyl chloroformate (0.77 ml, 7.99 mmol). After stirring for 15 minutes at 0° C., it was allowed to warm to RT over 30 minutes. The mixture was concentrated in vacuo, diluted with EtOAc, and washed with aqueous saturated sodium bicarbonate solution. The aqueous phase was extracted with EtOAc, and the combined organic layer was washed with water and brine, dried over MgSO₄, filtered, and concentrated in vacuo. The crude residue was purified by silica gel chromatography (15-100% EtOAc/hexanes) to give ethyl{4-[4-(ethylsulfonyl)phenoxy]-2-iodo-5-(1-methyl-5-oxopyrrolidin-2-yl)phenyl}carbamate as a racemic mixture which was separated by chiral SFC (AD-H, 40% MeOH/CO₂) to give enantiomer A (fast-eluting, 770 mg, 34% yield) and enantiomer B (slow-eluting, 770 mg, 34% yield). ¹H NMR (CDCl₃): δ 7.92 (s, 1 H), 7.88 (d, J=6.8 Hz, 2 H), 7.40 (s, 1 H), 7.05 (d, J=6.8 Hz, 2 H), 6.87 (s, 1 H), 4.76-4.68 (m, 1 H), 4.26 (q, J=7.2 Hz, 2 H), 3.12 (q, J=7.6 Hz, 2 H), 2.71 (s, 3 H), 2.55-2.45 (m, 1 H), 2.41-2.33 (m, 2 H), 1.90-1.84 (m, 1 H), 1.35 (t, J=7.2 Hz, 3 H), 1.30 (t, J=7.6 Hz, 3 H). MS (ES⁺) m/z: 573 (M+H).

Step E. Methyl3-[6-({2-[(ethoxycarbonyl)amino]-5-[4-(ethylsulfonyl)phenoxy]-4-(1-methyl-5-oxopyrrolidin-2-yl)phenyl}ethynyl)pyridin-3-yl]propanoate

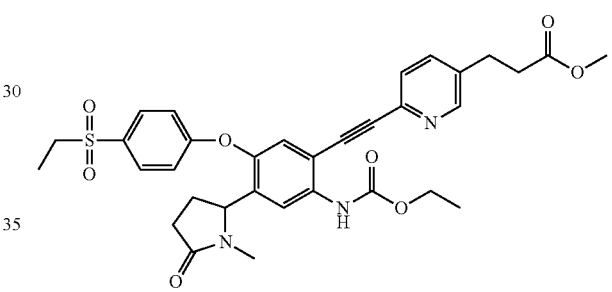

To a solution of enantiomer A of Step C (50 mg, 0.087 mmol) in THF (0.6 mL) under nitrogen at RT was added triethylamine (0.15 ml, 1.09 mmol), PdCl₂(PPh₃)₂ (6.13 mg, 8.73 µmol) and copper(I) iodide (3.3 mg, 0.017 mmol), followed by dropwise addition of methyl 3-(6-ethynylpyridin-3-yl)propanoate, Intermediate 3, (19.8 mg, 0.105 mmol) in THF (0.15 ml). The mixture was heated at 50° C. for 4 hours. It was cooled down and concentrated in vacuo. The crude residue was purified by silica gel chromatography (0-5% MeOH/DCM) to give the alkyne intermediate as a black solid. MS (ES⁺) m/z: 634 (M+H).

Step F. Methyl 3-(6-{5-[4-(ethylsulfonyl)phenoxy]-6-(1-methyl-5-oxopyrrolidin-2-yl)-1H-indol-2-yl}pyridin-3-yl)propanoate

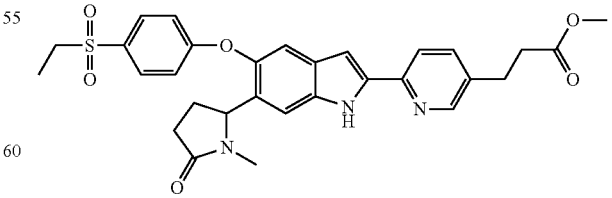

To a solution of the alkyne intermediate in THF (0.7 mL) was added TBAF (1M, 0.44 mL, 0.44 mmol), and the reaction was heated at 55° C. for 4 hours. It was cooled to RT, and partitioned between EtOAc and saturated aqueous NaHCO₃ solution. The organic phase was washed with brine, dried over MgSO₄, filtered, and concentrated in vacuo. The crude residue was purified by silica gel chromatography (0-5% MeOH/DCM) to give methyl 3-(6-{5-[4-(ethylsulfonyl)phenoxy]-6-(1-methyl-5-oxopyrrolidin-2-yl)-1H-indol-2-yl}pyridin-3-yl)propanoate (enantiomer A, 32 mg, 0.057 mmol, 65.2% yield) as a tan solid. MS (ES⁻) m/z: 562 (M+H).

Methyl 3-(6-{5-[4-(ethylsulfonyl)phenoxy]-6-(1-methyl-5-oxopyrrolidin-2-yl)-1H-indol-2-yl}pyridin-3-yl)propanoate (enantiomer B) was prepared similarly from enantiomer B of Step C.

Both enantiomers are active in the biological assays, but usually enantiomer A has better activity than enantiomer B.

Example 2

3-(6-{5-[4-(ETHYLSULFONYL)PHENOXY]-6-(1-METHYL-5-OXOPYRROLIDIN-2-YL)-1H-INDOL-2-YL}PYRIDIN-3-YL)PROPANOIC ACID

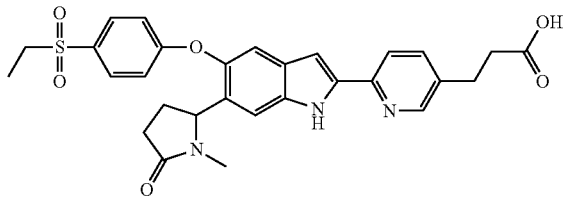 [SMILES: CCS(=O)(=O)c1ccc(Oc2cc3cc(-c4ccc(CCC(=O)O)cn4)[nH]c3cc2C2CCC(=O)N2C)cc1]

To the enantiomers of EXAMPLE 1 (28 mg, 0.050 mmol) in acetonitrile (0.37 mL) was added dropwise a solution of lithium hydroxide (6.28 mg, 0.150 mmol) in water (0.13 mL) and the mixture was stirred at RT overnight. The mixture was diluted with water, acidified with 6 N HCl, and extracted with EtOAc. The organic phase was washed with brine, dried over MgSO₄, filtered, and concentrated in vacuo to give 3-(6-{5-[4-(ethylsulfonyl)phenoxy]-6-(1-methyl-5-oxopyrrolidin-2-yl)-1H-indol-2-yl}pyridin-3-yl)propanoic acid (19 mg, 0.035 mmol, 70% yield) as a light yellow solid. ¹H NMR (DMSO-d6): δ 12.19 (br, s, 1H), 11.77 (s, 1H), 11.51 (s, 1H), 7.90-7.74 (m, 3H), 7.63-7.50 (m, 1H), 7.37-7.25 (m, 2H), 7.18-7.02 (m, 3H), 4.75 (s, 1H), 3.29-3.21 (m, 2H), 2.90-2.82 (m, 2H), 2.64-2.50 (m, 5H), 2.38-2.19 (m, 4H), 1.11-1.06 (m, 3H). MS (ES+) m/z: 548 (M+H)⁻.

Example 3

(2-{5-[4-(ETHYLSULFONYL)PHENOXY]-2-[5-(TRIFLUOROMETHYL)PYRIDIN-2-YL]-1H-INDOL-6-YL}-5-OXOPYRROLIDIN-1-YL)ACETIC ACID

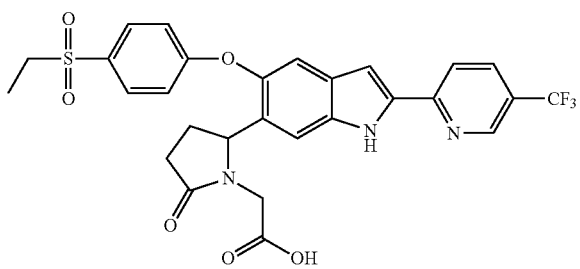 [SMILES: CCS(=O)(=O)c1ccc(Oc2cc3cc(-c4ccc(C(F)(F)F)cn4)[nH]c3cc2C2CCC(=O)N2CC(=O)O)cc1]

Step A: tert-Butyl[2-(2-chloro-5-nitrophenyl)-5-oxopyrrolidin-1-yl]acetate

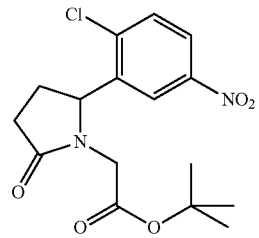 [SMILES: CC(C)(C)OC(=O)CN1C(=O)CCC1c1cc([N+](=O)[O-])ccc1Cl]

To sodium hydride (132 mg, 3.29 mmol) in DMF (10 mL) at 0° C. was added Intermediate 1 (660 mg, 2.74 mmol) in THF (50 ml). After 10 minutes, tert-butyl bromoacetate (0.50 ml, 3.29 mmol) was added and the solution stirred 0° C. to RT. After one hour, the reaction was diluted with water, and extracted three times with EtOAc. The combined organic phase was washed twice with water and brine, dried over MgSO₄, filtered, and concentrated in vacuo. The crude residue was purified by silica gel chromatography to give tert-butyl[2-(2-chloro-5-nitrophenyl)-5-oxopyrrolidin-1-yl]acetate (960 mg, 2.71 mmol, 99% yield) as an orange oil. ¹H NMR (CDCl₃): δ 8.14 (dd, J=2.8, 8.8 Hz, 1H), 8.03 (d, J=2.8 Hz, 1H), 7.60 (d, J=8.8 Hz, 1H), 5.34 (dd, J=5.6, 8.4 Hz, 1H), 4.54 (d, J=17.4 Hz, 1H), 3.15 (d, J=17.4 Hz, 1H), 2.76-2.66 (m, 1H), 2.57 (t, J=8.2 Hz, 2H), 1.92-1.82 (m, 1H), 1.43 (s, 9H). MS (ES⁺) m/z: 299 (M+H-tBu)⁺.

Step B: tert-Butyl(2-{5-[(ethoxycarbonyl)amino]-2-[4-(ethylsulfonyl)phenoxy]-4-iodophenyl}-5-oxopyrrolidin-1-yl)acetate

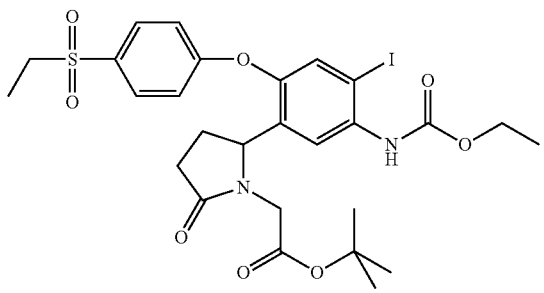 [SMILES: CCOC(=O)Nc1cc(C2CCC(=O)N2CC(=O)OC(C)(C)C)c(Oc2ccc(S(=O)(=O)CC)cc2)cc1I]

The title compound was prepared from the product of Step A (960 mg, 2.71 mmol) following the same procedures used in Example 1 to give tert-butyl(2-{5-[(ethoxycarbonyl)amino]-2-[4-(ethylsulfonyl)phenoxy]-4-iodophenyl}-5-oxopyrrolidin-1-yl)acetate as a racemic mixture which was separated by chiral SFC (AD-H, 30% MeOH/CO₂) to give enantiomer A (fast-eluting, 390 mg, 21% yield) and enantiomer B (slow-eluting, 450 mg, 24% yield) ¹H NMR (CDCl₃): δ 7.93 (s, 1H), 7.86 (dd, J=1.8, 7.0 Hz, 1H), 7.32 (s, 1H), 7.02 (dd, J=1.8, 7.0 Hz, 1H), 6.86 (s, 1H), 5.05 (t, J=7.6 Hz, 1H), 4.47 (d, J=17.6 Hz, 1H), 4.26 (q, J=7.2 Hz, 2H), 3.21 (d, J=17.6 Hz, 1H), 3.11 (q, J=7.6 Hz, 2H), 2.58-2.40 (m, 3H), 1.94-1.86 (m, 1H), 1.37 (s, 9H), 1.35 (t, J=7.2 Hz, 3H), 1.32 (t, J=7.6 Hz, 3H). MS (ES⁺) m/z: 617 (M+H-tBu)⁺.

Step C: tert-Butyl(2-{5-[4-(ethylsulfonyl)phenoxy]-2-[5-(trifluoromethyl)pyridin-2-yl]-1H-indol-6-yl}-5-oxopyrrolidin-1-yl)acetate

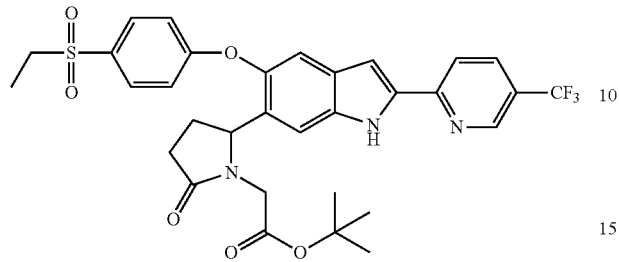

The title compound was prepared from the enantiomers of Step B (100 mg, 0.15 mmol) and commercially available 2-ethynyl-5-(trifluoromethyl)pyridine (61 mg, 0.36 mmol) following the same procedures used in Example 1 to give tert-butyl(2-{5-[4-(ethylsulfonyl)phenoxy]-2-[5-(trifluoromethyl)pyridine-2-yl]-1H-indol-6-yl}-5-oxopyrrolidin-1-yl)acetate (39 mg, 0.061 mmol, 40% yield) as a tan solid. $^1$H NMR (CDCl$_3$): δ 9.62 (s, 1 H), 8.86 (s, 1 H), 7.97 (d, J=7.6 Hz, 1 H), 7.87 (d, J=7.6 Hz, 1 H), 7.85 (s, 1 H), 7.83 (s, 1 H), 7.32 (d, J=8.8 Hz, 2 H), 7.07 (d, J=8.8 Hz, 2 H), 5.14 (t, J=7.6 Hz, 1 H), 4.43 (d, J=17.6 Hz, 1 H), 3.29 (d, J=17.6 Hz, 1 H), 3.10 (q, J=7.4 Hz, 2 H), 2.58-2.42 (m, 3 H), 1.98-1.89 (m, 1 H), 1.37 (s, 9 H), 1.30 (t, J=7.4 Hz, 3 H). MS (ES$^+$) m/z: 588 (M+H-tBu)$^+$.

Step D. (2-{5-[4-(Ethylsulfonyl)phenoxy]-2-[5-(trifluoromethyl)pyridin-2-yl]-1H-indol-6-yl}-5-oxopyrrolidin-1-yl)acetic acid

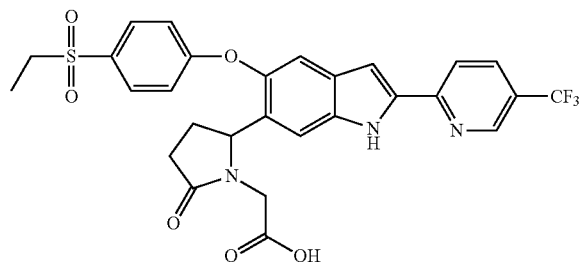 [SMILES: CCS(=O)(=O)c1ccc(Oc2cc3cc(-c4ccc(C(F)(F)F)cn4)[nH]c3cc2C2CCC(=O)N2CC(=O)O)cc1]

To the product of Step B (30 mg, 0.047 mmol) in DCM (0.47 mL) was added TFA (0.16 mL, 2.077 mmol) and the reaction stirred at RT for 24 h. Volatiles were removed in vacuo, and the residue was triturated with hexanes to give (2-{5-[4-(ethylsulfonyl)-phenoxy]-2-[5-(trifluoromethyl)pyridin-2-yl]-1H-indol-6-yl}-5-oxopyrrolidin-1-yl)acetic acid (27 mg, 0.046 mmol, 99% yield) as a yellow solid after drying. $^1$H NMR (DMSO-d$_6$): δ 12.73 (br, 1 H), 12.02 (s, 1 H), 8.99 (s, 1 H), 8.27 (d, J=8.2 Hz, 1 H), 8.20 (d, J=8.2 Hz, 1 H), 7.81 (d, J=8.6 Hz, 2 H), 7.40 (s, 1 H), 7.40 (s, 1 H), 7.34 (s, 1 H), 7.11 (d, J=8.2 Hz, 2 H), 4.98-4.91 (m, 1 H), 4.13 (d, J=17.6 Hz, 1 H), 3.30-3.20 (m, 3 H), 2.42-2.29 (m, 3 H), 1.90-1.83 (m, 1 H), 1.09 (t, J=7.2 Hz, 3 H). MS (ES$^+$) m/z: 588 (M+H)$^+$.

Example 4

METHYL 3-[4-({6-(1-METHYL-5-OXOPYRROLIDIN-2-YL)-2-[5-(TRIFLUORO-METHYL)PYRIDIN-2-YL]-1H-INDOL-5-YL}OXY)PHENYL]PROPIONATE

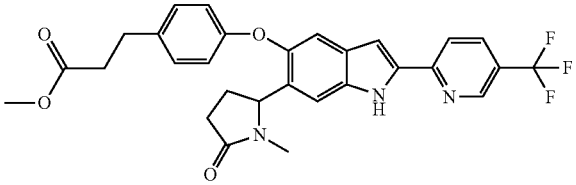 [SMILES: COC(=O)CCc1ccc(Oc2cc3cc(-c4ccc(C(F)(F)F)cn4)[nH]c3cc2C2CCC(=O)N2C)cc1]

Step A. Methyl 3-{4-[2-(1-methyl-5-oxopyrrolidin-2-yl)-4-nitrophenoxy]phenyl}-propanoate

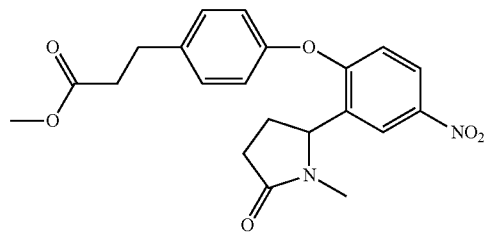

To Intermediate 2 (3 g, 11.78 mmol) in DMA (22.65 ml) was added K$_2$CO$_3$ (3.26 g, 23.56 mmol), followed by methyl 3-(4-hydroxyphenyl)propanoate (2.76 g, 15.31 mmol). The reaction mixture was heated at 120° C. for 3 h. It was then diluted with EtOAc, insolubles were removed by filtration and the filtrate was concentrated. The crude residue was purified with silica gel flash chromatography (0-100% EtOAc/hexanes) to afford methyl 3-{4-[2-(1-methyl-5-oxopyrrolidin-2-yl)-4-nitrophenoxy]phenyl}-propanoate as light brown oil which solidified upon standing (6.12 g, 100% yield). $^1$H NMR (600 MHz, CDCl$_3$): δ 8.09 (dd, J=9.1, 2.7 Hz, 1 H); 8.05 (d, J=2.6 Hz, 1 H); 7.27 (d, 8.4 Hz, 2 H); 6.98 (d, J=8.4 Hz, 2 H); 6.85 (d, J=9.1 Hz, 1 H); 5.05 (dd, J=8.3, 4.6 Hz, 1 H); 3.69 (s, 3 H); 2.99 (t, J=7.7 Hz, 2 H); 2.82 (s, 3 H); 2.66 (t, J=7.7 Hz, 2 H); 2.61-2.55 (m, 2 H); 2.51-2.43 (m, 1 H); 2.02-1.94 (m, 1 H). MS (ES$^+$) m/z: 399.18 (M+H)$^+$.

Step B. Methyl 3-{4-[4-amino-2-(1-methyl-5-oxopyrrolidin-2-yl)phenoxy]phenyl}-propanoate

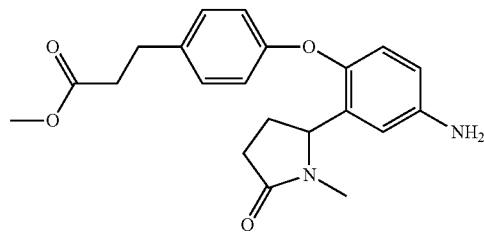 [SMILES: COC(=O)CCc1ccc(Oc2ccc([N+](=O)[O-])cc2C2CCC(=O)N2C)cc1]

To the product of Step A (6.12 g, 11.83 mmol) in THF (92 mL), MeOH (23 mL) and water (23 mL) were added ammonium chloride (0.63 g, 11.83 mmol) and iron powder (1.98 g, 35.5 mmol). The reaction mixture was refluxed for 1 h before it was cooled to room temperature, and filtered through Celite™ diatomaceous earth. The filter cake was washed with MeOH, and the combined filtrate was concentrated in vacuo. The crude residue was purified by silica gel flash chromatography (0-8% MeOH/CH$_2$Cl$_2$) to afford the methyl 3-{4-[4-amino-2-(1-methyl-5-oxopyrrolidin-2-yl)phenoxy]phenyl}-propanoate as light yellow oil (5.0 g, 100% yield). $^1$H NMR (600 MHz, CDCl$_3$): δ 7.10 (d, J=8.4 Hz, 2 H); 6.82-6.78 (m, 3 H); 6.60 (dd, J=8.6, 2.8 Hz, 1 H); 6.45 (d, J=2.8 Hz, 1 H); 4.79 (dd, J=8.1, 4.8 Hz, 1 H); 3.67 (s, 3 H); 2.90 (t, J=7.8 Hz, 2 H); 2.70 (s, 3 H); 2.61 (t, J=7.8 Hz, 2 H); 2.54-2.46 (m, 1 H); 2.39-2.29 (m, 2 H); 1.84-1.77 (m, 1 H). MS (ES$^+$) m/z: 369.18 (M+H)$^+$.

Step C. Methyl 3-(4-{4-[(ethoxycarbonyl)amino]-5-iodo-2-(1-methyl-5-oxo-pyrrolidin-2-yl)phenoxy}phenyl)propanoate

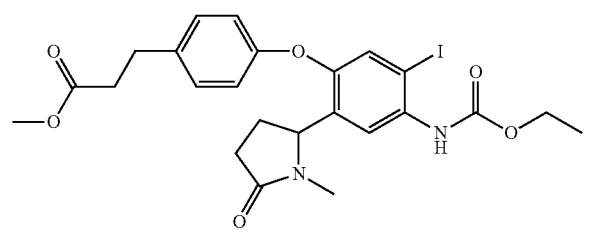 [SMILES: CCOC(=O)Nc1cc(C2CCC(=O)N2C)c(Oc2ccc(CCC(=O)OC)cc2)cc1I]

To a solution of the product of Step B (5.0 g, 11.81 mmol) in a mixed solvents of MeOH (35 ml), 1,4-dioxane (26 ml), and water (26 ml), were added KI (1.96 g, 11.81 mmol) and potassium iodate (1.26 g, 5.90 mmol). While stirring, aqueous HCl (5 M, 5.20 ml, 26.0 mmol) was added. The reaction mixture was stirred at 50° C. for 1.5 h before it was cooled and quenched with saturated aqueous NaHCO$_3$. Volatiles were removed under reduced pressure and the remaining mixture was extracted with CH$_2$Cl$_2$ (3×30 mL). The combined organic phase was washed with brine, dried over MgSO$_4$ and concentrated to black oil which was used in the next step without further purification.

The above black oil was dissolved in pyridine (70 ml), cooled to 0° C., and treated with ethyl chloroformate (1.75 ml, 17.71 mmol). It was stirred for 10 min after being warmed up to RT, and concentrated. The crude residue was purified by silica gel flash chromatography (0-100% EtOAc/hexanes, then 0-10% MeOH/CH$_2$Cl$_2$) to afford methyl 3-(4-{4-[(ethoxycarbonyl)amino]-5-iodo-2-(1-methyl-5-oxo-pyrrolidin-2-yl)phenoxy}phenyl)propanoate as a racemic mixture which was separated by chiral SFC (OJ, 60% MeOH/CO$_2$) to give enantiomer A (fast-eluting, 0.11 g, 1.6% yield) and enantiomer B (slow-eluting, 0.40 g, 6% yield) as a brown oil. $^1$H NMR (600 MHz, CDCl$_3$): δ 7.78 (br, 1 H); 7.27 (s, 1 H); 7.17 (d, J=8.5 Hz, 2 H); 6.85 (d, J=8.5 Hz, 2 H); 4.84 (dd, J=7.8, 4.8 Hz, 1 H); 4.24 (q, J=7.2 Hz, 2 H); 3.68 (s, 3 H); 2.94 (t, J=7.8 Hz, 2 H); 2.74 (s, 3 H); 2.63 (t, J=7.8 Hz, 2 H); 2.56-2.51 (m, 1 H); 2.44-2.35 (m, 2 H); 1.94-1.89 (m, 1 H); 1.34 (t, J=7.2 Hz, 3 H). MS (ES$^+$) m/z: 567.11 (M+H)$^+$.

Step D: Methyl 3-[4-(4-[(ethoxycarbonyl)amino]-2-(1-methyl-5-oxopyrrolidin-2-yl)-5-{[5-(trifluoromethyl)pyridin-2-yl]ethynyl}phenoxy)phenyl]propanoate

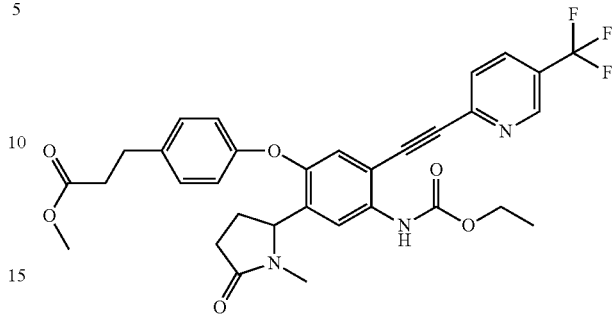

The title compound was prepared from the enantiomers of Step C and 2-ethynyl-5-(trifluoromethyl)pyridine following the same procedures used in Example 1. $^1$H NMR (600 MHz, CDCl$_3$): δ 8.86 (s, 1 H), 7.99 (dd, J=8.3, 2.2 Hz, 1 H), 7.94 (br, 1 H), 7.65 (d, J=8.4 Hz, 1 H), 7.33 (s, 3 H), 7.20 (d, J=8.3 Hz, 2 H), 7.08 (s, 1 H), 6.90 (d, J=8.4 Hz, 2 H), 4.94 (dd, J=8.3, 5.1 Hz, 1 H), 4.27 (q, J=7.1 Hz, 2 H), 3.69 (s, 3 H), 2.95 (t, J=7.7 Hz, 2 H), 2.77 (s, 3 H), 2.65 (t, J=7.7 Hz, 2 H), 2.61-2.54 (m, 1 H), 2.51-2.38 (m, 2 H), 2.01-1.94 (m, 1 H), 1.36 (t, J=7.1 Hz, 3 H). MS (ES$^+$) m/z: 610.27 (M+H)$^+$.

Step E. 4-(Trifluoromethylpyridin-2-yl)-5-[(4-methyl 3-propionate)phenoxy]-6-(1-methyl-5-oxopyrrolidin-2-yl)indole

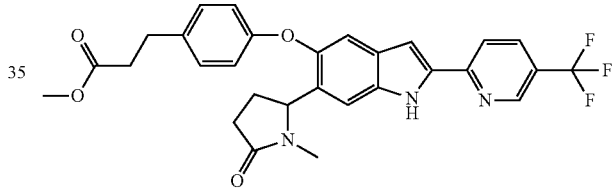

The title compound was prepared from product of Step D (32 mg, 44 μmol) following the same procedures used in Example 1 as yellow solid (5.8 mg, 24.5% yield). $^1$H NMR (500 MHz, CDCl$_3$): δ 9.70 (s, 1 H), 8.85 (s, 1 H), 7.96 (d, J=8.4 Hz, 1 H), 7.86 (d, J=8.4 Hz, 1 H), 7.23 (d, J=3.3 Hz, 2 H), 7.16 (d, J=8.1 Hz, 2 H), 7.03 (s, 1 H), 6.90 (d, J=8.1 Hz, 2 H), 5.04 (m, 1 H), 3.69 (s, 3 H), 2.94 (t, J=7.7 Hz, 2 H), 2.81 (s, 3 H), 2.71-2.60 (m, 3 H), 2.57-2.44 (m, 2 H), 2.01 (m, 1 H). MS (ES$^+$) m/z: 538.26 (M+H)$^+$.

Example 5

3-[4-({6-(1-METHYL-5-OXOPYRROLIDIN-2-YL)-2-[5-(TRIFLUORO-METHYL)PYRIDIN-2-YL]-1H-INDOL-5-YL}OXY)PHENYL]PROPANOIC ACID

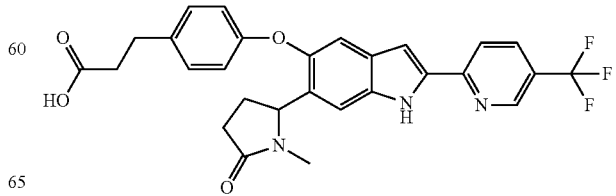

The title compound was prepared from the product of Example 4 following the same procedures used in Example 2. $^1$H NMR (500 MHz, CDCl$_3$): δ 9.70 (s, 1 H), 8.84 (s, 1 H), 7.94 (dd, J=8.4, 2.1 Hz, 1 H), 7.85 (d, J=8.4 Hz, 1 H), 7.24 (s, 1 H), 7.23 (s, 1 H), 7.17 (d, J=8.3 Hz, 2 H), 7.03 (d, J=1.5 Hz, 1 H), 6.89 (d, J=8.4 Hz, 2 H), 5.00 (dd, J=7.7, 4.3 Hz, 1 H), 2.96 (t, J=7.6 Hz, 2 H), 2.78 (s, 3 H), 2.69 (t, J=7.6 Hz, 2 H), 2.66-2.57 (m, 1 H), 2.51-2.40 (m, 2 H), 2.01-1.92 (m, 1 H). MS (ES$^+$) m/z: 524.19 (M+H)$^+$.

Example 6

METHYL 3-(6-{6-(2-FLUOROPHENOXY)-5-[4-(METHYLSULFONYL)PHENOXY]-1H-INDOL-2-YL}PYRIDIN-3-YL)PROPANOATE

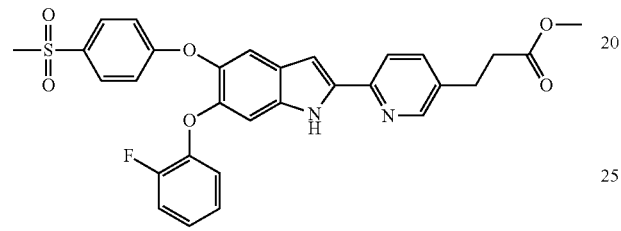

Step A. 5-Fluoro-4-(2-fluorophenoxy)-2-nitroaniline

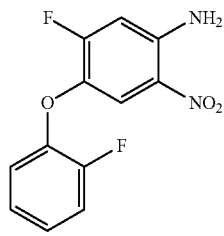 [SMILES: Nc1cc(F)c(Oc2ccccc2F)cc1[N+](=O)[O-]]

To a mixture of 2-fluorophenol (10 g, 89 mmol) and 3,4-difluoro-nitro-benzene (14.16 g, 89 mmol) in acetonitrile (100 ml), was added solid K$_2$CO$_3$ (24.60 g, 178 mmol). After heating to 80° C. for 1 h, the mixture was partitioned between EtOAc and water. The organic phase was washed with brine, dried over Na$_2$SO$_4$ and concentrated to afford 2-fluoro-1-(2-fluorophenoxy)-4-nitrobenzene (8.33 g, 33.2 mmol), which was dissolved in IPA (60 ml) and water (60 ml), mixed with solid NH$_4$Cl (1.774 g, 33.2 mmol) and iron (5.56 g, 99 mmol). The mixture was heated to 60° C. for 1 h, then filtered through a pad of Celite™ diatomaceous earth. The filter cake was washed with IPA, and filtrate was concentrated to a yellow oil, which was triturated with DCM to remove remaining NH$_4$Cl to give 3-fluoro-4-(2-fluorophenoxy)aniline as an off-white solid (7.34 g, 100% yield).

To a cold suspension of 3-fluoro-4-(2-fluorophenoxy)aniline (5.78 g, 26.1 mmol) in TFAA (30 ml, 212 mmol), was added potassium nitrate (2.90 g, 28.7 mmol), and the mixture was stirred for 2 h. Ice-water was added to the light yellow suspension and the solid resulted was collected by filtration. After washing with water, the solid was dissolved in methanol (200 mL) and treated with 7% (w/w) aqueous K$_2$CO$_3$ (50 mL) at room temperature for 1 h. The mixture was diluted with water, and extracted with EtOAc. The organic phase was washed with brine, dried over Na$_2$SO$_4$ and concentrated. Purification by silica gel chromatography (220 g, 0-20% EtOAc/hex) yielded 5-fluoro-4-(2-fluorophenoxy)-2-nitroaniline as an orange solid. $^1$H NMR (500 MHz, CDCl$_3$): δ 7.81 (d, J=8.4 Hz, 1 H); 7.21-7.16 (m, 1 H); 7.13-7.08 (m, 2 H); 7.02-6.97 (m, 1 H); 6.63 (d, J=11.3 Hz, 1 H); 6.11 (s, 2 H). MS (ES$^+$) m/z 267 (M+1)$^+$.

Step B. 1-(2-Fluorophenoxy)-4-iodo-2-[4-(methylsulfonyl)phenoxy]-5-nitrobenzene

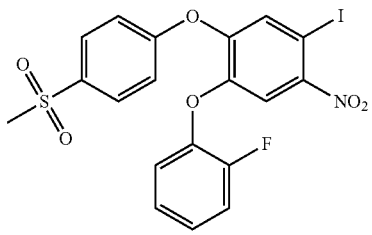 [SMILES: CS(=O)(=O)c1ccc(Oc2cc(I)c([N+](=O)[O-])cc2Oc2ccccc2F)cc1]

To a solution of 5-fluoro-4-(2-fluorophenoxy)-2-nitroaniline (1 g, 3.76 mmol) in acetonitrile (18.78 mL) at 0° C. was added concentrated HCl (0.93 ml, 11.3 mmol), followed by sodium nitrite (0.29 g, 4.1 mmol) in water (2 mL). The mixture was stirred for 30 minutes before an aqueous solution of KI (0.75 g, 4.5 mmol) in water (2 mL) was added dropwise. After 1 h the reaction mixture was quenched with 10% aqueous NaHSO$_3$ solution, and extracted with EtOAc. The organic phase was washed with brine, dried over Na$_2$SO$_4$, and concentrated. The crude residue was purified by silica gel chromatography (40 g, 0-8% EtOAc/hexanes) to give 1-fluoro-2-(2-fluorophenoxy)-5-iodo-4-nitrobenzene as light yellow oil (1.27 g, 90% yield).

1-Fluoro-2-(2-fluorophenoxy)-5-iodo-4-nitrobenzene (1.07 g, 2.84 mmol) and 4-(methylsulfonyl)phenol (0.49 g, 2.84 mmol) were mixed in acetonitrile (14.2 ml), and to this was added solid K$_2$CO$_3$ (0.78 g, 5.68 mmol). The resulting mixture was heated to 80° C. for 1 h, and then partitioned between EtOAc and water. The EtOAc layer was washed with brine, dried over Na$_2$SO$_4$ and concentrated to give 1-(2-fluorophenoxy)-4-iodo-2-[4-(methylsulfonyl)phenoxy]-5-nitrobenzene as colorless oil. $^1$H NMR (500 MHz, CDCl$_3$): δ 7.95 (d, J=8.5 Hz, 2 H); 7.73 (s, 1 H); 7.43 (s, 1 H); 7.25-7.07 (m, 6 H); 3.07 (s, 3 H).

Step C. Ethyl{5-(2-fluorophenoxy)-2-iodo-4-[4-(methylsulfonyl)phenoxy]phenyl}-carbamate

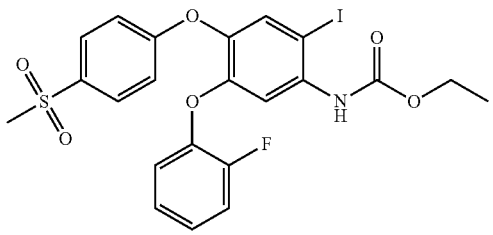 [SMILES: CCOC(=O)Nc1cc(Oc2ccccc2F)c(Oc2ccc(S(C)(=O)=O)cc2)cc1I]

To a suspension of the product of Step B (1.44 g, 2.72 mmol) in IPA (50 mL) and water (30 mL) was added ammonium chloride (0.29 g, 5.44 mmol) and iron (0.76 g, 13.60 mmol). The mixture was heated to 60° C. for 1 h, and filtered through a pad of Celite™ diatomaceous earth after it cooled down. The filter cake was washed with IPA, and the filtrate was concentrated and partitioned between EtOAc and water. The EtOAc layer was washed with brine, dried over Na₂SO₄ and concentrated to give 5-(2-fluorophenoxy)-2-iodo-4-[4-(methylsulfonyl)phenoxy]aniline as a gummy residue.

A pyridine (13.6 mL) solution of 5-(2-fluorophenoxy)-2-iodo-4-[4-(methylsulfonyl)phenoxy]aniline (1.36 g, 2.72 mmol) at 0° C. was treated with ethyl chloroformate (1.05 mL, 10.90 mmol). The mixture was stirred for 15 minutes before allowed to warm to room temperature. Volatiles were removed under reduced pressure, and the residue was partitioned between EtOAc and water. Organic phase was washed with brine, dried over Na₂SO₄ and concentrated. The crude residue was purified by silica gel chromatography (40 g, 0-33% EtOAc/hexanes) to give ethyl{5-(2-fluorophenoxy)-2-iodo-4-[4-(methylsulfonyl)phenoxy]phenyl}-carbamate. ¹H NMR (500 MHz, CDCl₃): δ 7.89-7.81 (m, 2 H); 7.57 (s, 1 H); 7.16-6.99 (m, 7 H); 6.90 (s, 1 H); 4.18 (q, J=7.1 Hz, 2 H); 3.03 (s, 3 H); 1.31 (t, 3 H). MS (ES⁺) m/z 572 (M+H)⁺.

Step D. Methyl 3-(6-{6-(2-fluorophenoxy)-5-[4-(methylsulfonyl)-phenoxy]-1H-indol-2-yl}pyridin-3-yl)propanoate

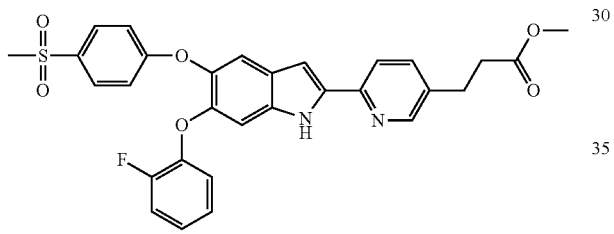

The title compound was prepared from the product of Step C following the same procedures used for Example 1. ¹H NMR (500 MHz, CDCl₃): δ 8.42 (s, 1 H); 7.82 (d, J=8.6 Hz, 2 H); 7.70 (d, J=8.2 Hz, 1 H); 7.58 (d, J=8.3 Hz, 1 H); 7.42 (s, 1 H); 7.14-7.00 (m, 6 H); 6.99-6.93 (m, 2 H); 3.69 (s, 3 H); 3.02 (s, 3 H); 2.98 (t, J=7.5 Hz, 2 H); 2.68 (t, J=7.6 Hz, 2 H). MS (ES⁺) m/z 561 (M+H)⁺.

Example 7

3-(6-{6-(2-FLUOROPHENOXY)-5-[4-(METHYL-SULFONYL)PHENOXY]-1H-INDOL-2-YL}PYRIDIN-3-YL)PROPANOIC ACID

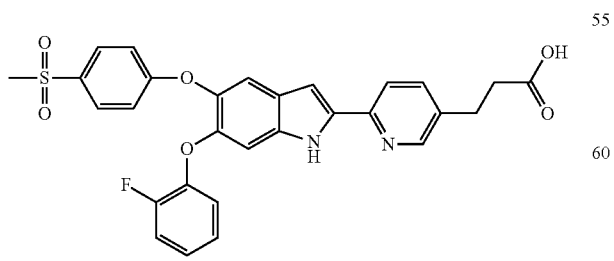

The title compound was prepared from Example 6 using the same procedure for Example 2. ¹H NMR (500 MHz, DMSO-d6): δ 11.73 (s, 1 H); 8.52 (s, 1 H); 7.91 (d, J=8.2 Hz, 1 H); 7.85 (d, J=8.5 Hz, 2 H); 7.77 (d, J=8.3 Hz, 1 H); 7.54 (s, 1 H); 7.33 (m, 1 H); 7.15 (d, J=7.8 Hz, 4 H); 7.08 (d, J=8.9 Hz, 3 H); 3.17 (s, 3 H); 2.89 (t, J=7.4 Hz, 2 H); 2.64 (t, J=7.5 Hz, 2 H). MS (ES⁺) m/z 547 (M+H)⁺.

Example 8

N-({6-[6-(1-METHYL-5-OXOPYRROLIDIN-2-YL)-5-{[6-(METHYL-SULFONYL)PYRIDIN-3-YL]OXY}-1H-INDOL-2-YL]PYRIDIN-3-YL}-CARBONYL)-β-ALANINE

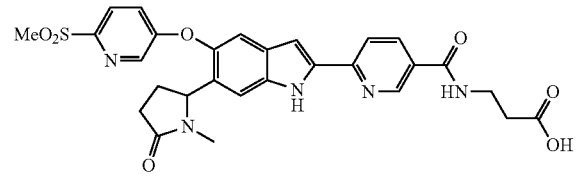 [SMILES: CN1C(=O)CCC1c1cc2[nH]c(-c3ccc(C(=O)NCCC(=O)O)cn3)cc2cc1Oc1ccc(S(C)(=O)=O)nc1]

Step A. 1-METHYL-5-(2-((6-(METHYLSULFO-NYL)PYRIDIN-3-YL)OXY)-5-NITROPHENYL)PYRROLIDIN-2-ONE

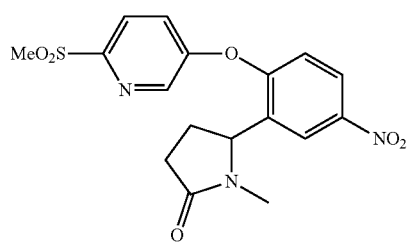 [SMILES: CN1C(=O)CCC1c1cc([N+](=O)[O-])ccc1Oc1ccc(S(C)(=O)=O)nc1]

The title compound was prepared from 6-(methylsulfonyl)pyridin-3-ol and Intermediate 2 following the same procedure used for Example 1 Step A. MS (ES⁺) m/z: 392.19 (M+H)⁺.

Step B. ETHYL(2-IODO-5-(1-METHYL-5-OX-OPYRROLIDIN-2-YL)-4-((6-(METHYLSULFO-NYL)PYRIDIN-3-YL)OXY)PHENYL)CARBAM-ATE

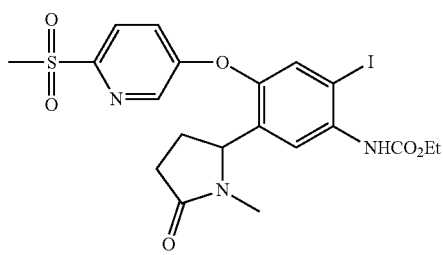

The title compound was prepared from the product of Step A following the same procedure used for Example 1. MS (ES⁺) m/z: 560.11 (M+H)⁺.

Step C. METHYL 6-((2-((ETHOXYCARBONYL)AMINO)-4-(1-METHYL-5-OXOPYRROLIDIN-2-YL)-5-((6-(METHYLSULFONYL)PYRIDIN-3-YL)OXY)PHENYL)ETHYNYL)NICOTINATE

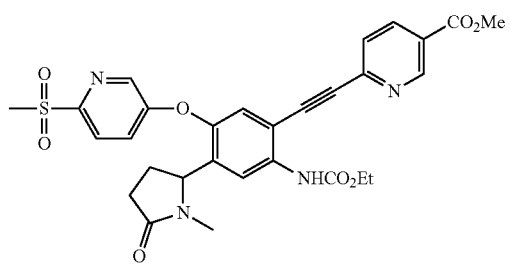

The title compound was prepared from the product of Step B following the same procedure used for Example 1. MS (ES⁺) m/z: 593.07 (M+H)⁺.

Step D. METHYL 6-(6-(1-METHYL-5-OXOPYRROLIDIN-2-YL)-5-((6-(METHYLSULFONYL)PYRIDIN-3-YL)OXY)-1H-INDOL-2-YL)NICOTINATE

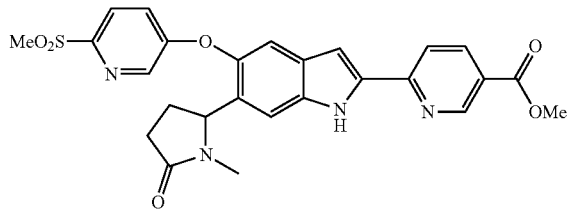 [SMILES: COC(=O)c1ccc(-c2cc3cc(Oc4ccc(S(C)(=O)=O)nc4)c(C4CCC(=O)N4C)cc3[nH]2)nc1]

The title compound was prepared from the product of Step C following the same procedure used for Example 1. MS (ES⁺) m/z: 521.23 (M+H)⁺.

Step E. 6-[6-(1-METHYL-5-OXOPYRROLIDIN-2-YL)-5-{[6-(METHYLSULFONYL)PYRIDIN-3-YL]OXY}-1H-INDOL-2-YL]PYRIDINE-3-CARBOXYLIC ACID

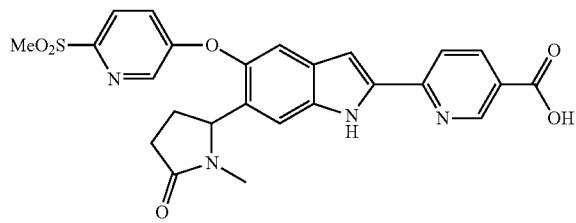 [SMILES: CN1C(=O)CCC1c1cc2[nH]c(-c3ccc(C(=O)O)cn3)cc2cc1Oc1ccc(S(C)(=O)=O)nc1]

The title compound was prepared from the product of Step D according to procedures for Example 2. MS (ES⁺) m/z: 507.01 (M+H)⁺.

Step F. ETHYL N-({6-[6-(1-METHYL-5-OXOPYRROLIDIN-2-Y)-5-{[6-(METHYL-SULFONYL)PYRIDIN-3-YL]OXY}-1H-INDOL-2-YL]PYRIDIN-3-YL}-CARBONYL)-β-ALANINATE

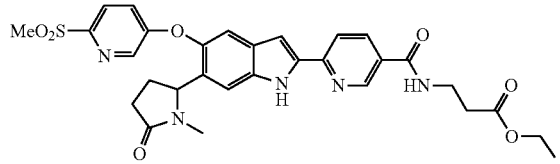 [SMILES: CCOC(=O)CCNC(=O)c1ccc(-c2cc3cc(Oc4ccc(S(C)(=O)=O)nc4)c(C4CCC(=O)N4C)cc3[nH]2)nc1]

To a solution of the product of Step A (25 mg, 0.049 mmol) and β-alanine (11 mg, 0.074 mmol) in DMF (1 mL) at RT was added HATU (28 mg, 0.074 mmol), followed by DIEA (0.03 ml, 0.15 mmol) and the reaction was allowed to stir at room temperature overnight. The reaction mixture was quenched with water and extracted with EtOAc. The organic layer was washed with water and brine, dried with Na₂SO₄, filtered and concentrated to give a brown residue. The crude residue was purified by preparative TLC (5% MeOH/DCM) to afford ethyl N-({6-[6-(1-methyl-5-oxopyrrolidin-2-yl)-5-{[6-(methyl-sulfonyl)pyridin-3-yl]oxy}-1H-indol-2-yl]pyridin-3-yl}-carbonyl)-β-alaninate (28 mg, 0.046 mmol, 94% yield). MS (ES⁺) m/z: 606.78 (M+H)⁺.

Step G. N-({6-[6-(1-METHYL-5-OXOPYRROLIDIN-2-YL)-5-{[6-(METHYL-SULFONYL)PYRIDIN-3-YL]OXY}-1H-INDOL-2-YL]PYRIDIN-3-YL}-CARBONYL)-β-ALANINE

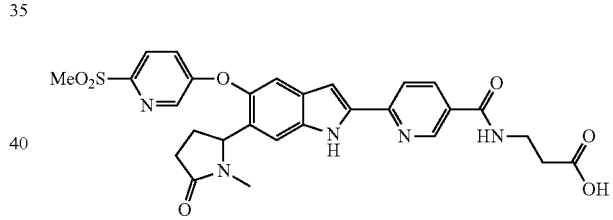

The title compound was prepared from the product of Step F according to procedures described for Example 2. MS (ES⁺) m/z: 577.92 (M+H)⁺.

Example 9

3-[6-(5-{[6-(METHYLSULFONYL)PYRIDIN-3-YL]OXY}-6-[(2-OXOPYRROLIDIN-1-YL)METHYL]-1H-PYRROLO[2,3-B]PYRIDIN-2-YL)PYRIDIN-3-YL]PROPANOIC ACID

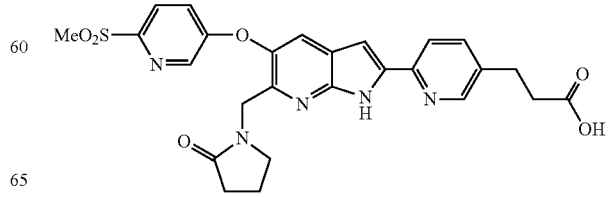

Step A. Methyl 6-chloro-3-{[6-(methylsulfonyl)pyridin-3-yl]oxy}pyridine-2-carboxylate

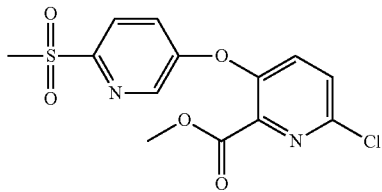 [SMILES: COC(=O)c1nc(Cl)ccc1Oc1ccc(S(C)(=O)=O)nc1]

To a solution of commercially available methyl 6-chloro-3-fluoropyridine-2-carboxylate (1.84 g, 9.71 mmol) and commercially available 6-(methylsulfonyl)pyridin-3-ol (2.52 g, 14.56 mmol) in DMF (40 mL) at room temperature was added potassium carbonate (2.68 g, 19.41 mmol). The reaction mixture was heated at 80° C. for 16 h before it was cooled to room temperature, and partitioned between ethyl acetate and water. The organic layer was washed with water, and brine, dried over sodium sulfate and concentrated to give methyl 6-chloro-3-{[6-(methylsulfonyl)pyridin-3-yl]oxy}pyridine-2-carboxylate (2.7 g, 7.88 mmol, 81% yield). $^1$H NMR (500 MHz, CDCl$_3$): δ 8.43 (d, J=2.8 Hz, 1H), 8.07 (d, J=8.7 Hz, 1H), 7.60 (d, J=8.6 Hz, 1H), 7.51 (d, J=8.6 Hz, 1H), 7.34 (dd, J=9.0, 3.0 Hz, 1H), 3.90 (s, 3H), 3.22 (s, 3H). MS (ES$^+$) m/z: 343.07 (M+H)$^+$.

Step B. (6-Chloro-3-{[6-(methylsulfonyl)pyridin-3-yl]oxy}pyridin-2-yl)methanol

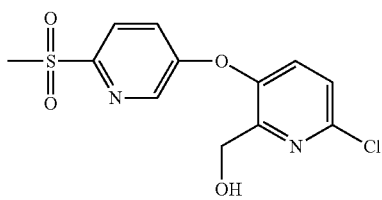 [SMILES: CS(=O)(=O)c1ccc(Oc2ccc(Cl)nc2CO)cn1]

To a solution of methyl 6-chloro-3-{[6-(methylsulfonyl)pyridin-3-yl]-oxy}pyridine-2-carboxylate (2.7 g, 7.88 mmol) in methanol (40 mL) at 0° C. was added sodium borohydride (1.49 g, 39.4 mmol) and the reaction was allowed to warm to RT and stirred for 16 h. The reaction mixture was diluted with ethyl acetate, neutralized with acetic acid (2.35 mL, 41.0 mmol), and washed with water and brine. The organic layer was dried over sodium sulfate and concentrated in vacuo. The residue was azeotroped with toluene to give (6-chloro-3-{[6-(methylsulfonyl)pyridin-3-yl]oxy}pyridin-2-yl)methanol (2.4 g, 7.63 mmol, 97% yield) as a yellow oil. $^1$H NMR (500 MHz, CDCl$_3$): δ 8.49 (d, J=2.8 Hz, 1 H); 8.11 (d, J=8.6 Hz, 1 H); 7.43 (dd, J=8.8, 2.9 Hz, 1 H); 7.36 (m, 2 H); 4.78 (d, J=4.5 Hz, 2 H); 3.26 (s, 3 H). MS (ES$^+$) m/z: 314.91 (M+H)$^+$;

Step C. 6-Chloro-2-(chloromethyl)-3-{[6-(methylsulfonyl)pyridin-3-yl]oxy}pyridine

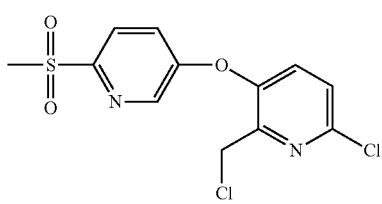 [SMILES: CS(=O)(=O)c1ccc(Oc2ccc(Cl)nc2CCl)cn1]

To a solution of (6-chloro-3-{[6-(methylsulfonyl)pyridin-3-yl]oxy}-pyridin-2-yl)methanol (2.4 g, 7.63 mmol) in dichloromethane (40 mL) at 0° C. was added thionyl chloride (1.67 mL, 22.88 mmol), and the reaction mixture was stirred at room temperature for 16 h. The reaction mixture was diluted with dichloromethane (200 mL) and washed twice with sodium bicarbonate. The organic layer was washed with brine, dried over sodium sulfate and concentrated to give 6-chloro-2-(chloromethyl)-3-{[6-(methylsulfonyl)pyridin-3-yl]oxy}pyridine (2.2 g, 6.60 mmol, 87% yield) as yellow oil. $^1$H NMR (500 MHz, CDCl$_3$): δ 8.50 (d, J=2.7 Hz, 1 H); 8.10 (d, J=8.6 Hz, 1 H); 7.44 (dd, J=8.6, 2.8 Hz, 2 H); 7.39 (d, J=8.6 Hz, 2 H); 7.32 (d, J=8.6 Hz, 2 H); 4.72 (s, 2 H); 3.27 (s, 3 H). MS (ES$^+$) m/z: 332.27 (M+H)$^+$.

Step D. 1-[(6-Chloro-3-{[6-(methylsulfonyl)pyridin-3-yl]oxy}pyridin-2-yl)methyl]-pyrrolidin-2-one

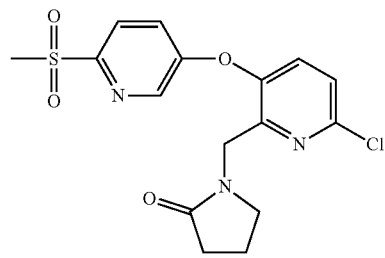 [SMILES: CS(=O)(=O)c1ccc(Oc2ccc(Cl)nc2CN2CCCC2=O)cn1]

To a solution of 2-pyrrolidinone (0.79 g, 9.24 mmol) in THF (33 mL) at 0° C. was added sodium hydride (0.40 g, 9.24 mmol), and the mixture was stirred at 0° C. for 20 min before 6-chloro-2-(chloromethyl)-3-{[6-(methylsulfonyl)pyridin-3-yl]-oxy}pyridine (2.2 g, 6.60 mmol) was added in as a solution in THF (5 mL). The reaction mixture was allowed to warm to room temperature and then stirred for 16 h at 60° C. After cooled to room temperature, it was partitioned between ethyl acetate and water. The EtOAc layer was washed with water and brine, dried over Na$_2$SO$_4$ and concentrated in vacuo. The crude residue was purified by silica gel column chromatography (50% EtOAc/hexanes) gave 1-[(6-chloro-3-{[6-(methylsulfonyl)pyridin-3-yl]oxy}pyridin-2-yl)methyl]-pyrrolidin-2-one (1.3 g, 3.40 mmol, 52% yield). $^1$H NMR (500 MHz, CDCl$_3$): δ 8.43 (d, J=2.8 Hz, 1 H); 8.07 (d, J=9.0 Hz, 1 H); 7.41 (dd, J=8.5 Hz, J=3.0 Hz, 1 H); 7.32 (m, 2 H); 4.58 (s, 2 H); 3.50 (m, 2 H); 3.22 (s, 3 H); 2.31 (m, 2 H); 2.01 (m, 2 H). MS (ES$^+$) m/z: 382.14 (M+H)$^+$.

Step E. 1-[(6-[(4-Methoxyphenyl)amino]-3-{[6-(methylsulfonyl)pyridin-3-yl]oxy}-pyridin-2-yl)methyl]pyrrolidin-2-one

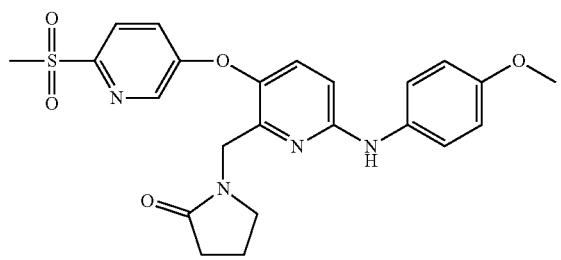

A degassed mixture of Pd₂dba₃ (219 mg, 0.239 mmol), potassium phosphate tribasic (760 mg, 3.58 mmol), MePhos (131 mg, 0.358 mmol), product of Step D (456 mg, 1.194 mmol), and 4-methoxybenzylamine (246 mg, 1.791 mmol) in dimethoxyethane (5 mL) was stirred at 80° C. for 16 h. The reaction mixture was loaded directly onto a silica gel column and eluted with 80% EtOAc/hexanes/containing 2% triethylamine to give the title compound (435 mg, 0.901 mmol, 75% yield). $^1$H NMR (500 MHz, CDCl₃): δ 8.38 (d, J=2.7 Hz, 1 H); 8.00 (d, J=8.7 Hz, 1 H); 7.29 (m, 3 H); 7.12 (d, J=8.8 Hz, 1 H); 6.89 (d, J=8.5 Hz, 2 H); 6.37 (d, J=8.8 Hz, 1 H); 4.90 (m, 1 H); 4.44 (d, J=5.7 Hz, 2 H); 4.40 (s, 2 H); 3.82 (s, 3 H); 3.35 (t, J=19.5 Hz, 2 H); 3.20 (s, 3 H); 2.25 (t, J=16.0 Hz, 2 H); 1.88 (m, 2 H). MS (ES⁺) m/z: 483.16 (M+H)⁺;

Step F. 1-[(6-amino-5-iodo-3-{[6-(methylsulfonyl) pyridin-3-yl]oxy}pyridin-2-yl)-methyl]pyrrolidin-2-one

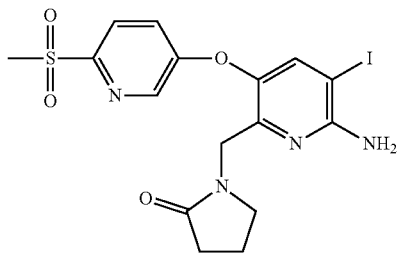 [SMILES: CS(=O)(=O)c1ccc(Oc2cc(I)c(N)nc2CN2CCCC2=O)cn1]

The product of Step E (833 mg, 1.73 mmol) was treated with neat trifluoroacetic acid (0.13 mL, 1.73 mmol) at 60° C. for 2 h. The reaction mixture was concentrated in vacuo, azeotroped with toluene, and partitioned between EtOAc and aqueous sodium bicarbonate solution. The organic layer was washed with water, dried over Na₂SO₄, and concentrated in vacuo to give 1-[(6-amino-3-{[6-(methylsulfonyl)-pyridin-3-yl]oxy}pyridin-2-yl)methyl]pyrrolidin-2-one (626 mg, 1.726 mmol, 100% yield), which was taken to the next step without further purification. MS (ES⁺) m/z: 362.99 (M+H)⁺.

To a solution of 1-[(6-amino-3-{[6-(methylsulfonyl)-pyridin-3-yl]-oxy}pyridin-2-yl)methyl]pyrrolidin-2-one (680 mg, 1.876 mmol) in methanol (25 mL) at room temperature was added silver sulfate (585 mg, 1.876 mmol) followed by iodine (476 mg, 1.876 mmol). The reaction mixture was stirred at room temperature for 4 h. To the reaction mixture was then added aqueous sodium thiosulfate and sodium bicarbonate, and the mixture was stirred for 10 min. The reaction mixture was extracted with dichloromethane, and the organic layer was washed with brine. The organic layer was dried, filtered, and concentrated. Crude residue was purified to give 890 mg of 1-[(6-amino-5-iodo-3-{[6-(methyl-sulfonyl)pyridin-3-yl]oxy}pyridin-2-yl)-methyl] pyrrolidin-2-one (1.88 mmol, 97% yield). $^1$H NMR (500 MHz, CDCl₃): δ 8.38 (d, J=2.8 Hz, 1 H); 8.03 (d, J=8.7 Hz, 1 H); 7.588 (s, 1 H); 7.33 (dd, J=8.7, 2.9 Hz, 1 H); 4.99 (s, 2 H); 4.37 (s, 3 H); 3.38 (t, J=14.0 Hz, 2 H); 2.24 (t, J=14.5 Hz, 2 H); 2.00-1.92 (m, 2 H). MS (ES⁺) m/z: 488.80 (M+H)⁺.

Step G. Ethyl(3-iodo-5-{[6-(methylsulfonyl)pyridin-3-yl]oxy}-6-[(2-oxopyrrolidin-1-yl)methyl]pyridin-2-yl)carbamate

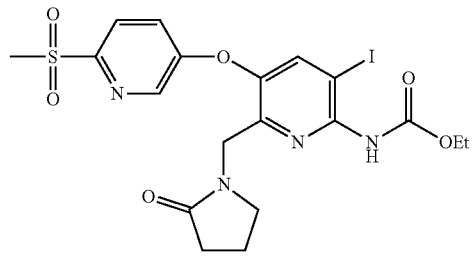 [SMILES: CCOC(=O)Nc1nc(CN2CCCC2=O)c(Oc2ccc(S(C)(=O)=O)nc2)cc1I]

To a solution of 1-[(6-amino-5-iodo-3-{[6-(methyl-sulfonyl)pyridin-3-yl]oxy}pyridin-2-yl)-methyl]pyrrolidin-2-one (200 mg, 0.410 mmol) in pyridine (0.033 mL, 0.410 mmol) at room temperature was added DMAP (10.01 mg, 0.082 mmol) and ethyl chloroformate (0.28 mL, 2.87 mmol). The reaction mixture was concentrated, azeotroped with toluene, and purified by preparative TLC (50% ethyl acetate/hexane) to give mono-carbamate (27 mg, 0.048 mmol, 11.76% yield) and bis-carbamate (100 mg, 0.158 mmol, 38.6% yield).

To a solution of the bis-carbamate (60 mg, 0.095 mmol) in ethanol (3 mL) at room temperature was added 2 N aqueous NaOH (0.190 mL, 0.190 mmol), and the mixture was stirred for 1 h. The reaction mixture was acidified to pH 4 with 5% aqueous citric acid and extracted with ethyl acetate. The organic layer was washed with water and brine, dried over Na₂SO₄, and concentrated in vacuo to a brown residue, which was purified by passing through a silica plug (8% methanol/dichloromethane/2% triethylamine) to give the title compound (53 mg, 0.095 mmol, 100% yield). $^1$H NMR (500 MHz, CDCl₃): δ 8.44 (d, J=2.8 Hz, 1 H); 8.08 (d, J=8.7 Hz, 1 H); 7.70 (s, 1 H); 7.42 (dd, J=8.6, 2.7 Hz, 1 H); 4.52 (s, 2 H); 4.27 (q, J=7.1 Hz, 2 H); 3.62 (m, 3 H); 3.23 (s, 3 H); 2.35 (m, 2 H); 2.04 (m, 2 H); 1.40-1.36 (m, 3 H). MS (ES⁺) m/z: 560.84 (M+H)⁺.

Step H. 3-[6-(5-{[6-(Methylsulfonyl)pyridin-3-yl] oxy}-6-[(2-oxopyrrolidin-1-yl)methyl]-1H-pyrrolo [2,3-b]pyridin-2-yl)pyridin-3-yl]propanoic acid

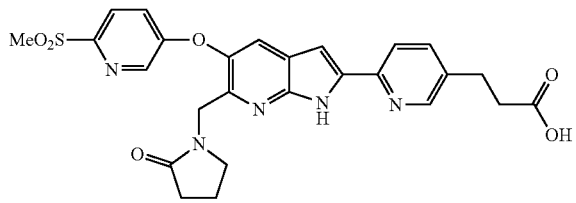 [SMILES: CS(=O)(=O)c1ccc(Oc2cc3cc(-c4ccc(CCC(=O)O)cn4)[nH]c3nc2CN2CCCC2=O)cn1]

The title compound was prepared from the product of Step G and INTERMEDIATE 3 according to procedures for EXAMPLE 1 and 2. MS (ES⁺) m/z: 535.94 (M+H)⁺.

Example 10

METHYL 3-{6-[6-(1-ACETYLPYRROLIDIN-2-YL)-5-{[6-(AZETIDIN-1-YLCARBONYL)PYRIDIN-3-YL]OXY}-1H-INDOL-2-YL]PYRIDIN-3-YL}PROPANOATE

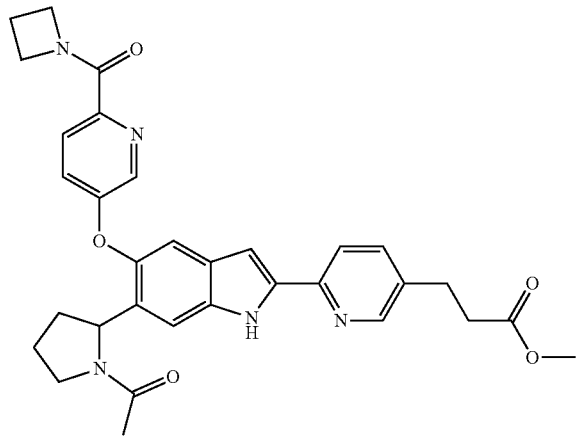 [SMILES: COC(=O)CCc1ccc(-c2cc3cc(Oc4ccc(C(=O)N5CCC5)nc4)c(C4CCCN4C(C)=O)cc3[nH]2)nc1]

Step A. (R)-1-(2-(2-((6-(AZETIDINE-1-CARBONYL)PYRIDIN-3-YL)OXY)-5-NITROPHENYL)PYRROLIDIN-1-YL)ETHANONE

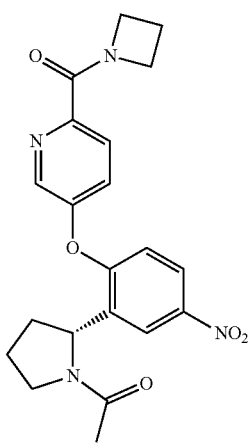 [SMILES: CC(=O)N1CCC[C@@H]1c1cc([N+](=O)[O-])ccc1Oc1ccc(C(=O)N2CCC2)nc1]

The title compound was prepared from azetidin-1-yl(5-hydroxypyridin-2-yl)methanone (PCT/JP2009/064072) and (R)-1-(2-(2-fluoro-5-nitrophenyl)pyrrolidin-1-yl)ethanone (PCT/JP2009/064073) following the procedure of Example 1 Step A. MS (ES$^+$) m/z: 410.9 (M+H)$^+$.

Step B. (R)-1-(2-(5-AMINO-2-((6-(AZETIDINE-1-CARBONYL)PYRIDIN-3-YL)OXY)PHENYL)PYRROLIDIN-1-YL)ETHANONE

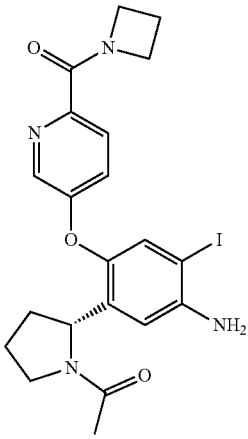 [SMILES: CC(=O)N1CCC[C@@H]1c1cc(N)c(I)cc1Oc1ccc(C(=O)N2CCC2)nc1]

The title compound was prepared from the product of Step A, following the procedure of Example 1 Step B. MS (ES$^+$) m/z: 506.9 (M+H)$^+$.

Step C. (R)-METHYL 3-(6-((4-(1-ACETYLPYRROLIDIN-2-YL)-5-((6-(AZETIDINE-1-CARBONYL)PYRIDIN-3-YL)OXY)-2-((ETHOXYCARBONYL)AMINO)PHENYL)ETHYNYL)PYRIDIN-3-YL)PROPANOATE

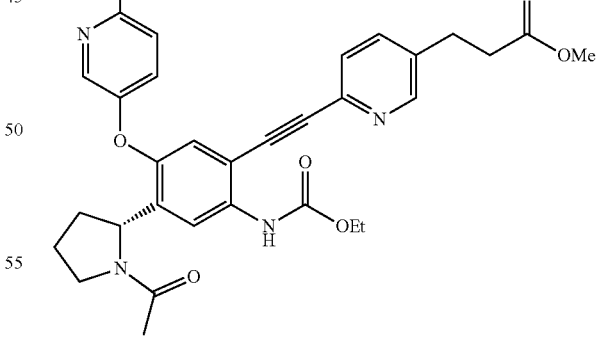

The title compound was prepared from the product of Step B, following the procedure described in Example 1 Step C and D. MS (ES$^+$) m/z: 640.37 (M+H)$^+$.

Step D. (R)-METHYL 3-(6-(6-(1-ACETYLPYR-ROLIDIN-2-YL)-5-((6-(AZETIDINE-1-CARBO-NYL)PYRIDIN-3-YL)OXY)-1H-INDOL-2-YL)PYRIDIN-3-YL)PROPANOATE

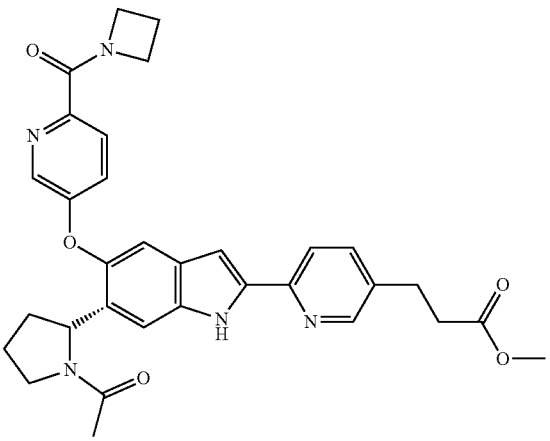

The title compound was prepared from the product of Step C, following the procedure described in Example 1 Step E. MS (ES$^+$) m/z: 568.33 (M+H)$^+$.

Example 11

3-{6-[6-(1-ACETYLPYRROLIDIN-2-YL)-5-{[6-(AZETIDIN-1-YLCARBONYL)PYRIDIN-3-YL]OXY}-1H-INDOL-2-YL]PYRIDIN-3-YL}PROPANOIC ACID

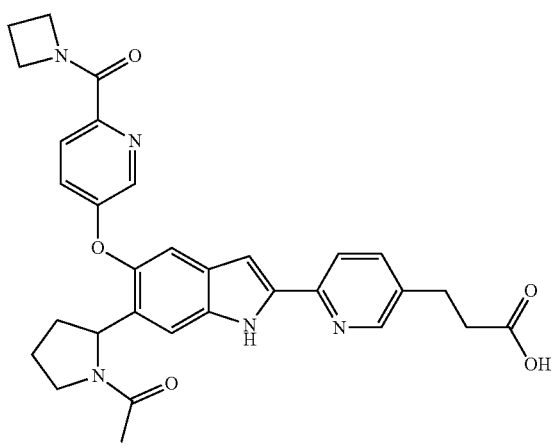 [SMILES: CC(=O)N1CCCC1c1cc2[nH]c(-c3ccc(CCC(=O)O)cn3)cc2cc1Oc1ccc(C(=O)N2CCC2)nc1]

The title compound was prepared from the product of Example 10, following the procedure described in Example 2. MS (ES$^+$) m/z: 554.09 (M+H)$^+$.

Example 12

(6-(5-(4-(ETHYLSULFONYL)PHENOXY)-6-(1-METHYL-5-OXOPYRROLIDIN-2-YL)-1H-INDOL-2-YL)PYRIDIN-3-YL)(METHYL)PHOSPHINIC ACID

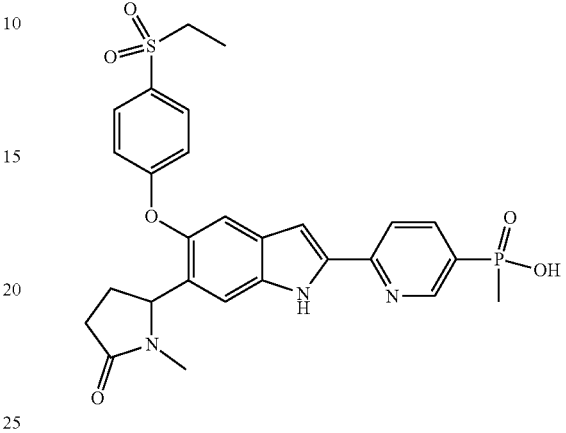

Step A: 5-Bromo-2-{5-[4-(ethylsulfonyl)phenoxy]-6-(1-methyl-5-oxopyrrolidin-2-yl)-1H-indol-2-yl}pyridine

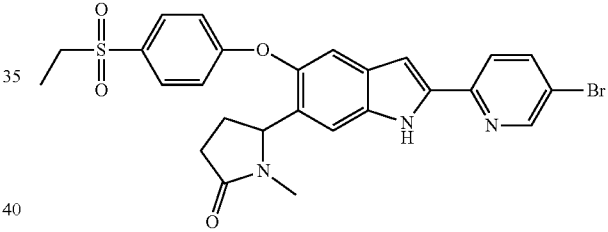

The title compound was prepared from 5-bromo-2-ethynylpyridine, following procedures used in Step D and E of Example 1. MS (ES$^+$) m/z: 554/556 (M+H)$^+$.

Step B: 1-Methyl-1-(6-{5-[4-(ethylsulfonyl)phenoxy]-6-(1-methyl-5-oxopyrrolidin-2-yl)-1H-indol-2-yl}pyridin-3-yl)phosphinic acid

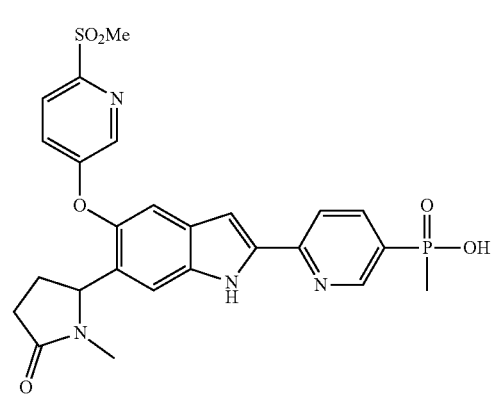 [SMILES: CN1C(=O)CCC1c1cc2[nH]c(-c3ccc(P(C)(=O)O)cn3)cc2cc1Oc1ccc(S(C)(=O)=O)nc1]

To the product of Step A (69 mg, 0.12 mmol) in toluene (1 mL) under nitrogen at RT was added ethyl methylphosphinate (16 mg, 0.15 mmol), triethylamine (0.052 mL, 0.37 mmol), and Pd(PPh$_3$)$_4$ (29 mg, 0.025 mmol). The mixture was heated at 90° C. overnight. It was partitioned between EtOAc and water, the organic phase was washed with brine, dried over MgSO$_4$, filtered, and concentrated in vacuo. The crude residue was purified by silica gel chromatography (0-10% MeOH/DCM) to give the phosphinate ester intermediate as a yellow solid. MS (ES$^-$) m/z: 582 (M+H)$^+$.

To a solution of the phosphinate ester intermediate in DCM (0.5 mL) at RT was added 1,1,1,3,3,3-hexamethyldisilizane (0.075 mL, 0.358 mmol) followed by bromotrimethylsilane (0.023 mL, 0.179 mmol) and the mixture was stirred overnight. To the cloudy reaction mixture was added a drop of iodotrimethylsilane. The reaction cleared up instantly and was stirred for an additional 2 h. It was concentrated in vacuo and the residue was triturated with EtOAc. Insolubles were filtered off, filtrate and washings were concentrated in vacuo. The residue was dissolved in MeOH and stirred vigorously for 3 h. After volatiles were removed under reduced pressure, the residue was partitioned between EtOAc and brine. The organic phase was dried over MgSO$_4$ and filtered immediately. Filtrate was concentrated in vacuo to give 1-methyl-1-(6-{5-[4-(ethylsulfonyl)phenoxy]-6-(1-methyl-5-oxopyrrolidin-2-yl)-1H-indol-2-yl}pyridin-3-yl)phosphinic acid (5 mg, 0.009 mmol, 20% yeid) as a yellow solid. MS (ES$^+$) m/z: 554 (M+H)$^+$.

Examples 13-37

Using the chemistry described for the preparation of Intermediate 2-7 and in Examples 1-12, the compounds in TABLES 1 and 2 were prepared as enantiopure compounds.

TABLE 1

| EXAMPLE | Y$^1$ | Y$^2$ | X$^3$ | X$^4$ | L$^1$ | X$^1$ | X$^5$ |
|---|---|---|---|---|---|---|---|
| 13 | —SO$_2$Me | —(CH$_2$)$_2$COOMe | N | CH | O | N | CH |
| 14 | —SO$_2$Me | —(CH$_2$)$_2$COOH | N | CH | O | N | CH |
| 15 | —SO$_2$Me | —(CH$_2$)$_2$COOMe | CH | CH | O | N | CH |
| 16 | —SO$_2$Me | —(CH$_2$)$_2$COOH | CH | CH | O | N | CH |
| 17 | —SO$_2$Me | —CH$_2$C(CH$_3$)$_2$COOH | N | CH | O | N | CH |
| 18 | —SO$_2$Me | —OCH$_2$COOH | N | CH | O | N | CH |
| 19 | —CH$_2$OCH$_3$ | —(CH$_2$)$_2$COOH | N | CH | O | N | CH |
| 20 | —CH$_2$COOH | —CF$_3$ | CH | CH | O | N | CH |
| 21 | —(CH$_2$)$_2$COOH | H | CH | CH | O | N | N |
| 22 | —(CH$_2$)$_2$COOH | H | CH | CH | O | CH | CH |
| 23 | —(CH$_2$)$_2$COOMe | H | CH | CH | O | N | N |
| 24 | —(CH$_2$)$_2$COOH | H | CH | CH | O | N | CH |
| 25 | —CH$_2$COOMe | H | CH | CH | O | N | CH |

TABLE 1-continued

| EXAMPLE | Y$^1$ | Y$^2$ | X$^3$ | X$^4$ | L$^1$ | X$^1$ | X$^5$ |
|---|---|---|---|---|---|---|---|
| 26 | —(CH$_2$)$_2$COOMe | H | CH | CH | O | N | CH |
| 27 | —CH$_2$COOH | H | CH | CH | O | N | CH |
| 28 | H | —(CH$_2$)$_2$COOMe | CH | N | S | N | CH |
| 29 | H | —(CH$_2$)$_2$COOH | CH | N | S | N | CH |

TABLE 2

| EXAMPLE | Y$^1$ | Y$^{2a}$ | Y$^{2b}$ | X$^3$ | L$^1$ |
|---|---|---|---|---|---|
| 30 | —SO$_2$Me | —Cl | —CH$_2$COOH | N | O |
| 31 | —SO$_2$Me | —(CH$_2$)$_2$COOH | H | N | O |
| 32 | —SO$_2$Me | —H | —CH$_2$COOMe | CH | O |
| 33 | —SO$_2$Me | —Cl | —CH$_2$COOH | CH | O |
| 34 | —SO$_2$Me | —H | —CH$_2$COOH | CH | O |
| 35 | —SO$_2$Me | —(CH$_2$)$_2$COOMe | —H | CH | O |
| 36 | —SO$_2$Me | —(CH$_2$)$_2$COOH | —H | CH | O |
| 37 | —SO$_2$Me | CH$_2$P(O)(OEt)$_2$ | H | N | O |

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:

1. A compound of the formula (I):

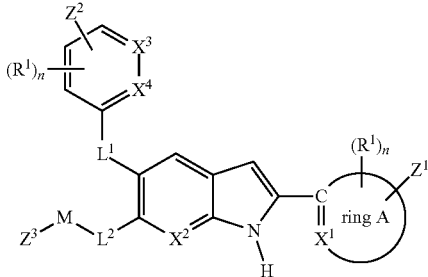

or a pharmaceutically acceptable salt thereof, wherein:

$X^1$, $X^2$, $X^3$ and $X^4$ individually represent CH or N wherein $X^3$ and $X^4$ cannot both be N;

M represents a 6- to 10-membered aryl group, a 5- to 7-membered heteroaryl group, a 5- to 7- membered cycloalkyl group, or a 5- to 7-membered aliphatic heterocyclic group, optionally substituted with 1-4 substituents independently selected from: halogen, hydroxy, oxo, $C_{1-6}$alkylOC$_{1-6}$alkyl, $C_{1-6}$alkoxy, CN, NR$^2$R$^4$, $C_{1-6}$alkylNR$^2$R$^4$, C(O)$_{1-2}$C$_{1-6}$alkyl, $C_{1-6}$alkylC(O)$_{1-2}$C$_{1-6}$alkyl, C(O)OH, $C_{1-6}$alkylCOOH, S(O)$_{0-2}$C$_{1-6}$alkyl, S(O)$_{0-2}$ or arylC$_{1-6}$alkyl, wherein the alkyl and alkoxy substituents are further optionally substituted by 1-4 substituents independently selected from: halogen or $C_{1-6}$alkyl where said $C_{1-6}$alkyl is optionally substituted by 1-6 halogens;

$L^1$ represents O or S(O)$_{0-2}$;

$L^2$ represents a single bond, O, S(O)$_{0-2}$ or CR$^2$R$^4$;

$L^3$ represents $C_{1-6}$alkyl, OC$_{1-6}$alkyl, S(O)$_{0-2}$C$_{1-6}$alkyl, $C_{1-6}$alkylOC$_{1-6}$alkyl, $C_{1-6}$alkylS(O)$_{0-2}$C$_{1-6}$alkyl or CONHC$_{1-6}$alkyl;

$Z^1$, $Z^2$ and $Z^3$ individually represent -L$^3$-COOR, -P(O)R$^3$OR, -L$^3$-P(O)R$^3$OR or null; provided that $Z^1$, $Z^2$ and $Z^3$ cannot all three be null together;

R individually represents H, $C_{1-6}$alkyl or $C_{1-6}$cycloalkyl, optionally substituted with 1-4 substituents independently selected from: halogen or hydroxy;

$R^2$ and $R^4$ individually represent H or $C_{1-6}$alkyl, optionally substituted with 1-4 substituents independently selected from: halogen or hydroxy;

$R^1$ represents H, halogen, $C_{1-6}$alkyl, $C_{1-6}$cycloalkyl, OC$_{1-6}$alkyl, S(O)$_{0-2}$C$_{1-6}$alkyl, $C_{1-6}$alkylOC$_{1-6}$alkyl, $C_{1-6}$alkylS(O)$_{0-2}$C$_{1-6}$alkyl, NR$^2$R$^4$, $C_{1-6}$alkylNR$^2$R$^4$ or C(O)NR$^2$R$^4$, wherein the alkyl substituents are optionally substituted with 1-4 substituents independently selected from: halogen or hydroxy; and further wherein the $R^2$ and $R^4$ on the C(O)NR$^2$R$^4$ can together form a 4- to 6-membered saturated heterocyclic ring having 1 nitrogen atom which 4- to 6-membered ring may be optionally substituted with 1-3 substituents independently selected from halogen, hydroxyl, oxo, $C_{1-6}$alkyl, $C_{1-6}$alkoxy or CO$_2$C$_{1-6}$alkyl where the alkyl or alkoxy substituents are optionally substituted by 1-6 halogens;

$R^3$ represents $C_{1-6}$alkyl or OC$_{1-6}$alkyl, n represents 1-4, and ring A is a substituted phenyl, isothiazolyl group, imidazolyl group, oxazolyl group, thiadiazolyl group, thienyl group, triazolyl group, tetrazolyl group, pyridyl group, pyrimidinyl group, furyl group, thiazolyl group, isoxazolyl group or pyrazolyl group; or a pharmaceutically acceptable salt thereof.

2. The compound of claim 1 wherein M is a phenyl group, isothiazolyl group, imidazolyl group, oxazolyl group, thiadiazolyl group, thienyl group, triazolyl group, tetrazolyl group, pyridyl group, pyrimidinyl group, furyl group, thiazolyl group, isoxazolyl group or pyrazolyl group, optionally substituted with halogen, hydroxy, oxo, $C_{1-6}$alkyl, $C_{1-6}$alkylOC$_{1-6}$alkyl, $C_{1-6}$alkoxy, CN, NR$^2$R$^4$, $C_{1-6}$alkylNR$^2$R$^4$, C(O)$_{1-2}$C$_{1-6}$alkyl, $C_{1-6}$alkylC(O)$_{1-2}$C$_{1-6}$alkyl, C(O)OH, $C_{1-6}$alkylCOOH, S(O)$_{0-2}$C$_{1-6}$alkyl, S(O)$_{0-2}$ or arylC$_{1-6}$alkyl, wherein the alkyl and alkoxy substituents are further optionally substituted by 1-4 substituents independently selected from: halogen or $C_{1-6}$alkyl where said $C_{1-6}$alkyl is optionally substituted by 1-6 halogens; or a pharmaceutically acceptable salt thereof.

3. The compound of claim 1 wherein M is phenyl, pyrrolidine or pyridyl, optionally substituted with 1-4 substituents independently selected from: halogen, oxo, $C_{1-6}$alkyl, $C_{1-6}$alkylOC$_{1-6}$alkyl, $C_{1-6}$alkoxy, C(O)$_{1-2}$C$_{1-6}$alkyl, $C_{1-6}$alkylC(O)$_{1-2}$C$_{1-6}$alkyl, C(O)OH or $C_{1-6}$alkylCOOH, wherein the alkyl is further optionally substituted by 1-6 halogen substituents; or a pharmaceutically acceptable salt thereof.

4. The compound of claim 1 wherein M is phenyl or pyrrolidine, optionally substituted with 1-4 substituents independently selected from: halogen, oxo, $C_{1-6}$alkyl, $C_{1-6}$alkylOC$_{1-6}$alkyl, $C_{1-6}$alkoxy, C(O)$_{1-2}$C$_{1-6}$alkyl, $C_{1-6}$alkylC(O)$_{1-2}$C$_{1-6}$alkyl, C(O)OH or $C_{1-6}$alkylCOOH, wherein the alkyl is further optionally substituted by 1-6 halogen substituents; or a pharmaceutically acceptable salt thereof.

5. The compound of claim 1 wherein $L^1$ is O; or a pharmaceutically acceptable salt thereof.

6. The compound of claim 1 wherein $L^2$ is a single bond or CR$^2$R$^4$; or a pharmaceutically acceptable salt thereof.

7. The compound of claim 1 wherein $L^3$ is $C_{1-6}$alkyl, OC$_{1-6}$alkyl or CONHC$_{1-6}$alkyl; or a pharmaceutically acceptable salt thereof.

8. The compound of claim 1 wherein one of $Z^1$, $Z^2$ and $Z^3$ is -L$^3$-COOR, -P(O)R$^3$OR or -L$^3$-P(O)R$^3$OR, and the other two are null; or a pharmaceutically acceptable salt thereof.

9. The compound of claim 1 wherein R individually represents H or $C_{1-6}$alkyl, wherein $C_{1-6}$alkyl is optionally substituted with 1-6 halogen substituents; or a pharmaceutically acceptable salt thereof.

10. The compound of claim 1 wherein $R^1$ is individually selected from hydrogen, halogen, $C_{1-6}$alkyl, $C_{1-6}$alkyl-OC$_{1-6}$alkyl, S(O)$_{0-2}$C$_{1-6}$alkyl or C(O)NR$^2$R$^4$, wherein the alkyl substituents are optionally substituted with 1-4 substituents independently selected from: halogen or hydroxy; and further wherein the $R^2$ and $R^4$ on the C(O)NR$^2$R$^4$ together form a 4-membered saturated heterocyclic ring having 1 nitrogen atom which 4-membered ring may be optionally substituted with 1-3 substituents independently selected from halogen, hydroxyl, oxo, $C_{1-6}$alkoxy or CO$_2$C$_{1-6}$alkyl where the alkyl or alkoxy substituents are optionally substituted by 1-6 halogens; or a pharmaceutically acceptable salt thereof.

11. The compound of claim 1 wherein ring A is a substituted pyridyl, pyrazinyl or phenyl group; or a pharmaceutically acceptable salt thereof.

12. The compound which is:

methyl 3-(6-{5-[4-(ethylsulfonyl)phenoxy]-6-(1-methyl-5-oxopyrrolidin-2-yl)-1H-indol-2-yl}pyridin-3-yl)propanoate;

3-(6-{5-[4-(ethylsulfonyl)phenoxy]-6-(1-methyl-5-oxopyrrolidin-2-yl)-1H-indol-2-yl}pyridin-3-yl)propanoic acid;
(2-{5-[4-(ethylsulfonyl)phenoxy]-2-[5-(trifluoromethyl)pyridin-2-yl]-1H-indol-6-yl}-5-oxopyrrolidin-1-yl)acetic acid;
methyl 3-[4-({6-(1-methyl-5-oxopyrrolidin-2-yl)-2-[5-(trifluoro-methyl)pyridin-2-yl]-1H-indol-5-yl}oxy)phenyl]propionate;
3-[4-({6-(1-methyl-5-oxopyrrolidin-2-yl)-2-[5-(trifluoromethyl)pyridin-2-yl]-1H-indol-5-yl}oxy)phenyl]propanoic acid;
methyl 3-(6-{6-(2-fluorophenoxy)-5-[4-(methylsulfonyl)phenoxy]-1H-indol-2-yl}pyridin-3-yl)propanoate;
3-(6-{6-(2-fluorophenoxy)-5-[4-(methylsulfonyl)phenoxy]-1H-indol-2-yl}pyridin-3-yl)propanoic acid;
n-({6-[6-(1-methyl-5-oxopyrrolidin-2-yl)-5-{[6-(methylsulfonyl)pyridin-3-yl]oxy}-1H-indol-2-yl]pyridin-3-yl}-carbonyl)-β-alanine;
3-[6-(5-{[6-(methylsulfonyl)pyridin-3-yl]oxy}-6-[(2-oxopyrrolidin-1-yl)methyl]-1H-pyrrolo[2,3-b]pyridin-2-yl)pyridin-3-yl]propanoic acid;
methyl 3-{6-[6-(1-acetylpyrrolidin-2-yl)-5-{[6-(azetidin-1-ylcarbonyl)pyridin-3-yl]oxy}-1H-indol-2-yl]pyridin-3-yl}propanoate;
3-{6-[6-(1-acetylpyrrolidin-2-yl)-5-{-[6-(azetidin-1-ylcarbonyl)pyridin-3-yl]oxy}-1H-indol-2-yl]pyridin-3-yl}propanoic acid;
(6-(5-(4-(ethylsulfonyl)phenoxy)-6-(1-methyl-5-oxopyrrolidin-2-yl)-1H-indol-2-yl)pyridin-3-yl)(methyl)phosphinic acid;
methyl 3-(6-(6-(1-methyl-5-oxopyrrolidin-2-yl)-5-((6-(methylsulfonyl)pyridin-3-yl)oxy)-1H-indol-2-yl)pyridin-3-yl)propanoate;
3-(6-(6-(1-methyl-5-oxopyrrolidin-2-yl)-5-((6-(methylsulfonyl)pyridin-3-yl)oxy)-1H-indol-2-yl)pyridin-3-yl)propanoic acid;
methyl 3-(6-(6-(1-methyl-5-oxopyrrolidin-2-yl)-5-(4-(methylsulfonyl)phenoxy)-1H-indol-2-yl)pyridin-3-yl)propanoate;
3-(6-(6-(1-methyl-5-oxopyrrolidin-2-yl)-5-(4-(methylsulfonyl)phenoxy)-1H-indol-2-yl)pyridin-3-yl)propanoic acid;
2,2-dimethyl-3-(6-(6-(1-methyl-5-oxopyrrolidin-2-yl)-5-((6-(methylsulfonyl)pyridin-3-yl)oxy)-1H-indol-2-yl)pyridin-3-yl)propanoic acid;
2-((6-(6-(1-methyl-5-oxopyrrolidin-2-yl)-5-((6-(methylsulfonyl)pyridin-3-yl)oxy)-1H-indol-2-yl)pyridin-3-yl)oxy)acetic acid;
3-(6-(5-((6-(methoxymethyl)pyridin-3-yl)oxy)-6-(1-methyl-5-oxopyrrolidin-2-yl)-1H-indol-2-yl)pyridin-3-yl)propanoic acid;
2-(4-((6-(1-methyl-5-oxopyrrolidin-2-yl)-2-(5-(trifluoromethyl)pyridin-2-yl)-1H-indol-5-yl)oxy)phenyl)acetic acid;
3-(4-((6-(1-methyl-5-oxopyrrolidin-2-yl)-2-(pyrazin-2-yl)-1H-indol-5-yl)oxy)phenyl)propanoic acid;
3-(4-((6-(1-methyl-5-oxopyrrolidin-2-yl)-2-phenyl-1H-indol-5-yl)oxy)phenyl)propanoic acid;
methyl 3-(4-((6-(1-methyl-5-oxopyrrolidin-2-yl)-2-(pyrazin-2-yl)-1H-indol-5-yl)oxy)phenyl)propanoate;
3-(4-((6-(1-methyl-5-oxopyrrolidin-2-yl)-2-(pyridin-2-yl)-1H-indol-5-yl)oxy)phenyl)propanoic acid;
methyl 2-(4-((6-(1-methyl-5-oxopyrrolidin-2-yl)-2-(pyridin-2-yl)-1H-indol-5-yl)oxy)phenyl)acetate;
methyl 3-(4-((6-(1-methyl-5-oxopyrrolidin-2-yl)-2-(pyridin-2-yl)-1H-indol-5-yl)oxy)phenyl)propanoate;
2-(4((6-(1-methyl-5-oxopyrrolidin-2-yl)-2-(pyridin-2-yl)-1H-indol-5-yl)oxy)phenyl)acetic acid;
methyl 3-(6-(6-(1-methyl-5-oxopyrrolidin-2-yl)-5-(pyridin-2-ylthio)-1H-indol-2-yl)pyridin-3-yl)propanoate;
3-(6-(6-(1-methyl-5-oxopyrrolidin-2-yl)-5-(pyridin-2-ylthio)-1H-indol-2-yl)pyridin-3-yl)propanoic acid;
2-(5-chloro-2-(6-(1-methyl-5-oxopyrrolidin-2-yl)-5-((6-(methylsulfonyl)pyridin-3-yl)oxy)-1H-indol-2-yl)thiazol-4-yl)acetic acid;
3-(2-(6-(1-methyl-5-oxopyrrolidin-2-yl)-5-((6-(methylsulfonyl)pyridin-3-yl)oxy)-1H-indol-2-yl)thiazol-5-yl)propanoic acid;
methyl 2-(2-(6-(1-methyl-5-oxopyrrolidin-2-yl)-5-(4-(methylsulfonyl)phenoxy)-1H-indol-2-yl)thiazol-4-yl)acetate;
2-(5-chloro-2-(6-(1-methyl-5-oxopyrrolidin-2-yl)-5-(4-(methylsulfonyl)phenoxy)-1H-indol-2-yl)thiazol-4-yl)acetic acid;
2-(2-(6-(1-methyl-5-oxopyrrolidin-2-yl)-5-(4-(methylsulfonyl)phenoxy)-1H-indol-2-yl)thiazol-4-yl)acetic acid;
methyl 3-(2-(6-(1-methyl-5-oxopyrrolidin-2-yl)-5-(4-(methylsulfonyl)phenoxy)-1H-indol-2-yl)thiazol-5-yl)propanoate;
3-(2-(6-(1-methyl-5-oxopyrrolidin-2-yl)-5-(4-(methylsulfonyl)phenoxy)-1H-indol-2-yl)thiazol-5-yl)propanoic acid;
diethyl ((2-(6-(1-methyl-5-oxopyrrolidin-2-yl)-5-((6-(methylsulfonyl)pyridin-3-yl)oxy)-1H-indol-2-yl)thiazol-5-yl)methyl)phosphonate;
or a pharmaceutically acceptable salt thereof.

13. A pharmaceutical composition comprising the compound of claim 1, and a pharmaceutically acceptable carrier.

14. The compound of claim 1 wherein one of $Z^1$, $Z^2$ and $Z^3$ is -$L^3$-COOR, and the other two are null; or a pharmaceutically acceptable salt thereof.

15. The compound of claim 1 wherein one of $Z^1$, $Z^2$ and $Z^3$ is —P(O)$R^3$OR, and the other two are null; or a pharmaceutically acceptable salt thereof.

16. The compound of claim 1 wherein one of $Z^1$, $Z^2$ and $Z^3$ is -$L^3$-P(O)$R^3$OR, and the other two are null; or a pharmaceutically acceptable salt thereof.

* * * * *

UNITED STATES PATENT AND TRADEMARK OFFICE
CERTIFICATE OF CORRECTION

PATENT NO.        : 9,453,038 B2
APPLICATION NO.   : 14/652883
DATED             : September 27, 2016
INVENTOR(S)       : Songnian Lin et al.

Page 1 of 1

It is certified that error appears in the above-identified patent and that said Letters Patent is hereby corrected as shown below:

On the Title Page

Item (54) and in the Specification, Column 1, Line 1:
Replace "Glucokinase Activator Compounds, Compositions Containing Such Compounds, and Methods of Treatment"
With --"Novel Glucokinase Activator Compounds, Compositions Containing Such Compounds, and Methods of Treatment"--

In the Claims

Column 69, Line 26, Claim 1:
Insert --,C1-6alkyl,-- after oxo

Signed and Sealed this
Ninth Day of January, 2018

Joseph Matal
*Performing the Functions and Duties of the
Under Secretary of Commerce for Intellectual Property and
Director of the United States Patent and Trademark Office*